(12) United States Patent
Paone et al.

(10) Patent No.: US 7,745,427 B2
(45) Date of Patent: Jun. 29, 2010

(54) CGRP RECEPTOR ANTAGONISTS

(75) Inventors: Daniel V. Paone, Lansdale, PA (US);
Diem N. Nguyen, Harleysville, PA (US);
Christopher S. Burgey, Philadelphia, PA (US); James Z. Deng, Eagleville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 542 days.

(21) Appl. No.: 11/665,943

(22) PCT Filed: Oct. 18, 2005

(86) PCT No.: PCT/US2005/037653
§ 371 (c)(1),
(2), (4) Date: Apr. 20, 2007

(87) PCT Pub. No.: WO2006/047196
PCT Pub. Date: May 4, 2006

(65) Prior Publication Data
US 2008/0090806 A1 Apr. 17, 2008

Related U.S. Application Data

(60) Provisional application No. 60/621,111, filed on Oct. 22, 2004.

(51) Int. Cl.
| C07D 471/04 | (2006.01) |
| C07D 471/20 | (2006.01) |
| A61K 31/55 | (2006.01) |
| A61P 25/06 | (2006.01) |

(52) U.S. Cl. ................... 514/217.05; 540/599
(58) Field of Classification Search ............... 540/599; 514/217.05
See application file for complete search history.

(56) References Cited

U.S. PATENT DOCUMENTS 5,635,510 A 6/1997 Burkholder

FOREIGN PATENT DOCUMENTS

| WO | 00/18764 | 4/2000 |
| WO | 03/104236 | 12/2003 |
| WO | 2004/055016 | 7/2004 |
| WO | WO 2004/092166 | 10/2004 |
| WO | 2005/035524 | 4/2005 |

OTHER PUBLICATIONS

Supplementary European Search Report, Oct. 26, 2009.
Anthony E. Lanzilotti, et al., "Stereoselective reduction of some indoles with triethylsilane-trifluoroacetic acid", Journal of Organic Chemistry, American Chemical Society, Easton, US. vol. 44, No. 26, Jul. 1, 1979, pp. 4809-4813.

*Primary Examiner*—Bruck Kifle
(74) *Attorney, Agent, or Firm*—Gerard Devlin; Raynard Yuro

(57) ABSTRACT

The present invention is directed to compounds of Formula (I) and Formula (II) (where variables R1, R2, R3, R4, A, B, G, J, Q, T, U, V, W, X and Y are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

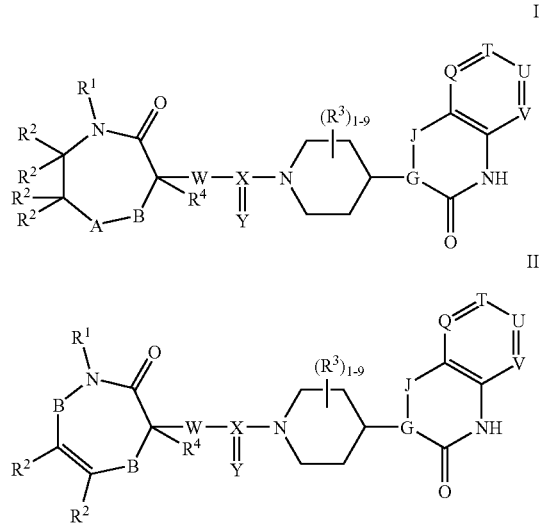

8 Claims, No Drawings

CGRP RECEPTOR ANTAGONISTS

Related Application Data

This is a National filing under 35 USC 371 of PCT/US2005/037653, filed Oct. 18, 2005, which claims priority from U.S. Ser. No. 60/621,111, filed Oct. 22, 2004.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist. In recently reported clinical trials, the CGRP receptor antagonist BIBN 4096 BS was reported to be effective in treating acute attacks of migraine (Olesen et al., N. Engl. J. Med. 2004, 350:1104-1110).

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of Formula I:

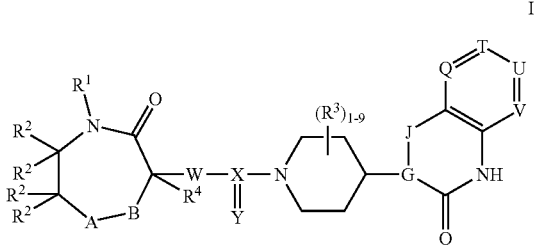

and Formula II:

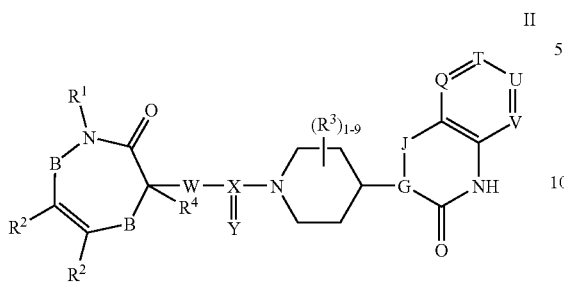

(where variables $R^1$, $R^2$, $R^3$, $R^4$, A, B, G, J, Q, T, U, V, W, X and Y are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to CGRP antagonists which include compounds of Formula I:

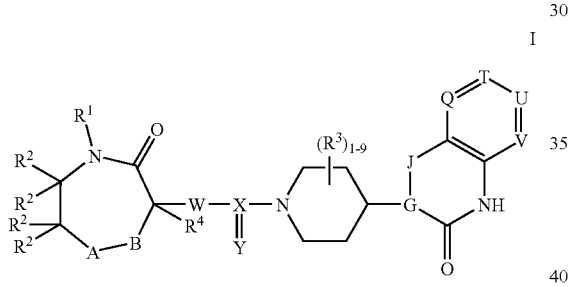

wherein:
A is a bond, $C(R^2)_2$, O, $S(O)_m$ or $NR^2$;
B is $(C(R^2)_2)_n$;
$R^1$ is selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and,
   v) $O(CO)R^4$;
2) aryl or heteroaryl, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   P)$SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$;
$R^2$ is independently selected from:
1) H, $C_0$—$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$, p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and,
v) $O(CO)R^4$;

2) aryl or heteroaryl, unsubstituted or substituted with one or more substituents independently selected from:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents where the substituents are independently selected from $R^4$,
e) heterocycle, unsubstituted or substituted with 1-5 substituents where the substituents are independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$, or, any two independent $R^2$ on the same or adjacent atoms may be joined together to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl, or morpholinyl, which is unsubstituted or substituted with 1-5 substituents where the substituents are independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;
X is C or S;
Y is O, $(R^4)_2$, NCN, $NSO_2CH_3$, $NCONH_2$, or Y is $O_2$ when X is S;
$R^6$ is independently selected from H and:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents where the substituents are independently selected from $R^4$,
e) heterocycle, unsubstituted or substituted with 1-5 substituents where the substituents are independently selected from $R^4$,
f) $(F)_pC_{1-3}$ alkyl,
g) halogen,
h) $OR^4$,
i) $O(CH_2)_sOR^4$,
j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$;

G-J is selected from: N, $N-C(R^5)_2$, $C=C(R^5)$, $C=N$; $C(R^5)$, $C(R^5)-C(R^5)_2$, $C(R^5)-C(R^5)_2-C(R^5)_2$, $C=C(R^5)-C(R^5)_2$, $C(R^5)-C(R^5)=C(R^5)$, $C(R^5)-C(R^5)_2-N(R^5)$, $C=C(R^5)-N(R^5)$, $C(R^5)-C(R^5)=N$, $C(R^5)-N(R^5)-C(R^5)_2$, $C=N-C(R^5)_2$, $C(R^5)-N=C(R^5)$, $C(R^5)-N(R^5)-N(R^5)$, $C=N-N(R^5)$, $N-C(R^5)_2-C(R^5)_2$, $N-C(R^5)=C(R^5)$, $N-C(R^5)_2-N(R^5)$, $N-C(R^5)=N$, $N-N(R^5)-C(R^5)_2$ and $N-N=C(R^5)$;

Q, T, U and V are each independently a carbon atom or a nitrogen atom wherein at least one but no more than three of Q, T, U and V are nitrogen atoms, of which one may be optionally an N-oxide, and wherein when any of Q, T, U, or V is a carbon atom it is unsubstituted or substituted where the substituents are independently selected from $R^6$;

$R^5$ is independently selected from H, substituted or unsubstituted $C_1$-$C_3$ alkyl, CN, $OR^4$, $N(R^4)_2$ and $CO_2R^4$;
$R^3$ is independently selected from H, substituted or unsubstituted $C_1$-$C_3$ alkyl, F, CN and $CO_2R^4$;
p is 0 to 2q+1, for a substituent with q carbons;
m is 0, 1 or 2;
n is 0 or 1;
s is 1, 2 or 3;

and pharmaceutically acceptable salts and individual diastereomers thereof.

Further embodiments of the invention are CGRP antagonists of Formula I which include compounds of the Formula Ia:

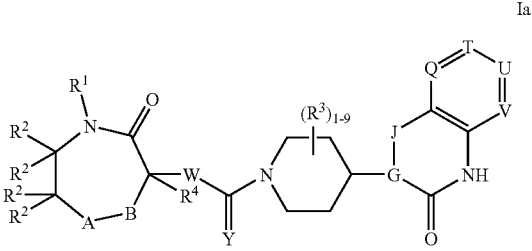

Ia wherein:
A is a bond, $C(R^2)_2$, O, $S(O)_m$ or $NR^2$;
B is $(C(R^2)_2)_n$;
Y is O or NCN; and
n is 0 or 1; and
$R^1$, $R^2$, $R^4$, W, Y, $R^3$, G-J, Q, T, U, V and m are as defined in Formula I;

and pharmaceutically acceptable salts and individual stereoisomers thereof.

Still further embodiments of the invention are CGRP antagonists of Formula I which include compounds of the Formula Ib:

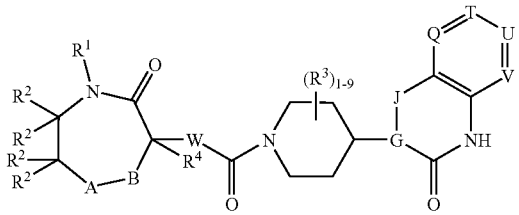

Ib wherein:
A is a bond, $C(R^2)_2$, O, $S(O)_m$ or $NR^2$;
B is $(C(R^2)_2)_n$;
n is 0 or 1; and
$R^1$, $R^2$, $R^4$, W, $R^3$, G-J, Q, T, U, V and m are as defined in Formula I;

and pharmaceutically acceptable salts and individual stereoisomers thereof.

Additional embodiments of the invention are CGRP antagonists of Formula I which include compounds of the Formula Ic:

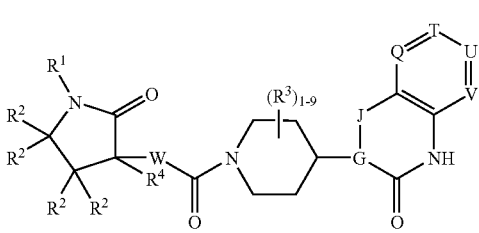

Ic wherein:
$R^1$, $R^2$, $R^4$, W, $R^3$, G-J, Q, T, U, V and m are as defined in Formula I;

and pharmaceutically acceptable salts and individual stereoisomers thereof.

Additional embodiments of the invention are CGRP antagonists of Formula I which also include compounds of the Formula Id:

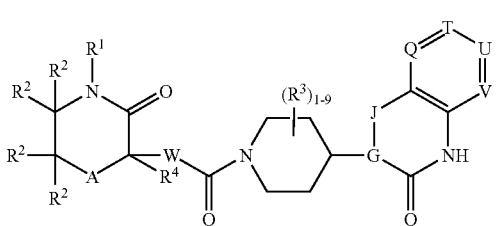

Id wherein:
A is $C(R^2)_2$, O, $S(O)_m$ or $NR^2$;
$R^1$, $R^2$, $R^4$, W, $R^3$, G-J, Q, T, U, V and m are as defined in Formula I;

and pharmaceutically acceptable salts and individual stereoisomers thereof.

Additional embodiments of the invention are CGRP antagonists of Formula I which include compounds of the Formula Ie:

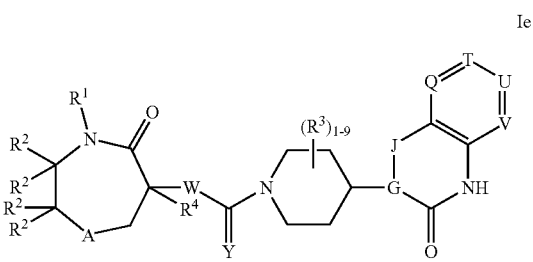

Ie wherein:
A is $C(R^2)_2$, O, $S(O)_m$ or $NR^2$;
$R^1$, $R^2$, $R^4$, W, $R^3$, G-J, Q, T, U, V and m are as defined in Formula I;

and pharmaceutically acceptable salts and individual stereoisomers thereof.

Further embodiments of the invention are CGRP antagonists of Formulae Ia-Ie, wherein:

$R^1$ is selected from:
1) H, $C_1$-$C_6$ alkyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents where the substituents are independently selected from $R^4$,
   e) heterocycle, unsubstituted or substituted with 1-5 substituents where the substituents are independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10}R^{11}$, and
   m) $O(CO)R^4$; and
2) aryl or heteroaryl, unsubstituted or substituted with one or more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$, k) CN,
l) NR$^{10}$R$^{11}$, and,
m) O(CO)R$^4$;

R$^2$ is selected from:
1) H, C$_0$-C$_6$ alkyl, C$_2$-C$_6$ alkynyl, C$_{3-6}$ cycloalkyl and heterocycle, unsubstituted or substituted with one or more substituents independently selected from:
   a) C$_{1-6}$ alkyl,
   b) C$_{3-6}$ cycloalkyl,
   c) aryl, unsubstituted or substituted with 1-5 substituents where the substituents are independently selected from R$^4$,
   d) heteroaryl, unsubstituted or substituted with 1-5 substituents where the substituents are independently selected from R$^4$,
   e) heterocycle, unsubstituted or substituted with 1-5 substituents where the substituents are independently selected from R$^4$,
   f) (F)$_p$C$_{1-3}$ alkyl,
   g) halogen,
   h) OR$^4$,
   i) O(CH$_2$)$_s$OR$^4$,
   j) CO$_2$R$^4$,
   k) S(O)$_m$R$^4$,
   l) CN,
   m) NR$^{10}$R$^{11}$, and
   n) O(CO)R$^4$; and
2) aryl or heteroaryl, unsubstituted or substituted with one more substituents independently selected from:
   a) C$_{1-6}$ alkyl,
   b) C$_{3-6}$ cycloalkyl,
   c) (F)$_p$C$_{1-3}$ alkyl,
   d) halogen,
   e) OR$^4$,
   f) CO$_2$R$^4$,
   g) (CO)NR$^{10}$R$^{11}$,
   h) SO$_2$NR$^{10}$R$^{11}$,
   i) N(R$^{10}$)SO$_2$R$^{11}$,
   j) S(O)$_m$R$^4$,
   k) CN,
   l) NR$^{10}$R$^{11}$, and
   m) O(CO)R$^4$,
   or, any two independent R$^2$ on the same or adjacent atoms may be joined together to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

R$^{10}$ and R$^{11}$ are independently selected from: H, C$_{1-6}$ alkyl, (F)$_p$C$_{1-6}$ alkyl, C$_{3-6}$ cycloalkyl, aryl, heteroaryl and benzyl, unsubstituted or substituted with halogen, hydroxy or C$_1$-C$_6$ alkoxy, where R$^{10}$ and R$^{11}$ may be joined together to form a ring selected from: azetidinyl, pyrrolidinyl, piperidinyl, piperazinyl and morpholinyl, which is unsubstituted or substituted with 1-5 substituents where the substituents are independently selected from R$^4$ R$^4$ is independently selected from: H, C$_{1-6}$ alkyl, (F)$_p$C$_{1-6}$ alkyl, C$_{3-6}$ cycloalkyl, aryl, heteroaryl and benzyl, unsubstituted or substituted with halogen, hydroxy or C$_1$-C$_6$ alkoxy;

W is O, NR$^4$ or C(R$^4$)$_2$;

G-J is selected from:

N, such that when G-J is so defined the following structure forms:

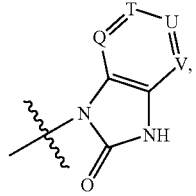

N—C(R$^5$)$_2$, such that when G-J is so defined the following structure forms:

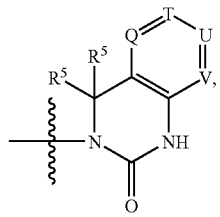

C═C(R$^5$), such that when G-J is so defined the following structure forms:

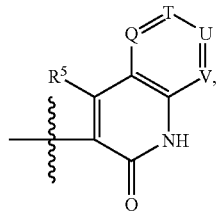

C═N, such that when G-J is so defined the following structure forms:

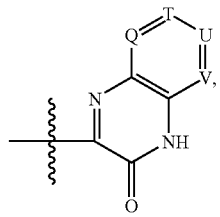

C═C(R$^5$)—C(R$^5$)$_2$, such that when G-J is so defined the following structure forms:

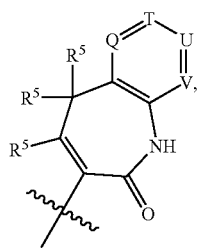

C(R$^5$)—C(R$^5$)═C(R$^5$), such that when G-J is so defined the following structure forms:

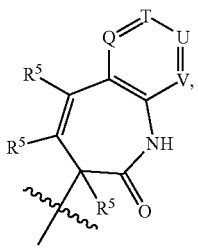

N—C(R$^5$)$_2$—C(R$^5$)$_2$, such that when G-J is so defined the following structure forms:

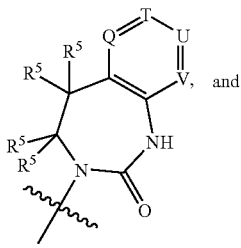

N—C(R$^5$)=C(R$^5$), such that when G-J is so defined the following structure forms:

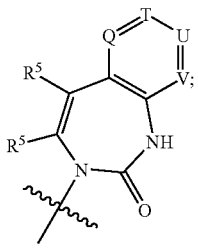

Q, T, U and V are each independently a carbon atom or a nitrogen atom wherein at least one but no more than three of Q, T, U and V are nitrogen atoms, of which one may be optionally an N-oxide, and wherein when any of Q, T, U, or V is a carbon atom it is unsubstituted or substituted where the substituents are independently selected from R$^6$;

R$^6$ is independently selected from H and:
  a) C$_{1-6}$ alkyl,
  b) C$_{3-6}$ cycloalkyl,
  c) (F)$_p$C$_{1-3}$ alkyl
  d) halogen,
  e) OR$^4$,
  f) CO$_2$R$^4$,
  g) (CO)NR$^{10}$R$^{11}$,
  h) SO$_2$NR$^{10}$R$^{11}$,
  i) N(R$^{10}$)SO$_2$R$^{11}$,
  j) S(O)$_m$R$^4$,
  k) CN,
  l) NR$^{10}$R$^{11}$ and
  m) O(CO)R$^4$; and R$^5$ is independently selected from H, substituted or unsubstituted C$_1$-C$_3$ alkyl, CN, OR$^4$, N(R$^4$)$_2$ and CO$_2$R$^4$;

R$^3$ is independently selected from H, substituted or unsubstituted C$_1$-C$_3$ alkyl, F, CN and CO$_2$R$^4$;

p is 0 to 2q+1, for a substituent with q carbons
m is 0 to 2;
s is 1 to 3;

and pharmaceutically acceptable salts and individual stereoisomers thereof.

Still further embodiments of the invention are CGRP antagonists of Formulae Ia-Ie, wherein:

R$^1$ is selected from:
  1) H, C$_1$-C$_6$ alkyl, C$_{3-6}$ cycloalkyl and heterocycle, unsubstituted or substituted with one or more substituents independently selected from:
    a) C$_{1-6}$ alkyl,
    b) C$_{3-6}$ cycloalkyl,
    c) phenyl, unsubstituted or substituted with 1-5 substituents where the substituents are independently selected from R$^4$,
    d) heteroaryl, unsubstituted or substituted with 1-5 substituents where the substituents are independently selected from R$^4$,
      and where heteroaryl is selected from: imidazole, isoxazole, oxazole, pyrazine, pyrazole, pyridazine, pyridine, pyrimidine, and thiazole;
    e) heterocycle, unsubstituted or substituted with 1-5 substituents where the substituents are independently selected from R$^4$, and where heterocycle is selected from: azetidine, dioxane, dioxolane, morpholine, oxetane, piperazine, piperidine, pyrrolidine, tetrahydrofuran, and tetrahydropyran;
    f) (F)$_p$C$_{1-3}$ alkyl,
    g) halogen,
    h) OR$^4$,
    i) O(CH$_2$)$_s$OR$^4$,
    j) CO$_2$R$^4$,
    k) CN,
    l) NR$^{10}$R$^{11}$,
    m) O(CO)R$^4$;
  2) aryl or heteroaryl, selected from:
    phenyl, imidazole, isoxazole, oxazole, pyrazine, pyrazole, pyridazine, pyridine, pyrimidine, and thiazole, unsubstituted or substituted with one or more substituents independently selected from:
      a) C$_{1-6}$ alkyl,
      b) C$_{3-6}$ cycloalkyl,
      c) (F)$_p$C$_{1-3}$ alkyl,
      d) halogen,
      e) OR$^4$,
      f) CO$_2$R$^4$,
      g) (CO)NR$^{10}$R$^{11}$,
      h) SO$_2$NR$^{10}$R$^{11}$,
      i) N(R$^{10}$)SO$_2$R$^{11}$,
      j) S(O)$_m$R$^4$,
      k) CN,
      l) NR$^{10}$R$^{11}$, and
      m) O(CO)R$^4$;

R$^2$ is selected from:
  1) H, C$_0$-C$_6$ alkyl, C$_{3-6}$ cycloalkyl and heterocycle, unsubstituted or substituted with one or more substituents independently selected from:
    a) C$_{1-6}$ alkyl,
    b) C$_{3-6}$ cycloalkyl,
    c) phenyl, unsubstituted or substituted with 1-5 substituents where the substituents are independently selected from R$^4$,
    d) heteroaryl, unsubstituted or substituted with 1-5 substituents where the substituents are independently selected from R$^4$, and where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;

e) heterocycle, unsubstituted or substituted with 1-5 substituents where the substituents are independently selected from $R^4$, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;

f) $(F)_p C_{1-3}$ alkyl,
g) halogen,
h) $OR^4$,
i) $O(CH_2)_s OR^4$,
j) $CO_2 R^4$,
k) CN,
l) $NR^{10} R^{11}$, and
m) $O(CO)R^4$; and 2) aryl or heteroaryl, selected from:
   phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole;
   unsubstituted or substituted with one or more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10} R^{11}$,
   h) $SO_2 NR^{10} R^{11}$,
   i) $N(R^{10}) SO_2 R^{11}$,
   j) $S(O)_m R^4$,
   k) CN,
   l) $NR^{10} R^{11}$, and
   m) $O(CO)R^4$, or, any two independent $R^2$ on the same or adjacent atoms may be joined together to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, $R^{10}$ and $R^{11}$ are independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ may be joined together to form a ring selected from: azetidinyl, pyrrolidinyl, piperidinyl, piperazinyl and morpholinyl, which is unsubstituted or substituted with 1-5 substituents where the substituents are independently selected from $R^4$;

$R^4$ is independently selected from: H, $C_{1-6}$ alkyl, $(F)_p C_{1-6}$ alkyl, $C_{3-6}$ cycloalkyl, aryl, heteroaryl and phenyl, unsubstituted or substituted with hydroxy or $C_1$-$C_6$ alkoxy;

W is $NR^4$ or $C(R^4)_2$;

G-J and Q-T-U-V are as follows:

G-J is N and Q-T-U-V is $N=C(R^6)-C(R^6)=C(R^6)$, such that when G-J and Q-T-U-V are so defined the following structure forms:

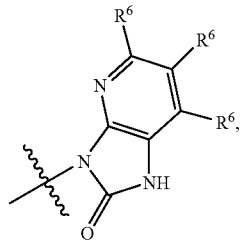

G-J is N and Q-T-U-V is $C(R^6)=N-C(R^6)=C(R^6)$, such that when G-J and Q-T-U-V are so defined the following structure forms:

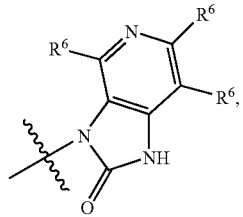

G-J is N and Q-T-U-V is $C(R^6)=C(R^6)-N=C(R^6)$, such that when G-J and Q-T-U-V are so defined the following structure forms:

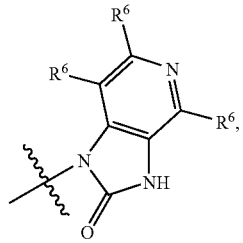

G-J is N and Q-T-U-V is $C(R^6)=C(R^6)-C(R^6)=N$, such that when G-J and Q-T-U-V are so defined the following structure forms:

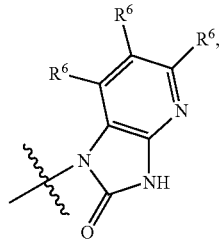

G-J is N and Q-T-U-V is $C(R^6)=C(R^6)-N=N$, such that when G-J and Q-T-U-V are so defined the following structure forms:

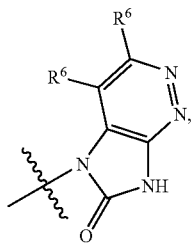

G-J is N and Q-T-U-V is C(R$^6$)=N—C(R$^6$)=N, such that when G-J and Q-T-U-V are so defined the following structure forms:

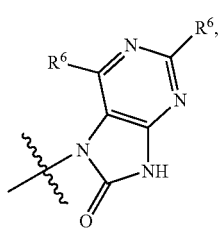

G-J is N and Q-T-U-V is N=C(R$^6$)—C(R$^6$)=N, such that when G-J and Q-T-U-V are so defined the following structure forms:

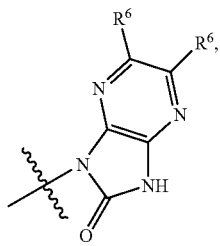

G-J is N—C(R$^5$)$_2$ and Q-T-U-V is C(R$^6$)=C(R$^6$)=N, such that when G-J and Q-T-U-V are so defined the following structure forms:

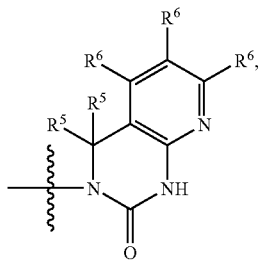

G-J is N—C(R$^5$)$_2$ and Q-T-U-V is C(R$^6$)=N—C(R$^6$)=C(R$^6$), such that when G-J and Q-T-U-V are so defined the following structure forms:

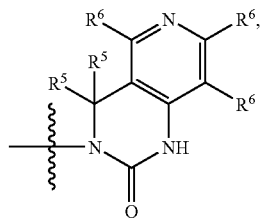

G-J is C=C(R$^5$) and Q-T-U-V is C(R$^6$)=C(R$^6$)—C(R$^6$)=N, such that when G-J and Q-T-U-V are so defined the following structure forms:

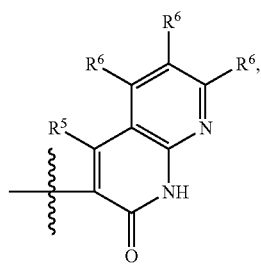

G-J is C=C(R$^5$) and Q-T-U-V is C(R$^6$)=N—C(R$^6$)=C(R$^6$), such that when G-J and Q-T-U-V are so defined the following structure forms:

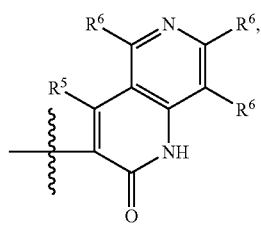

G-J is C=N and Q-T-U-V is C(R$^6$)=C(R$^6$)—C(R$^6$)=N, such that when G-J and Q-T-U-V are so defined the following structure forms:

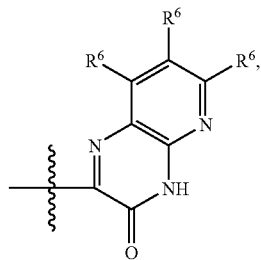

G-J is C=N and Q-T-U-V is C(R$^6$)=N—C(R$^6$)=C(R$^6$), such that when G-J and Q-T-U-V are so defined the following structure forms:

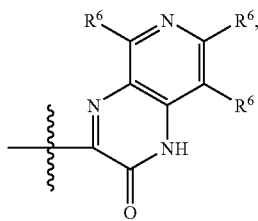

G-J is N—C(R⁵)₂—C(R⁵)₂ and Q-T-U-V is C(R⁶)═C(R⁶)—C(R⁶)═N, such that when G-J and Q-T-U-V are so defined the following structure forms:

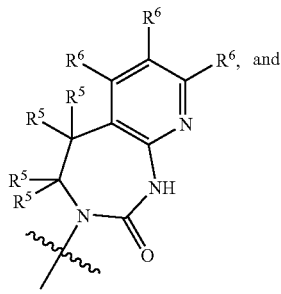

G-J is N—C(R⁵)₂—C(R⁵)₂ and Q-T-U-V is C(R⁶)═N—C(R⁶)═C(R⁶), such that when G-J and Q-T-U-V are so defined the following structure forms:

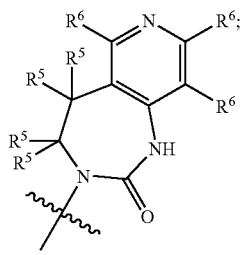

$R^6$ is independently selected from H and:
a) $C_{1-6}$ alkyl,
b) $C_{3-6}$ cycloalkyl,
c) $(F)_p C_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_m R^4$,
k) CN,
l) $NR^{10}R^{11}$, and
m) $O(CO)R^4$;

$R^5$ is independently selected from H, substituted or unsubstituted $C_1$-$C_3$ alkyl, CN, $OR^4$, $N(R^4)_2$ and $CO_2R^4$;

$R^3$ is independently selected from H, substituted or unsubstituted $C_1$-$C_3$ alkyl, F, CN and $CO_2R^4$;

p is 0 to 2q+1, for a substituent with q carbons
m is 0 to 2;
s is 1 to 3;

and pharmaceutically acceptable salts and individual stereoisomers thereof.

Another embodiment of the invention includes CGRP antagonists which include compounds of Formula II:

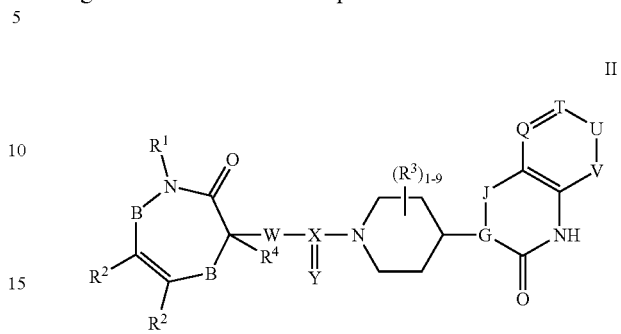

wherein:
B, G, J, Q, T, U, V, W, X, Y, $R^1$, $R^2$, $R^3$ and $R^4$ are as defined in Formula I, and pharmaceutically acceptable salts and individual diastereomers thereof.

It is to be understood that where one or more of the above recited structures or substructures recite multiple substituents having the same designation each such variable may be the same or different from each similarly designated variable. For example, $R^2$ is recited four times in Formula I, and each $R^2$ in Formula I may independently be any of the substructures defined under $R^2$. The invention is not limited to structures and substructures wherein each $R^2$ must be the same for a given structure. The same is true with respect to any variable appearing multiple time in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue.

The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10}$ and $R^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, such that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, inmidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_p C_{1-3}$ alkyl" this means that when there is one carbon, there are 2(1)+1=3 fluorines. When there are two carbons, there are 2(2)+1=5 fluorines, and when there are three carbons there are 2(3)=1=7 fluorines.

When variables G and J are presented or depicted as "G-J" this indicates that G and J together represent a particular moiety. G-J may represent a single ring atom or various arrangements of multiple ring atoms. For instance, G-J is at times herein defined as the single ring atom N, and is at other times defined as multiple ring atoms $C=C(R^5)$, $C=N$, and so forth.

Similarly, when variables Q, T, U and V are presented or depicted as "Q-T-U-V" this indicates that these variables together represent a particular moiety. Here, Q-T-U-V may represent various arrangements of multiple ring atoms, for instance N=C($R^6$)—C($R^6$)=C($R^6$), C($R^6$)=N—C($R^6$)=C($R^6$) and C($R^6$)=C($R^6$)—N=C($R^6$), among others.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 3944). Briefly, membranes (25 μg) were incubated in 1 mL of binding buffer [10 mM HEPES, pH 7.4, 5 mM $MgCl_2$ and 0.2% bovine serum albumin (BSA)] containing 10 pM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 μL) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/mL penicillin and 100 μg/ml streptomycin at 37° C., 95% humidity, and 5% $CO_2$. For cAMP assays, cells were plated at $5 \times 10^5$ cells/well in 96-well poly-D-lysine-coated plates (Becton-Dickinson) and cultured for ~18 h before assay. Cells were washed with phosphate-buffered saline (PBS, Sigma) then pre-incubated with 300 μM isobutylmethylxanthine in serum-free MEM for 30 min at 37° C. Antagonist was added and the cells were incubated for 10 min before the addition of CGRP. The incubation was continued for another 4 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 μL glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 cm² flasks. CRLR and RAMP1 expression constructs were co-transfected in equal amounts. Twenty-four hours after transfection the cells were split 1:5 and selective medium (growth medium+300 ug/mL hygromycin and 1 ug/mL puromycin) was added the following day. A clonal cell line was generated by single cell deposition utilizing a FACS Vantage SE (Becton Dickinson). Growth medium was adjusted to 150 ug/ml hygromycin and 0.5 ug/mL puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 mL binding buffer (10 mM HEPES, pH 7.4, 5 mM $MgCl_2$, and 0.2% BSA) for 3 hours at room temperature containing 10 pM $^{125}$I-hCGRP (Amersham Biosciences) and inhibitor. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{(Y_{max} - Y_{min})(\% I_{max} - \% I_{min}/100) + Y_{min} + (Y_{max} - Y_{min})(100 - \% I_{max}/100)}{1 + ([Drug]/K_i(1 + [Radiolabel]/K_d)^{nH}}$$

Where Y is observed CPM bound, Ymax is total bound counts, Y min is non specific bound counts, (Y max−Y min) is specific bound counts, % I max is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 uM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 μM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; encephalitis; brain trauma; epilepsy; neurodegenerative diseases; skin diseases; neurogenic cutaneous redness, skin rosaceousness and erythema; tinnitus; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-inflammatory or analgesic agent or an anti-migraine agent, such as an ergotamine or 5-$HT_1$ agonists, especially a 5-$HT_{1B/1D}$ agonist, for example sumatriptan, naratriptan, zolmitriptan, eletriptan, almotriptan, frovatriptan, donitriptan, and rizatriptan; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as aspirin, ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or a steroidal analgesic. Similarly, the instant compounds may be administered with a pain reliever such as acetaminophen, phenacetin, codeine, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; a tricyclic antidepressant, for example amitriptyline, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with ergot alkaloids, for example ergotamine, ergonovine, ergonovine, methylergonovine, metergoline, ergoloid mesylates, dihydroergotamine, dihydroergocornine, dihydroergocristine, dihydroergocryptine, dihydro-I-ergocryptine, dihydro-θ-ergocryptine, ergotoxine, ergocornine, ergocristine, ergocryptine, I-ergocryptine, θ-ergocryptine, ergosine, ergostane, bromocriptine, or methysergide.

Additionally, the present compounds may be used in conjunction with a beta-adrenergic antagonist such as timolol, propanolol, atenolol, or nadolol, and the like; a MAO inhibitor, for example phenelzine; a calcium channel blocker, for example flunarizine, nimodipine, lomerizine, verapamil, nifedipine, prochlorperazine or gabapentin; neuroleptics such as olanzapine and quetiapine; an anticonvulsant such as topiramate, zonisamide, tonabersat, carabersat or divalproex sodium; an angiotensin II antagonist, for example losartan and candesartan cilexetil; an angiotensin converting enzyme inhibitor such as lisinopril; or botulinum toxin type A.

The present compounds may be used in conjunction with a potentiator such as caffeine, an H2-antagonist, simethicone, aluminum or magnesium hydroxide; a decongestant such as phenylephrine, phenylpropanolamine, pseudoephedrine, oxymetazoline, epinephrine, naphazoline, xylometazoline, propylhexedrine, or levo-desoxy-ephedrine; an antitussive such as codeine, hydrocodone, caramiphen, carbetapentane, or dextromethorphan; a diuretic; a prokinetic agent such as metoclopramide or domperidone, and a sedating or non-sedating antihistamine.

In a particularly preferred embodiment the present compounds are used in conjunction with an anti-migraine agent, such as: an ergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan and rizatriptan; and a cyclooxygenase inhibitor, such as a selective cyclooxygenase-2 inhibitor, in particular, rofecoxib, etoricoxib, celecoxib, meloxicam, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of intermediates and final compounds may be conducted as described in Schemes 1-16.

Reaction Schemes

The preparation of final compounds proceeds through intermediates such as those of Formula III and Formula IV, and representative syntheses are described herein.

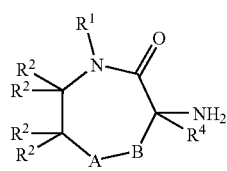
III

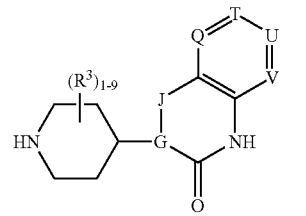
IV

In general, intermediates of the Formulae III and IV can be coupled through a urea linkage as shown in Scheme 1. Amine intermediate 1 can be converted to a reactive carbamate, for example p-nitrophenylcarbamate 2, which is subsequently reacted with an amine like that of intermediate 3 to produce urea 4. Other activated intermediates known to those skilled in the art can be used to prepare compounds like 4. For example, amine 1 can be directly acylated with the appropriate carbamoyl chloride.

SCHEME 1

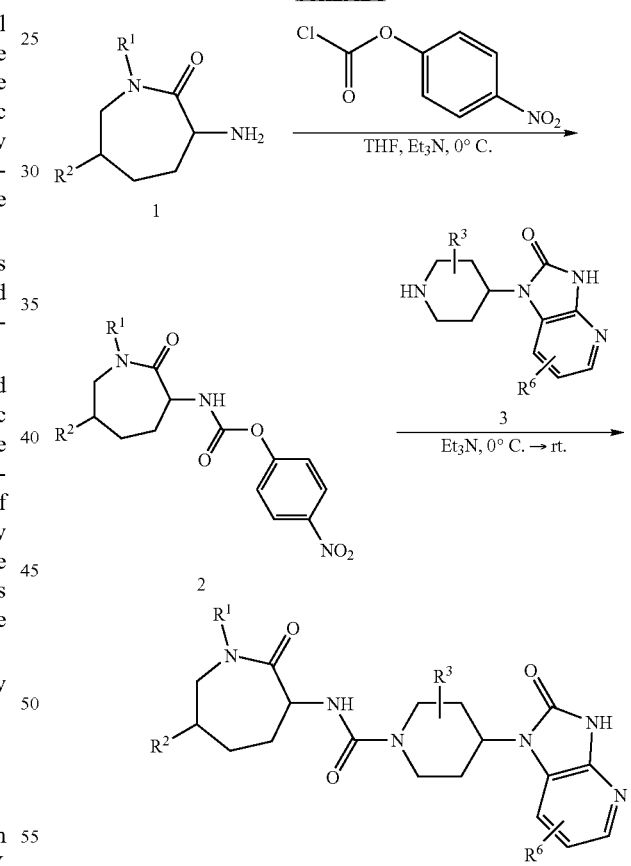

The synthesis of compounds represented by Intermediate IV can be accomplished by procedures similar to those described in Henning et al., J. Med. Chem., 1987, 30, 814-819; Carpino et al., WO 96/35713; Brown et al., J. Chem. Soc. 1957, 682-686; Barlin et al., Aust. J. Chem. 1982, 35 (11), 2299-2306; and references cited therein.

Additionally, the synthesis of compounds represented by Intermediate IV can be accomplished according to Schemes 2-6. For example, a diamino heterocycle, such as 2,3-diaminopyridine 5, can be reductively alkylated with ketones such as 6 to give the monalkylated product 7 (Scheme 2). Ring closure with carbonyldiimidazole furnishes imidazolone 8. Final deprotection under standard conditions gives the intermediate 9.

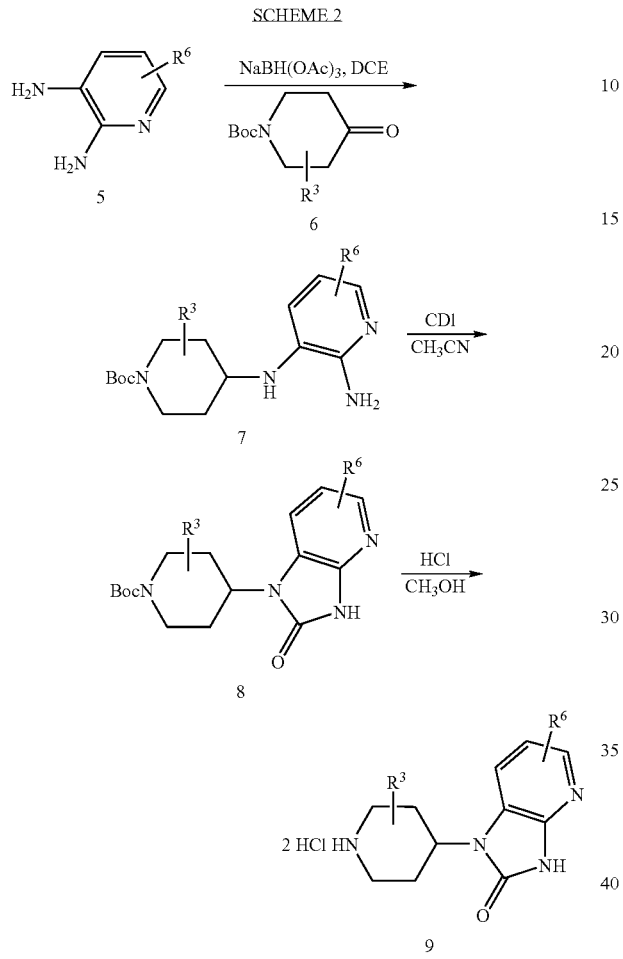

Alternatively, as described in Scheme 3, a suitably protected 4-ketopiperidine like 10 can be reductively alkylated with the appropriate α-amino ester, for example by allylglycine methyl ester (11, $R^6$=H), which then would furnish 12. Treatment with trimethylsilyl isocyanate yields hydantoin 13. Oxidative cleavage of the terminal double bond can be accomplished under standard conditions to afford aldehyde 14, which can be cyclized in the presence of hydrazine in warm acetic acid to deliver 15. Removal of the protecting group gives compounds like 16.

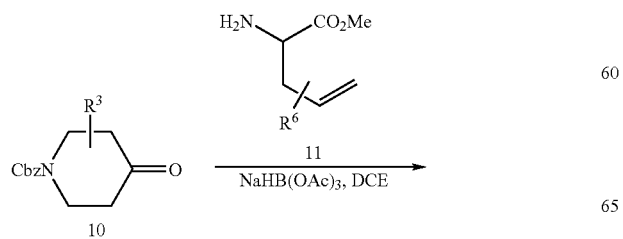

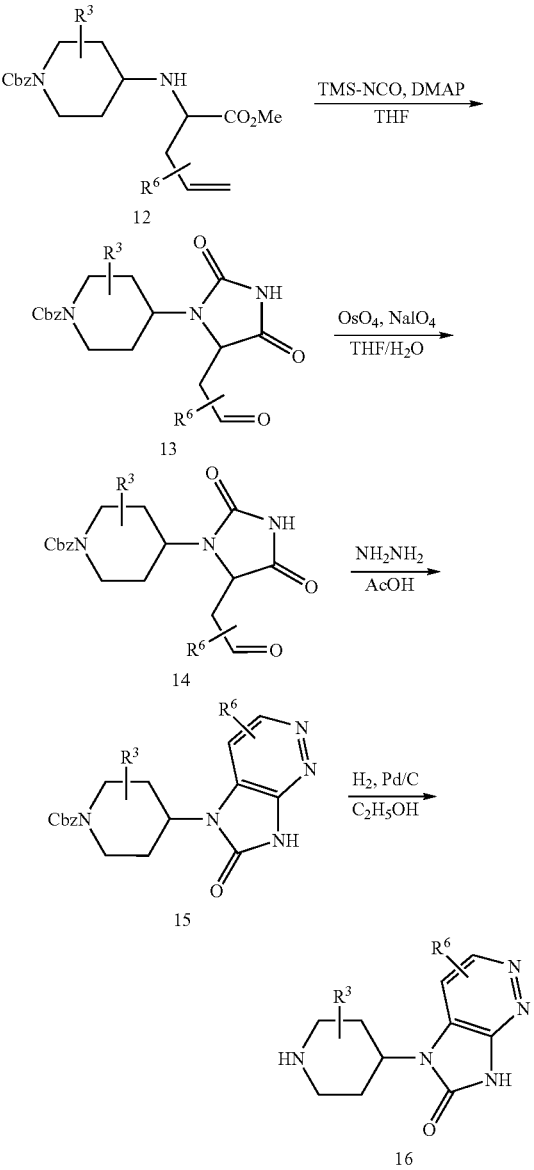

In Scheme 4, a suitably protected 4-aminopiperidine 17 can be arylated by a SNAr reaction, for example using methyl 2-bromopyrazine-3-carboxylate. The resulting product 18 can be converted to an acyl azide via acyl hydrazide 19. Thermal rearrangement of the acyl azide (Curtius rearrangement) can occur with concomitant ring closure to produce 20. Final deprotection under standard conditions gives the desired heterocycles 21.

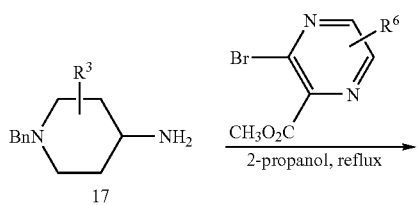

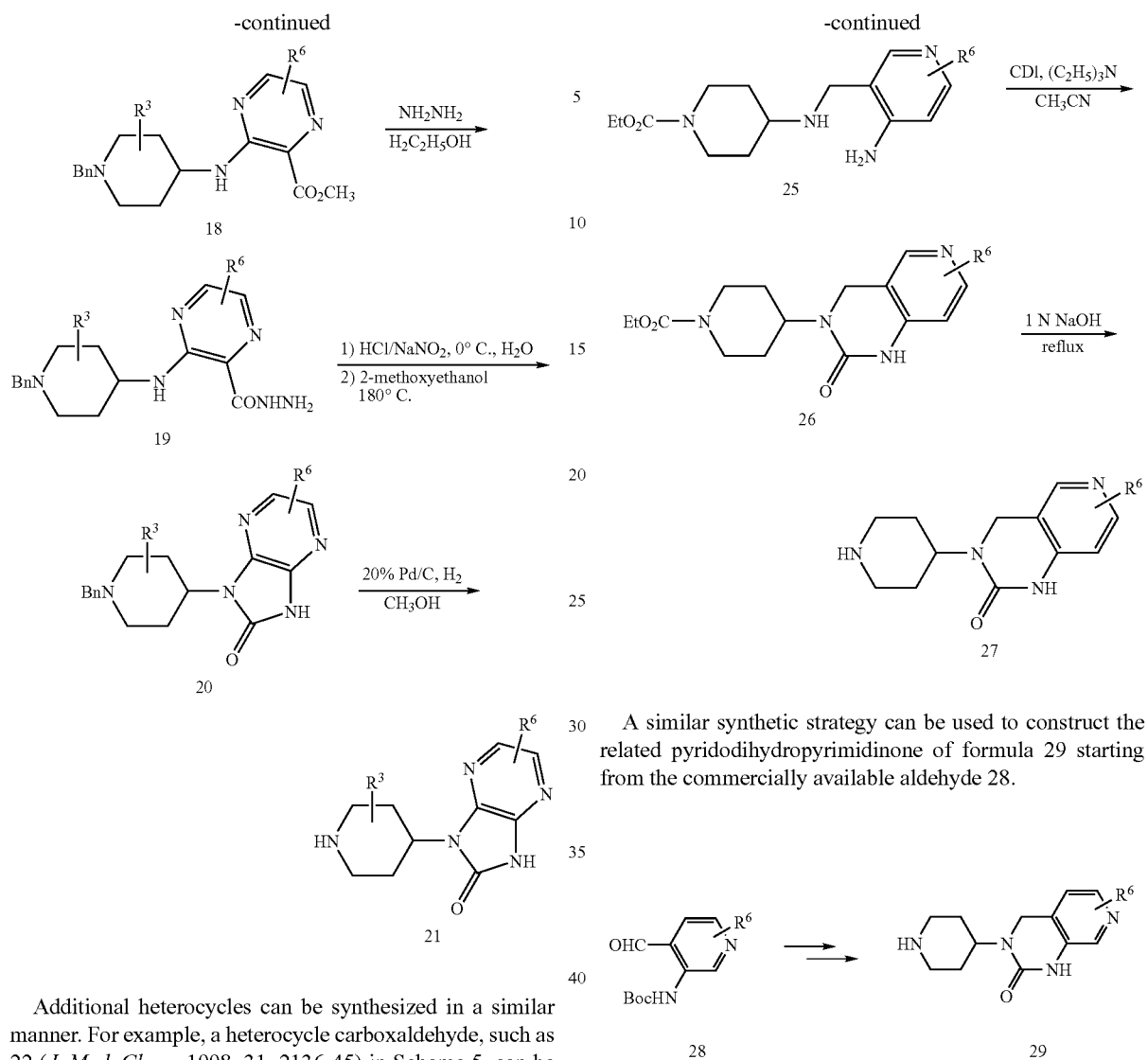

Additional heterocycles can be synthesized in a similar manner. For example, a heterocycle carboxaldehyde, such as 22 (*J. Med. Chem.* 1998, 31, 2136-45) in Scheme 5, can be reductively aminated with amines such as 23 to give the monoalkylated product 24. Deprotection with acid and ring closure with carbonyldiimidazole furnishes pyridodihydropyrimidinone 26. Final deprotection under standard basic conditions gives the product 27.

A similar synthetic strategy can be used to construct the related pyridodihydropyrimidinone of formula 29 starting from the commercially available aldehyde 28.

Alternatively, addition of a suitably protected amine, such as 31, to the commercially available chloropyridine 30, followed by nitrile reduction affords the diamine 33 (Scheme 6). This diamino heterocycle can be reductively alkylated with ketones such as 6 to give the monoalkylated product 34. Ring closure with carbonyldiimidazole furnishes pyridodihydropyrimidinone 35. Final deprotection with trifluoroacetic acid gives the product 36.

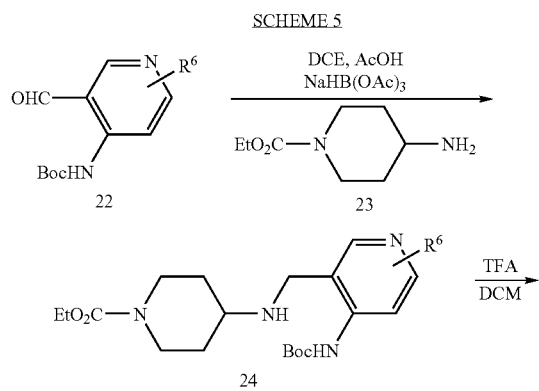

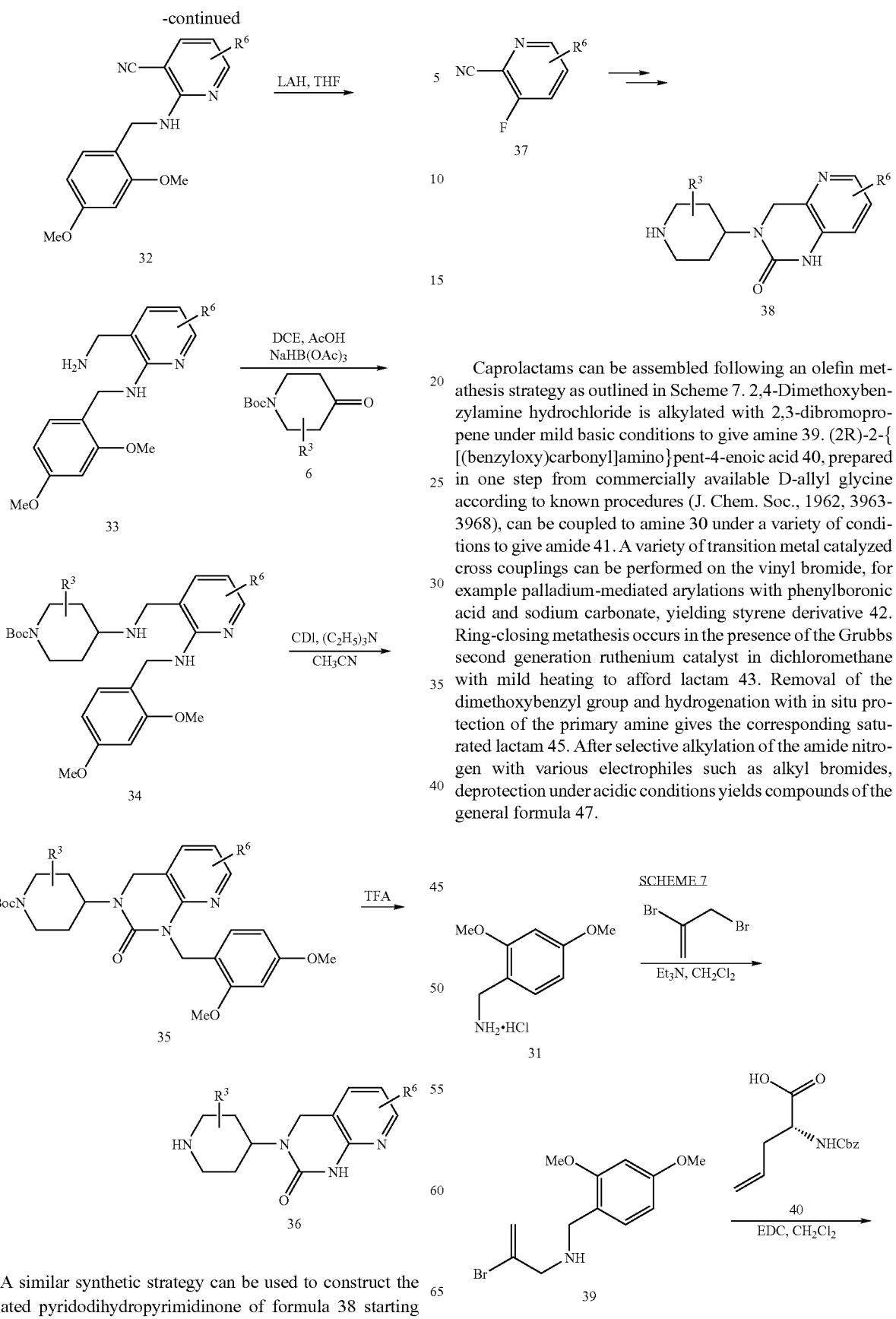

Caprolactams can be assembled following an olefin metathesis strategy as outlined in Scheme 7. 2,4-Dimethoxybenzylamine hydrochloride is alkylated with 2,3-dibromopropene under mild basic conditions to give amine 39. (2R)-2-{[(benzyloxy)carbonyl]amino}pent-4-enoic acid 40, prepared in one step from commercially available D-allyl glycine according to known procedures (J. Chem. Soc., 1962, 3963-3968), can be coupled to amine 30 under a variety of conditions to give amide 41. A variety of transition metal catalyzed cross couplings can be performed on the vinyl bromide, for example palladium-mediated arylations with phenylboronic acid and sodium carbonate, yielding styrene derivative 42. Ring-closing metathesis occurs in the presence of the Grubbs second generation ruthenium catalyst in dichloromethane with mild heating to afford lactam 43. Removal of the dimethoxybenzyl group and hydrogenation with in situ protection of the primary amine gives the corresponding saturated lactam 45. After selective alkylation of the amide nitrogen with various electrophiles such as alkyl bromides, deprotection under acidic conditions yields compounds of the general formula 47.

A similar synthetic strategy can be used to construct the related pyridodihydropyrimidinone of formula 38 starting from the known nitrile 37.

-continued

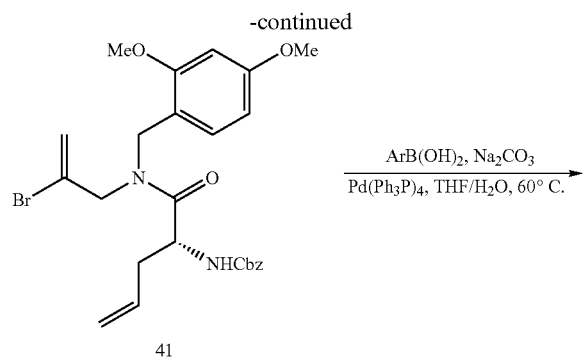
41

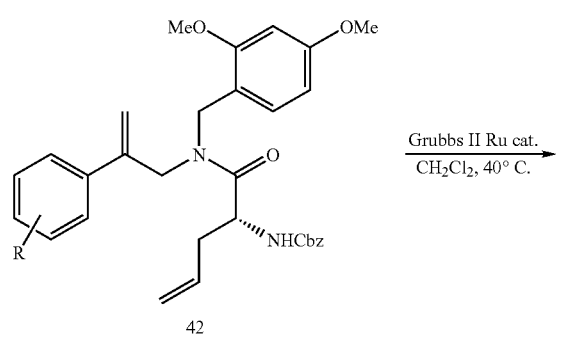
42

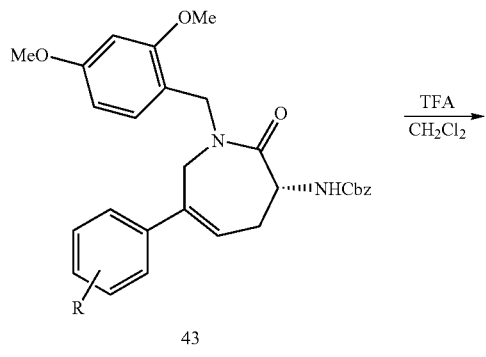
43

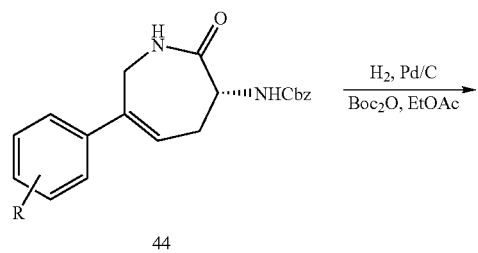
44

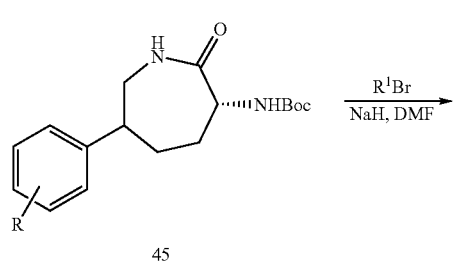
45

-continued

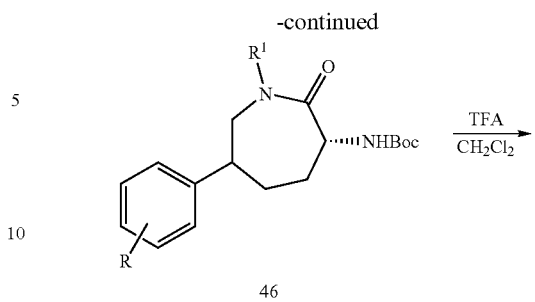
46

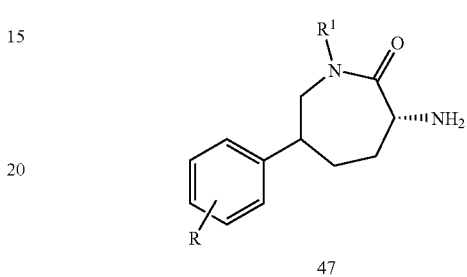
47

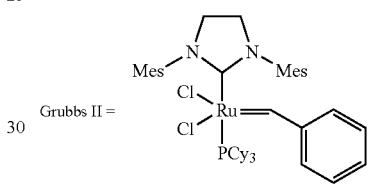
Grubbs II =

Alternatively, a C6-aryl group can be introduced as outlined in Scheme 8. Addition of nitromethane to the known glutamic acid derived aldehyde 48 (*Tetrahedron Asymmetry*, 1998, 3381-94), followed by in situ elimination affords nitro olefin 49. Addition of the aryl group via a boronic acid derivative, or similar equivalent, can be accomplished in a stereoselective manner through chiral ligand-Rh catalysis. Concomitant nitro reduction and benzyl ester hydrogenolysis affords the amino acid 51. Ring closure under standard conditions, followed by removal of a single tert-butoxycarbonyl group furnishes the lactam 45. Intermediates such as 51 can be further processed as in Scheme 9.

SCHEME 8

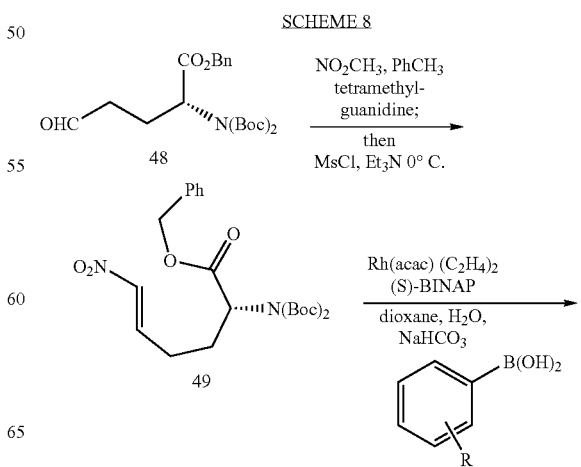

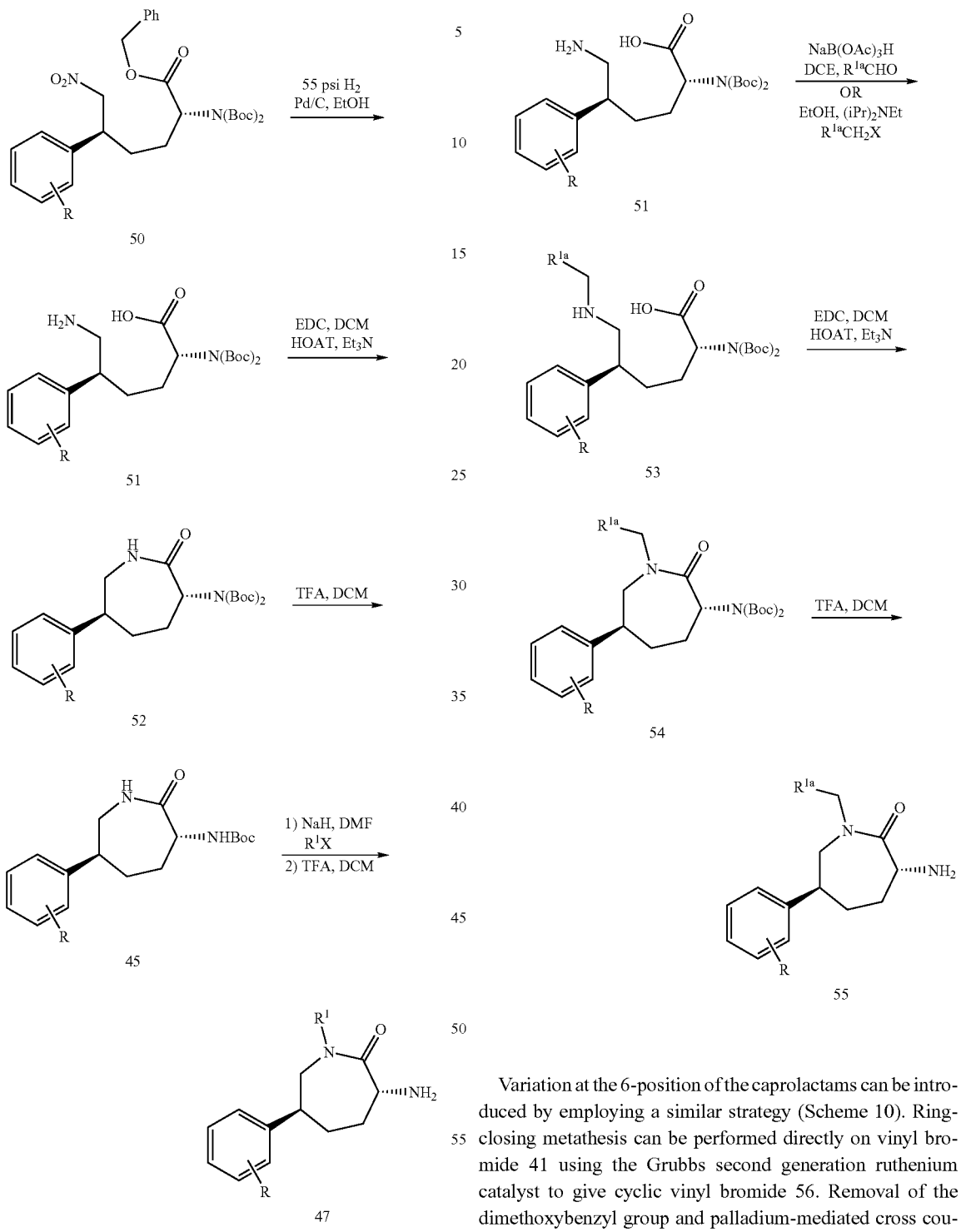

Alternatively, amino acid 51 can be alkylated, either reductively or via an $S_N2$ displacement, to afford intermediates such as 53 (Scheme 9). Ring closure under standard conditions, followed by protecting group removal furnishes the lactam 55.

Variation at the 6-position of the caprolactams can be introduced by employing a similar strategy (Scheme 10). Ring-closing metathesis can be performed directly on vinyl bromide 41 using the Grubbs second generation ruthenium catalyst to give cyclic vinyl bromide 56. Removal of the dimethoxybenzyl group and palladium-mediated cross coupling, in this case with a boronic acid, furnishes compounds of the general formula 58. The transformation of 57 to 58 is not limited to boronic acid derivatives. After standard hydrogenation, the amide nitrogen can be selectively alkylated with various electrophiles, for example alkyl bromides, using sodium hydride as base. Deprotection yields lactams of the general formula 61.

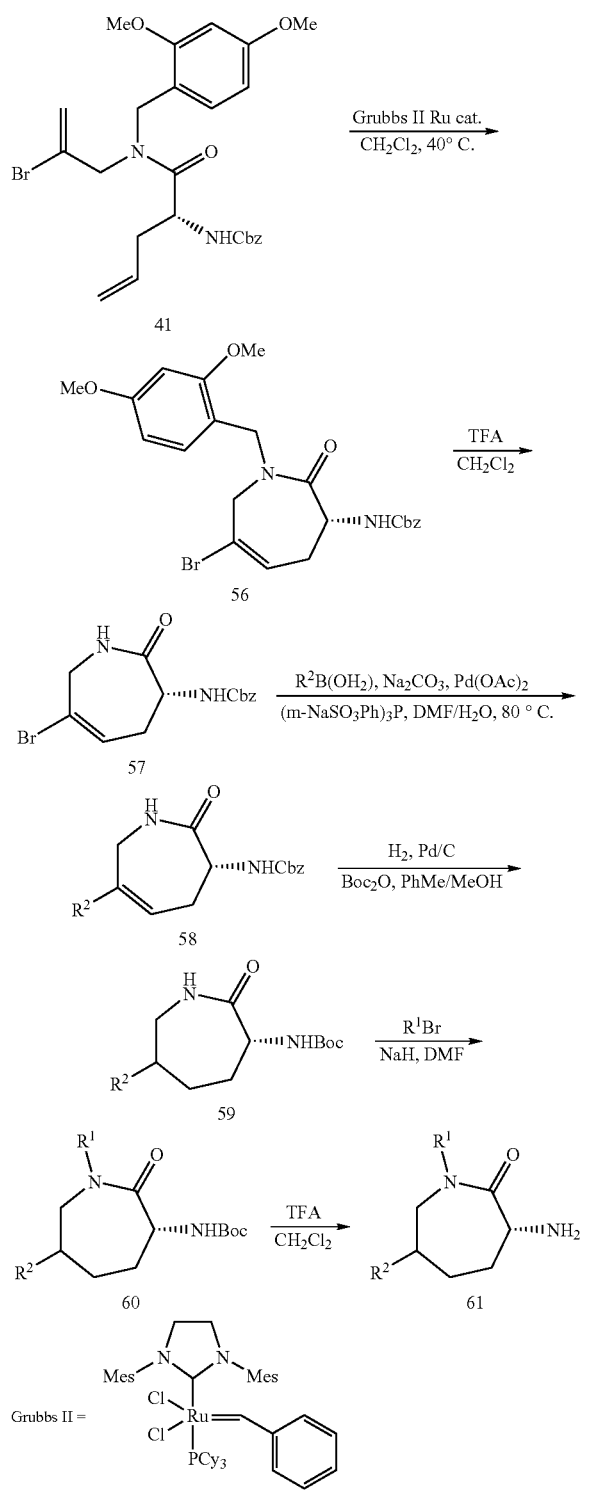

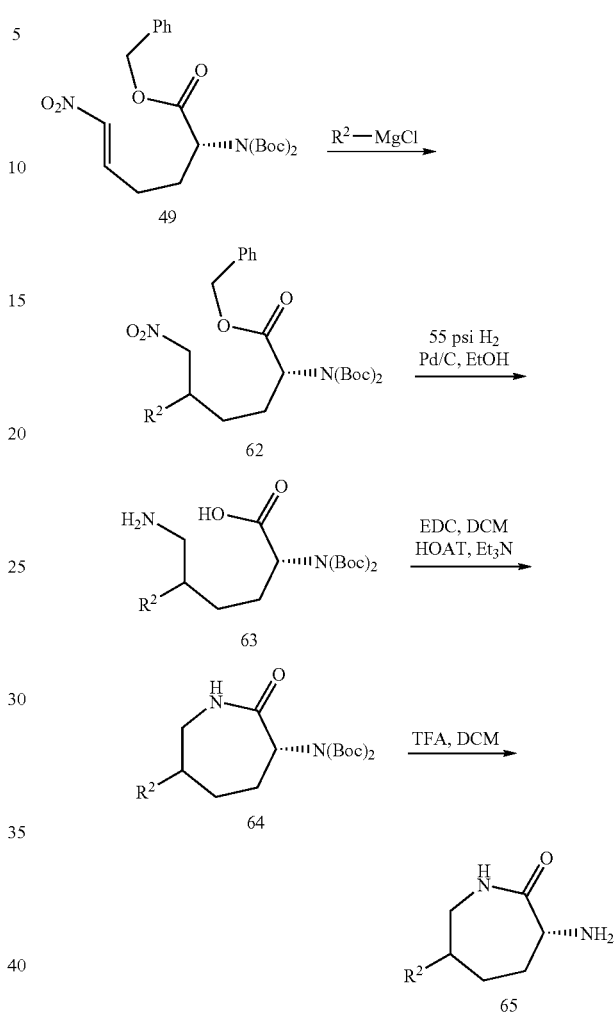

Alternatively, addition of a Grignard or similar reagent, to the nitro olefin 49, followed by nitro reduction and benzyl ester hydrogenolysis affords various amino acids such as 63 (Scheme 11). Ring closure with EDC furnishes caprolactam 64. Final deprotection with trifluoroacetic acid gives the product 65.

The C7-position of the caprolactam can be varied as outlined in Scheme 12. Addition of the nitroalkane to an aldehyde $R^2CHO$, affords an alcohol such as 66. Concomitant nitro reduction and benzyl ester hydrogenolysis affords the amino acid 67. Ring closure under standard conditions, followed by removal of the tert-butoxycarbonyl groups furnishes the lactam 69.

SCHEME 12

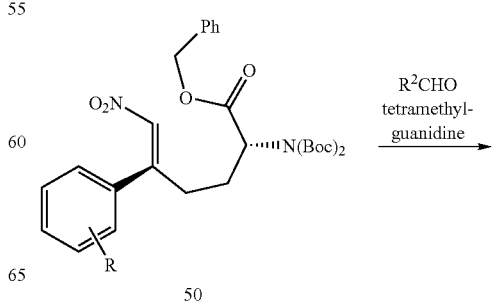

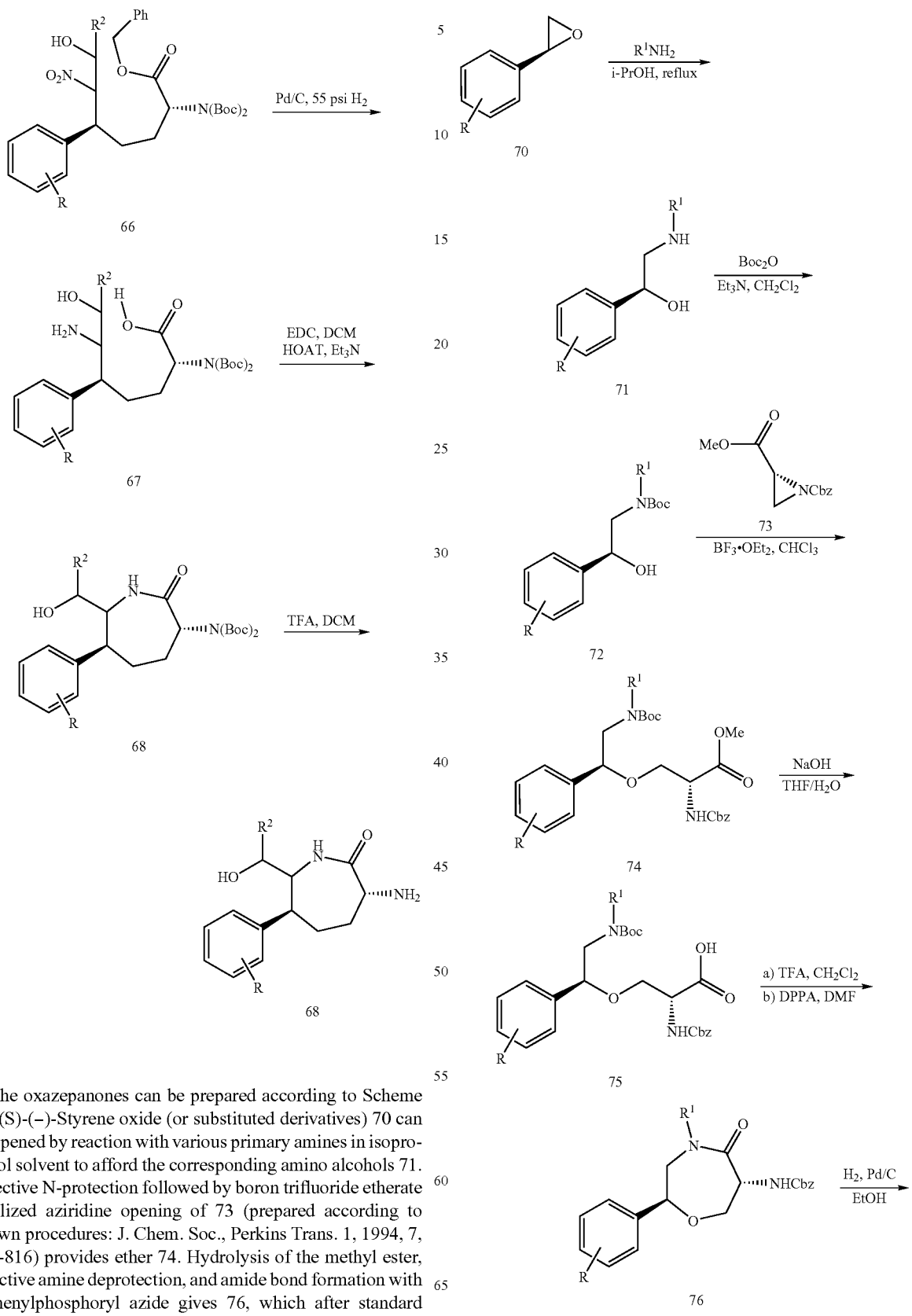

The oxazepanones can be prepared according to Scheme 13. (S)-(−)-Styrene oxide (or substituted derivatives) 70 can be opened by reaction with various primary amines in isopropanol solvent to afford the corresponding amino alcohols 71. Selective N-protection followed by boron trifluoride etherate catalized aziridine opening of 73 (prepared according to known procedures: J. Chem. Soc., Perkins Trans. 1, 1994, 7, 807-816) provides ether 74. Hydrolysis of the methyl ester, selective amine deprotection, and amide bond formation with diphenylphosphoryl azide gives 76, which after standard hydrogenation conditions yields amine 77.

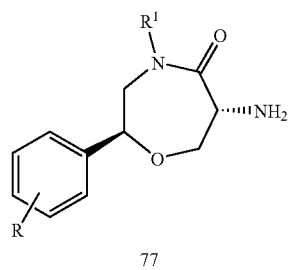

The 3-acetyl caprolactam derivatives can be prepared as outlined in Scheme 14. Lactam 78 (prepared according to known procedures: J. Med. Chem., 1988, 31, 422-428) can be alkylated selectively at the amide nitrogen with a variety of electrophiles, such as alkyl bromides, using sodium hydride as base. C-alkylation is achieved by generation of the enolate with lithium diisopropylamide followed by quenching with tert-butyl bromoacetate, giving ester 79. Deprotection of the carboxyl group is accomplished with trifluoroacetic acid. Coupling of the resultant carboxylic acid with amine 9 under standard conditions affords 3-acetyl lactams of the general formula 82.

SCHEME 14

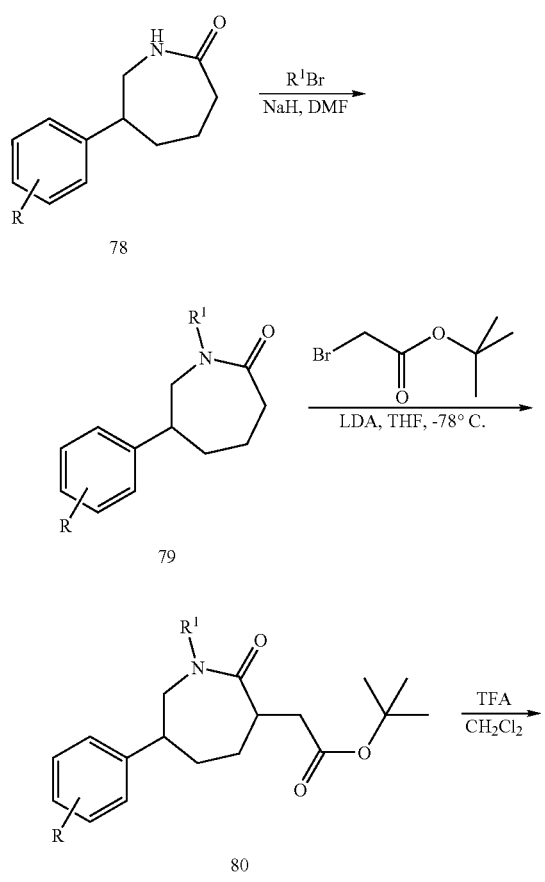

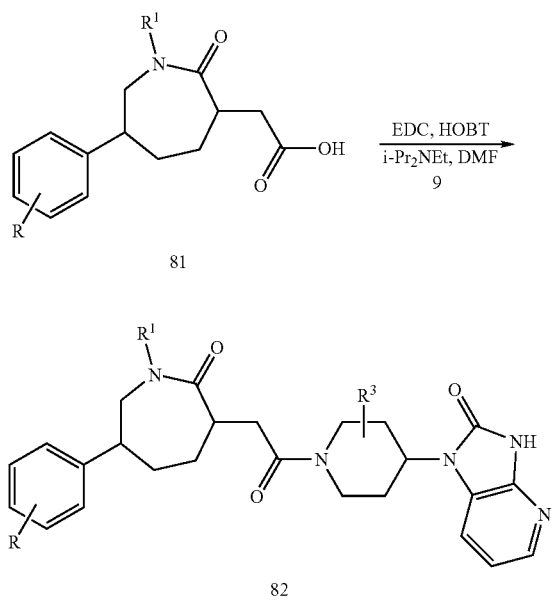

Piperidinones are prepared as outlined in Scheme 15. Commercially available hydroxypyridine 89 can be selectively N-alkylated using various electrophiles with cesium carbonate. Palladium-mediated cross coupling with different aryl, heteroaryl, and alkyl groups affords the substituted pyridinones. Platinum catalyzed hydrogenation at 56 psi results in both reduction of the olefins and the nitro group, giving diastereomeric mixtures of the primary amine 92. Urea formation under standard conditions with the appropriate amine (eg, 9) yields the final targets 93.

SCHEME 15

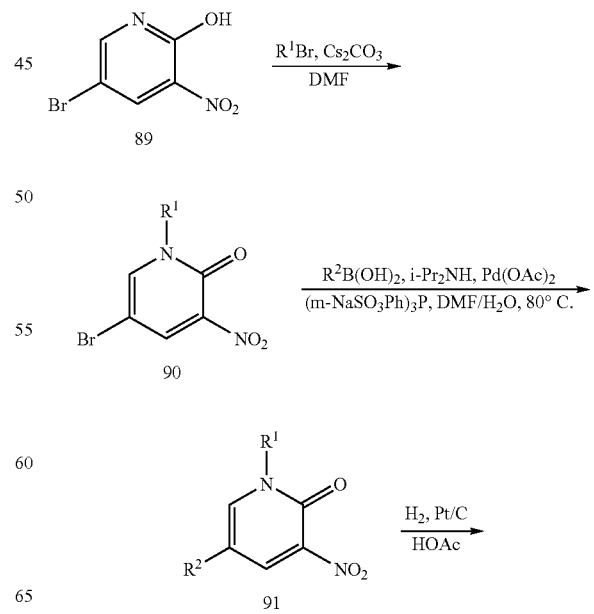

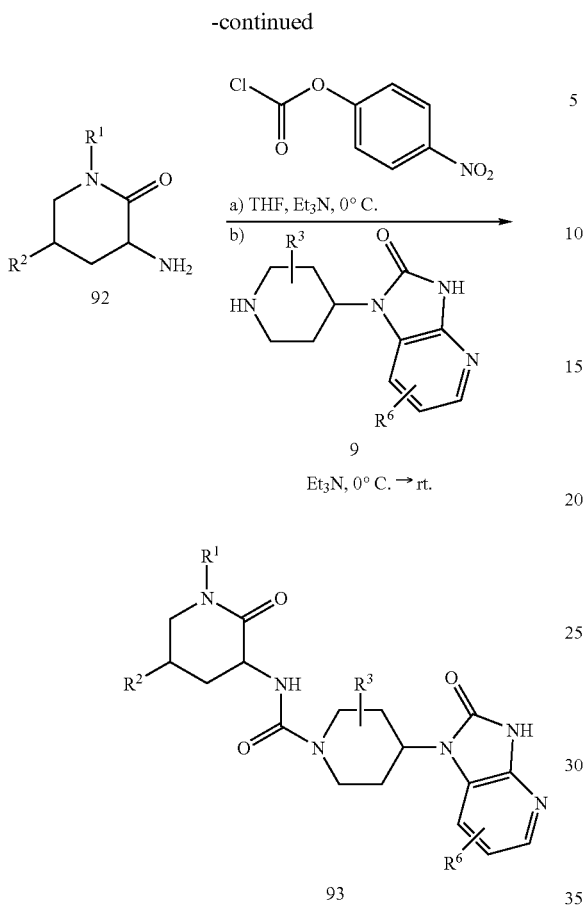

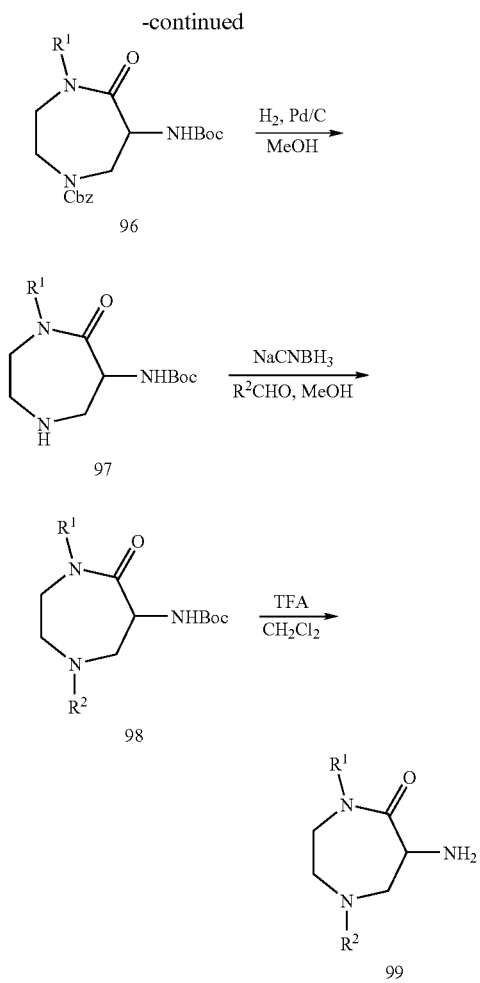

Diazepinone derivatives can be prepared as shown in Scheme 16. Following amine protection of the commercially available diazepinone 94, alkylation of various electrophiles with sodium hydride gives substituted amides 96. Removal of the Cbz group and reductive amination of various aldehydes or alkylation of different halides affords the disubstituted diazepinones, such as 98, and final deprotection of the primary amine with trifluoroacetic acid yields the urea coupling precursor 99.

SCHEME 16

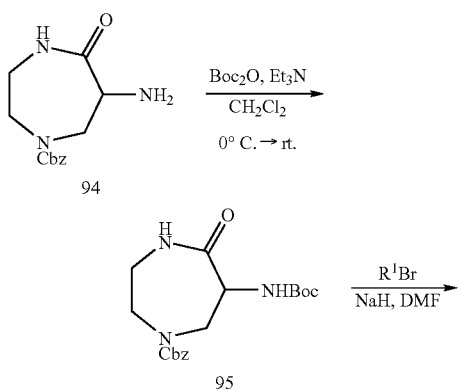

In some cases the final product may be further modified, for example, by manipulation of substituents. These manipulations may include, but are not limited to, reduction, oxidation, alkylation, acylation, and hydrolysis reactions which are commonly known to those skilled in the art. Moreover, in some cases the order of carrying out the foregoing reaction schemes may be varied to facilitate the reaction or to avoid unwanted reaction products.

INTERMEDIATES AND EXAMPLES

The following examples are provided so that the invention might be more fully understood. These examples are illustrative only and should not be construed as limiting the invention in any way.

Intermediate 1

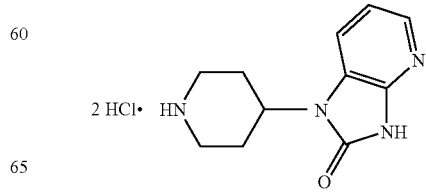

2-Oxo-1-(4-piperidinyl)-2,3-dihydro-1H-imidazo[4,5-b]pyridine dihydrochloride

Step A. 2-Amino-3-[(1-t-butoxycarbonylpiperidin-4-yl)amino)pyridine

Sodium triacetoxyborohydride (14.5 g, 68.7 mmol) was added to a solution of 2,3-diaminopyridine (5.00 g, 45.8 mmol) and N-(t-butoxycarbonyl)-4-piperidone (9.58 g, 48.1 mmol) in dichloroethane (75 mL) at room temperature. After 5 h, additional sodium triacetoxyborohydride was added (1.8 g) and again after another 2.5 h. The reaction was stirred overnight, and quenched with 5% aqueous sodium hydroxide. This was extracted with methylene chloride, and washed with 5% aqueous sodium hydroxide, water and saturated sodium chloride solution. After drying over sodium sulfate, the solution was filtered and evaporated to give the crude product. This was purified by chromatorgraphy (silica gel, 3 to 5% methanol in methylene chloride gradient elution), which gave the title compound (4.44 g). MS 293 (M+1) $^1$H NMR (500 MHz, CD$_3$OD) δ 7.32 (dd, J=1, 5 Hz, 1H), 6.85 (dd, J=1, 8 Hz, 1H), 6.59 (dd, J=5, 8 Hz, 1H), 4.04 (d, J=13 Hz, 2H), 3.46 (m, 1H), 2.98 (br s, 2H), 2.01 (dd, J=2, 12 Hz, 2H), 1.46 (s, 9H), 1.37 (qd, J=4, 12 Hz, 2H).

Step B. 2-Oxo-1-(1-t-butoxycarbonylpiperidin-4-yl)-2,3-dihydro-1H-imidazo[4,5-b]pyridine Carbonyldiimidazole (0.70 g, 4.33 mmol) was added to a solution of 2-amino-3-[(1-t-butoxycarbonylpiperidin-4-yl)amino]pyridine (1.15 g, 3.93 mmol) in acetonitrile (150 mL) at room temperature. After several hours, an additional amount of carbonyldiimidazole was added (0.81 g), and the reaction stirred overnight. The acetonitrile was evaporated in vacuo, the residue partitioned between water and chloroform, and the organic phase washed with saturated brine and dried over magnesium sulfate. The crude product was purified by chromatography (silica gel, 1.2 to 2.5% methanol in methylene chloride gradient elution), which gave the title compound (1.09 g). $^1$H NMR (500 MHz, CDCl$_3$) δ 9.39 (br s, 1H), 8.04 (dd, J=1, 5 Hz, 1H), 7.33 (dd, J=1, 8 Hz, 1H), 6.99 (dd, J=5, 8 Hz, 1H), 4.50 (m, 1H), 4.32 (br s, 2H), 2.86 (br s, 2H), 2.20 (m, 2H), 1.86 (d, J=12 Hz, 2H), 1.50 (s, 9H).

Step C. 2-Oxo-1-(4-piperidinyl)-2,3-dihydro-1H-imidazo[4,5-b]pyridine dihydrochloride 2-Oxo-1-(1-t-butoxycarbonylpiperidin-4-yl)-2,3-dihydro-1H-imidazo[4,5-b]pyridine (1.03 g, 3.23 mmol) was dissolved in methanol (25 mL) and a solution of 2N hydrochloric acid in ether (8 mL) was added at room temperature. After 2 h, the volatiles were removed in vacuo, to give the title compound (0.92 g). MS 219 (M+1). $^1$H NMR (500 MHz, CD$_3$OD) δ 8.01 (dd, J=1, 6 Hz, 1H), 7.83 (d, J=8 Hz, 1H), 7.28 (dd, J=6, 8 Hz, 1H), 4.60 (m, 1H), 3.59 (d, J=12 Hz, 2H), 3.21 (t, J=12 Hz, 2H), 2.70 (dq, J=4, 13 Hz, 2H), 2.12 (d, J=13 Hz, 2H).

Intermediate 1A

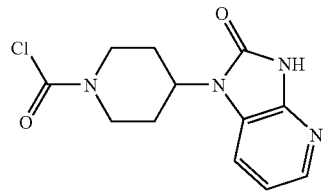

4-(2-Oxo-2,3-dihydro-1H-imidazo[4,5-b]pyridin-1-yl)piperidine-1-carbonyl chloride Phosgene (20% wt. in toluene; 1.8 mL, 3.43 mmol) was added to a suspension of 2-oxo-1-piperidinium-4-yl-2,3-dihydro-1H-imidazo[4,5-b]pyridin-4-ium dichloride (100 mg, 0.343 mmol) and 2,6-lutidine (0.50 mL, 4.293 mmol) in dichloromethane (5 mL) at 0° C. After 2 h, the solution was added to saturated aqueous sodium bicarbonate and extracted with ethyl acetate. The organic layer was washed with water (2×), saturated brine, dried over magnesium sulfate, filtered and concentrated. Dichloromethane (10 mL) was added, and the mixture was filtered to give the title compound as a solid (48 mg). MS 281 (M+1). $^1$H NMR (500 MHz, (CD$_3$)$_2$SO) δ 11.58 (s, 1H), 7.90 (d, J=5.1 Hz, 1H), 7.67 (d, J=7.6 Hz, 1H), 7.01-6.99 (m, 1H), 4.52-4.46 (m, 1H), 4.31-4.23 (m, 2H), 3.38-3.33 (m, 1H), 3.19-3.14 (m, 1H), 2.32-2.24 (m, 2H), 1.84-1.81 (m, 2H).

Intermediate 2

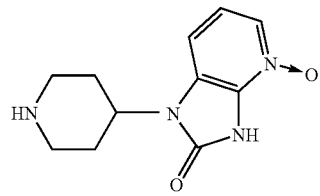

1-Piperidin-4-yl-1,3-dihydro-2H-imidazo[4,5-b]pyridin-2-one 4-oxide

Step A. tert-Butyl 4-(4-oxido-2-oxo-2,3-dihydro-1H-imidazo[4,5-b]pyridin-1-yl)piperidine-1-carboxylate 2-Oxo-1-(1-t-butoxycarbonylpiperidin-4-yl)-2,3-dihydro-1H-imidazo[4,5-b]pyridine (63 mg, 0.198 mmol) was dissolved in 1,2-dichloroethane (10 mL) and 3-chloroperoxybenzoic acid (137 mg, 0.792 mmol) was added at 0° C. The reaction was warmed to room temperature and stirred for 4 h. The reaction was quenched with saturated aqueous sodium bicarbonate and sodium thiosulfate, extracted with methylene chloride (3×), dried over sodium sulfate, filtered and evaporated to give the title compound (45 mg). MS 335.1 (M+1).

Step B. 1-Piperidin-4-yl-1,3-dihydro-2H-imidazo[4,5-b]pyridin-2-one 4-oxide tert-Butyl 4-(4-oxido-2-oxo-2,3-dihydro-1H-imidazo[4,5-b]pyridin-1-yl)piperidine-1-carboxylate (45 mg, 0.135 mmol) was dissolved in dichloromethane (10 mL) and trifluoroacetic acid (5 mL) was added at room temperature. After 3 h, the volatiles were removed in vacuo to give the title compound as its TFA salt. MS 235.2 (M+1).

Intermediate 3

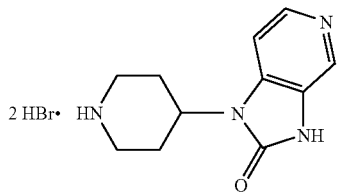

2-Oxo-3-(4-piperidinyl)-2,3-dihydro-1H-imidazo[4,5-c]pyridine dihydrobromide

Step A. Ethyl 4-(pyridin-4-ylamino)piperidine-1-carboxylate

A solution of ethyl 4-aminopiperidine-1-carboxylate (2.20 g, 12.7 mmol), 4-bromopyridine (3.47 g, 17.8 mmol), sodium t-butoxide (4.54 g, 47.2 mmol), 2,2'-bis(diphenylphosphino)-1,1'-binaphthyl (0.398 g, 0.639 mmol) and palladium acetate (0.143 g, 0.639 mmol) in toluene (40 mL) was heated at 60° C. overnight. The reaction was cooled and partitioned between ethyl acetate and water. The aqueous layer was washed 3 times with methylene chloride, and the combined organic layers dried over sodium sulfate. The crude product was purified by chromatography (silica gel, 0 to 10% {5% ammonium hydroxide in methanol} in methylene chloride gradient elution), which gave the title compound (1.3 g, 41% yield).

Step B. Ethyl 4-[(3-nitropyrin-4-yl)amino]piperidine-1-carboxylate

A solution of ethyl 4-(pyridin-4-ylamino)piperidine-1-carboxylate (1.30 g, 5.21 mmol) in 90% sulfuric acid (17 mL) was cooled to 0° C. To this was added 70% nitric acid (1.2 mL) in 90% sulfuric acid (8 mL). The reaction was stirred at 0° C. for 1.5 h, then poured into ice water (150 mL). Solid sodium carbonate was added to render the solution basic. This mixture was extracted four times with methylene chloride, dried, filtered and concentrated. The crude product was purified by chromatography (silica gel, 0 to 10% {5% ammonium hydroxide in methanol} in methylene chloride gradient elution), which gave the title compound (1.09 g, 71% yield).

Step C. Ethyl 4-[(3-aminopyrin-4-yl)amino]piperidine-1-carboxylate

Ethyl 4-[(3-nitropyrin-4-yl)amino]piperidine-1-carboxylate (1.09 g, 3.70 mmol) in ethanol was hydrogenated (1 atm hydrogen) over 30% palladium on carbon (300 mg) for 4 h. The reaction was filtered through celite and concentrated in vacuo, to give the title compound (0.98 g, 100%).

Step D. Ethyl 4-[(2-oxo-2,3-dihydro-1H-imidazol[4,5-c]pyridin-1-yl)piperidine-1-carboxylate A solution of ethyl 4-[(3-aminopyrin-4-yl)amino]piperidine-1-carboxylate (0.98 g, 3.70 mmol) and carbonyldiimidazole (1.80 g, 11.1 mmol) in tetrahydrofuran (40 mL) was refluxed until starting material was consumed. The solvent was removed in vacuo and the crude product purified by chromatography (silica gel, 0 to 10% {5% ammonium hydroxide in methanol} in methylene chloride gradient elution). Fractions containing product were dissolved in methylene chloride and washed with saturated sodium carbonate to remove co-eluting imidazole. The organic phase was dried over sodium sulfate, filtered and concentrated to give the title compound (0.360 g, 33% yield).

Step E. 2-Oxo-1-(4-piperidinyl)-2,3-dihydro-1H-imidazol[4,5-c]pyridine dihydrobromide A solution of ethyl 4-[(2-oxo-2,3-dihydro-1H-imidazo][4,5-c]pyridin-1-yl)piperidine-1-carboxylate (0.120 g, 0.413 mmol) in 30% hydrogen bromide/acetic acid (1 mL) was heated at 70° C. overnight. The reaction was cooled and concentrated in vacuo. The resulting solid was triturated with methylene chloride and dried, giving the title compound (0.123 g, 78% yield). $^1$H NMR (500 MHz, CD$_3$OD) δ 8.48 (d, J=6 Hz, 1H), 8.46 (s, 1H), 7.94 (d, J=6 Hz, 1H), 4.80 (m, 1H), 3.60 (d, J=10 Hz, 2H), 3.30 (m, partially obscured by solvent peak), 2.81 (dq, J=4.12 Hz, 2H), 2.16 (d, J=12 Hz, 2H).

Intermediate 4

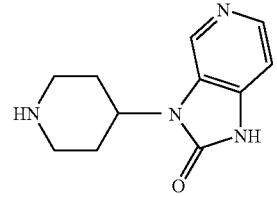

2-Oxo-3-(4-piperidinyl)-2,3-dihydro-1H-imidazo[4,5-c]pyridine

Step A. 4-Amino-3-[(1-benzylpiperidin-4-yl)amino)pyridine

A mixture of 3,4-diaminopyridine (1.1 g, 10.1 mmol), 1-benzyl-4-piperidone (3.2 g, 16.9 mmol) sodium triacetoxyborohydride (4.0 g, 18.9 mmol), and acetic acid (10.7 mL) in dichloroethane (10 mL) was stirred for about 6 days at room temperature. The reaction was concentrated to near dryness, and partitioned between chloroform (5×50 mL) and 1N sodium hydroxide (50 mL). The organic phase was dried over magnesium sulfate and concentrated to give the title compound (2.8 g). MS 283 (M+1).

Step B. 2-Oxo-3-(1-benzylpiperidin-4-yl)-2,3-dihydro-1H-imidazo[4,5-c]pyridine

A solution of 4-amino-3-[(1-benzylpiperidin-4-yl)amino)pyridine (2.8 g, 9.9 mmol) and carbonyldiimidazole (3.0 g, 18.5 mmol) in tetrahydrofuran (100 mL) was refluxed overnight. The reaction was cooled, concentrated and partitioned between chloroform (500 mL) and saturated sodium carbonate (100 mL). The organic phase was dried over magnesium sulfate and concentrated to give the title compound (2.8 g). MS 209 (M+1).

Step C. 2-Oxo-3-(4-piperidinyl)-2,3-dihydro-1H-imidazo[4,5-c]pyridine

A solution of 2-oxo-3-(1-benzylpiperidin-4-yl)-2,3-dihydro-1H-imidazo[4,5-c]pyridine (0.5 g, 1.6 mmol) in methanol (250 mL) was shaken with 20% Pd(OH)$_2$ under a hydrogen atmosphere for 48 h at room temperature. The reaction was filtered and concentrated to give the title compound as a white solid (0.3 g). MS 219 (M+1).

Intermediate 5

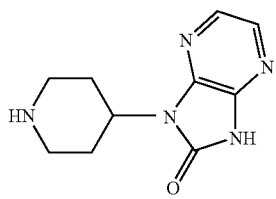

2-Oxo-1-(4-piperidinyl)-2,3-dihydro-1H-imidazo[4,5-b]pyrazine

Step A. Methyl 3-[1-benzylpiperidin-4-yl)amino]pyrazine-2-carboxylate

A mixture of methyl 2-bromopyrazine-3-carboxylate (J. Med. Chem., 1969, 12, 285) (2.2 g, 10.1 mmol) and 4-amino-1-benzylpiperidine (2.0 g, 10.5 mmol) was refluxed in 2-propanol overnight. Thin layer chromatography (10% methanol in ethyl acetate) showed the reaction was complete. The solvent was evaporated, and the crude product dissolved in chloroform (100 mL), which was washed with saturated sodium carbonate solution (20 mL), and dried over magnesium sulfate. The title compound was obtained as a gum (3.8 g). MS 327 (M+1).

Step B. 3-[(1-Benzylpiperidin-4-yl)amino]pyrazine-2-carbohydrazide

A mixture of methyl 3-[(1-benzylpiperidin-4-yl)amino]pyrazine-2-carboxylate (3.0 g, 9.2 mmol) and hydrazine hydrate (6 mL) in ethanol (100 mL) was refluxed with stirring for 2 h. The reaction was cooled and concentrated to give the title compound (3.0 g). MS 327 (M+1).

Step C. 2-Oxo-1-(1-benzylpiperidin-4-yl)-2,3-dihydro-1H-imidazo[4,5-b]pyrazine 3-[(1-Benzylpiperidin-4-yl)amino]pyrazine-2-carbohydrazide (3.0 g, 9.2 mmol) was dissolved in 1N HCl (20 mL) and water (40 mL), and cooled to 0° C. To this was added aqueous sodium nitrite (0.8 g, 11.6 mmol) in water (5 mL). After 0.5 h sodium bicarbonate was added and the basic solution extracted with chloroform (5×50 mL), which was dried over magnesium sulfate. The crude acyl azide was dissolved in methoxyethanol (20 mL) and heated at 180° C. for 3 h. The progress of the reaction was monitored by thin layer chromatography (10% methanol in chloroform). The reaction was cooled and concentrated, and the crude product purified by preparative thin layer chromatography (silica gel, 75:25 tetrahydrofuran:hexane) to give the title compound (1.7 g). MS 310 (M+1).

Step D. 2-Oxo-1-(4-piperidinyl)-2,3-dihydro-1H-imidazo[4,5-b]pyrazine

2-Oxo-1-(1-benzylpiperidin-4-yl)-2,3-dihydro-1H-imidazo[4,5-b]pyrazine (1.7 g, 5.5 mmol) was dissolved in methanol (100 mL) and hydrogenated over 20% palladium on carbon (0.5 g) at 55 psi hydrogen overnight. The catalyst was filtered and solvent evaporated to give the title compound (1.5 g).

Intermediate 6

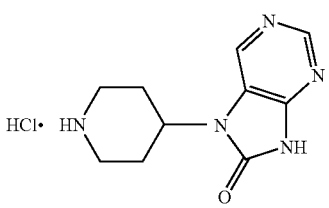

7-Piperidin-4-yl-7,9-dihydro-8H-purin-8-one hydrochloride

Step A. 4-Amino-5-[(1-t-butoxycarbonylpiperidin-4-yl)amino)pyrimidine

A mixture of 4,5-diaminopyrimidine (1.0 g, 9.1 mmol), N-(t-butoxycarbonyl)-4-piperidone (3.0 g, 15 mmol) and sodium triacetoxyborohydride (1.2 g, 5.6 mmol) in dichloroethane (60 mL) was stirred at room temperature for 3 d. The reaction was partitioned between chloroform (200 mL) and 3N sodium hydroxide (30 mL). After drying over magnesium sulfate, the organic phase was concentrated to give the title compound as a tan gum. MS 294 (M+1)

Step B. 7-(1-Benzylpiperidin-4-yl)-7,9-dihydro-8H-purin-8-one

The crude product from Step A, 4-amino-5-[(1-t-butoxycarbonylpiperidin-4-yl)amino)pyrimidine, was refluxed with carbonyldiimidazole (3.0 g, 18 mmol) in tetrahydrofuran (250 mL) for 2 d, cooled and concentrated. The crude product was dissolved in ethyl acetate (25-50 mL), which in four crops gave the title compound as a white crystalline solid (1.3 g). MS 320 (M+1)

Step C. 7-Piperidin-4-yl-7,9-dihydro-8H-purin-8-one hydrochloride

A mixture of 7-(1-benzylpiperidin-4-yl)-7,9-dihydro-8H-purin-8-one (1.2 g, 3.7 mmol) in 4N hydrogen chloride in dioxane (50 mL), was stirred vigorously at room temperature for 3 h. The reaction was concentrated in vacuo to give the title compound as a white solid. MS 220 (M+1)

Intermediate 7

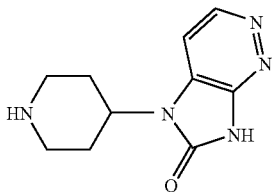

5-Piperidin-4-yl-5,7-dihydro-6H-imidazo[4,5-c]pyridazin-6-one

Step A. Benzyl 4-{[1-(methoxycarbonyl)but-3-en-1-yl]amino}piperidine-1-carboxylate Sodium triacetoxyborohydride (11.2 g, 52.6 mmol) was added to a solution of methyl 2-aminopent-4-enoate (3.4 g, 26.3 mmol), acetic acid (2.37 g, 39.5 mmol) and benzyl 4-oxopiperidine-1-carboxylate (9.21 g, 39.5 mmol) in dichloroethane (60 mL) at room temperature. After 3 h, the reaction was quenched with saturated aqueous sodium bicarbonate, extracted with methylene chloride (3×), dried over sodium sulfate, filtered and evaporated to give the crude product. This was purified by chromatography (silica gel, 0 to 8% methanol in methylene chloride gradient elution), which gave the title compound (9.42 g). MS 347.2 (M+1).

Step B. Benzyl 4-(5-allyl-2,4-dioxoimidazolidin-1-yl)piperidine-1-carboxylate

Trimethylsilyl isocyanate (1.66 g, 14.4 mmol) was added to a solution of benzyl 4-{[1-(methoxycarbonyl)but-3-en-1-yl]amino}piperidine-1-carboxylate (2.00 g, 5.77 mmol) and DMAP (71 mg, 0.57 mmol) in THF (30 mL) at room temperature. The reaction was heated at 50° C. for 48 h. The reaction was quenched with saturated aqueous sodium bicarbonate, extracted with methylene chloride (3×), dried over sodium sulfate, filtered and evaporated to give the crude product. The crude product was purified by chromatography (silica gel, 0 to 20% methanol in methylene chloride gradient elution), which gave the title compound (1.66 g). MS 358.2 (M+1).

Step C. Benzyl 4-(6-oxo-6,7-dihydro-5H-imidazo[4,5-c]pyridazin-5-yl)piperidine-1-carboxylate Benzyl 4-(5-allyl-2,4-dioxoimidazolidin-1-yl)piperidine-1-carboxylate (0.480 g, 1.34 mmol) was dissolved in THF (5 mL), and osmium tetroxide (0.05 mL, 2.5% solution in t-butanol) was added followed by a solution of sodium periodate (0.862 g, 4.03 mmol) in water (4 mL). After 24 h, the reaction was diluted with saturated aqueous $Na_2SO_3$ and $NaHCO_3$ and extracted with ethyl acetate (4×). The combined organic washes were dried over sodium sulfate, filtered and evaporated to give the crude aldehyde (0.352 g). To a portion of this material (0.250 g, 0.696 mmol) in acetic acid (10 mL) was added hydrazine (0.446 mL, 13.9 mmol). This mixture was heated at 50° C. for 24 h, and then concentrated to dryness. Purification by reverse phase HPLC (C-18, 95% water/acetonitrile→5% water/acetonitrile with 0.1% trifluoroacetic acid) gave the product (0.032 g). MS 354.2 (M+1).

Step D. 5-Piperidin-4-yl-5,7-dihydro-6H-imidazo[4,5-c]pyridazin-6-one

A solution of benzyl 4-(6-oxo-6,7-dihydro-5H-imidazo[4,5-c]pyridazin-5-yl)piperidine-1-carboxylate (35 mg, 0.099 mmol) and 10% Pd/C (50 mg) in EtOH (5 mL), was hydrogenated under a balloon overnight. The reaction was filtered through Celite with more EtOH and concentrated to afford the title compound (26 mg). MS 220.2 (M+1).

Intermediate 8

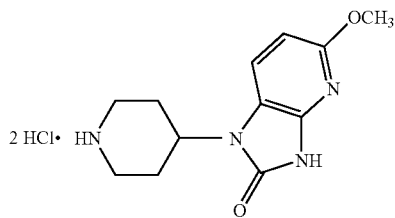

5-Methoxy-2-oxo-1-(4-piperidinyl)-2,3-dihydro-1H-imidazo[4,5-b]yrididne dihydrochloride Step A. 2-Amino-6-chloro-3-nitropyridine A solution of ammonium hydroxide (6.6 g, 0.124 mol) and sodium hydroxide (4.8 g, 0.120 mol) in water (45 mL) was added to 2,6-dichloro-3-nitropyridine (12.0 g, 0.62 mol) in ethanol (240 mL). The reaction was refluxed for 2 h, cooled to room temperature and filtered. The pale yellow solid was dried overnight to give the title compound. $^1$H NMR (500 MHz, $CDCl_3$) δ 8.87 (d, J=9 Hz, 1H), 7.8 (br s, 1H), 6.73 (d, J=9 Hz, 1H), 5.9 (br s, 1H).

Step B. 2-Amino-6-methoxy-3-nitropyridine

Sodium metal (0.5 g, 21.7 mmol) was added portion wise to anhydrous methanol 30 mL) under argon. When the sodium was consumed, 1-amino-6-chloro-3-nitropyridine (3.0 g, 17.2 mmol) and methanol (30 mL) were added, and the suspension refluxed for 2 h. The reaction was cooled to room temperature and stirred for 3 h. The yellow solid was filtered and air dried to give the title compound. MS 170 (M+1) $^1$H NMR (500 MHz, $CDCl_3$) δ 8.29 (d, J=9 Hz, 1H), 7.8 (br s, 1H), 6.14 (d, J=9 Hz, 1H), 5.6 (br s, 1H).

Step C. 2,3-Diamino-6-methoxypyridine

2-Amino-6-methoxy-3-nitropyridine (2.8 g, 16.5 mmol) was dissolved in warm 1:1 methanol/ethanol (200 mL). The solution was cooled, purged with argon, and 10% palladium on carbon was added (0.45 g). Hydrogen was introduced (1 atm) and the reaction stirred until complete. The catalyst was filtered and the solvent evaporated from the filtrate to give the title compound. MS 140 (M+1) $^1$H NMR (500 MHz, $CDCl_3$) δ 6.93 (d, J=8 Hz, 1H), 6.04 (d, J=8 Hz, 1H), 4.15 (br s, 2H), 3.80 (s, 3H), 3.0 (br s, 2H).

Step D. 2-Amino-3-[(1-t-butoxycarbonylpiperidin-4-yl)amino)-6-methoxypyridine

Sodium triacetoxyborohydride (3.39 g, 16.0 mmol) was added to a solution of 2,3-diamino-6-methoxypyridine (2.23 g, 16.0 mmol) and N-(t-butoxycarbonyl)-4-piperidone (7.66 g, 38.4 mmol) in dichloroethane (50 mL) at room temperature. The reaction was quenched with water (50 mL) and stirred overnight, then extracted with chloroform and washed with 5% aqueous sodium hydroxide, water and saturated sodium chloride solution. After drying over sodium sulfate, the solution was filtered and evaporated to give the crude product. This was purified by chromatography, where the more polar product was isolated (silica gel, 50% ethyl acetate hexane, $R_f$=0.36), to give the title compound. MS 323 (M+1). $^1$H NMR (500 MHz, CDCl$_3$) δ 7.99 (d, J=8 Hz, 1H), 6.05 (d, J=8 Hz, 1H), 4.45 (br s), 4.03 (br s), 3.83 (s, 3H), 3.15 (m, 1H), 2.86 (m, 2H), 1.91 (d, J=12 Hz, 2H), 1.5 (br s, 11H), 1.26 (br s, 2H).

Step E. 5-Methoxy-2-oxo-1-(1-t-butoxycarbonylpiperidin-4-yl)-2,3-dihydro-1H-imidazo[4,5-b]pyridine Carbonyldiimidazole (1.6 g, 9.8 mmol) was added to a solution of 2-amino-3-[(1-t-butoxycarbonylpiperidin-4-yl)amino]-6-methoxypyridine (1.29 g, 4.00 mmol) in acetonitrile (100 mL) at room temperature. The reaction was stirred until all the starting material was consumed. Methanol was added to the reaction and the solution stirred for several hours, then the solvent was evaporated in vacuo. The residue was dissolved in ethyl acetate, washed with water and saturated brine, and then dried over magnesium sulfate. The crude product was purified by chromatography (silica gel, 2.5% to 5% methanol in methylene chloride gradient elution), which gave the title compound. MS 349 (M+1) $^1$H NMR (500 MHz, CDCl$_3$) δ 8.50 (br s, 1H), 7.29 (d, J=8 Hz, 1H), 6.43 (d, J=8 Hz, 1H), 4.46 (m, 1H), 4.31 (br s, 2H), 3.90 (s, 3H), 2.85 (br s, 2H), 2.13 (m, 2H), 1.85 (d, J=12 Hz, 2H), 1.50 (s, 9H).

Step F. 5-Methoxy-2-oxo-1-(4-piperidinyl)-2,3-dihydro-1H-imidazo[4,5-b]pyridine 5-Methoxy-2-oxo-1-(1-t-butoxycarbonylpiperidin-4-yl)-2,3-dihydro-1H-imidazo[4,5-b]pyridine (100 mg, 0.287 mmol) was dissolved in methanol (2.5 mL) and a solution of 2N hydrochloric acid in ether (3 mL) was added at room temperature. After 2 h, the volatiles were removed in vacuo, to give the title compound (61 mg). MS 249.1 (M+1).

Intermediate 9

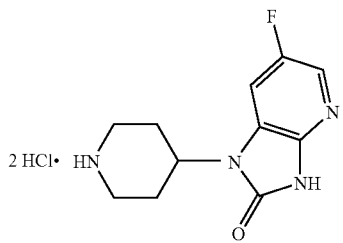

4-Fluoro-2-oxo-1-(4-piperidinyl)-2,3-dihydro-1H-imidazo[4,5-b]pyridine

Step A. N-(5-Fluoropyridin-2-yl)-2,2-dimethylpropanamide

To a 0° C. solution of 2-amino-5-fluoropyridine (1.00 g, 8.92 mmol) and triethylamine (1.35 g, 13.4 mmol) in dichloromethane (30 mL) was added trimethylacetyl chloride (1.29 g, 10.7 mmol) and DMAP (0.11 g, 0.89 mmol). The solution was allowed to warm to room temperature. After 4 h, saturated aqueous NaHCO$_3$ was added, the layers separated and the aqueous phase backwashed with DCM. The combined organics were dried over magnesium sulfate, filtered and concentrated and the residue purified by silica gel chromatography (5%→40% EtOAc/hexanes) to give the title compound (1.34 g). MS197.3 (M+1).

Step B. N-(3-Azido-5-fluoropyridin-2-yl)-2,2-dimethylpropanamide

To a −78° C. solution of N-(5-fluoropyridin-2-yl)-2,2-dimethylpropanamide (1.34 g, 6.83 mmol) in tetrahydrofuran (25 mL) was added tert-butyllithium (1.31 mL of a 1.7 M solution, 20.5 mmol) drop wise. After 3 h at −78° C., 4-dodecylbenzenesulfonyl azide (3.60 g, 10.2 mmol) was added at the reaction was allowed to warm to room temperature. After 1 h, saturated aqueous NH$_4$Cl was added, and the tetrahydrofuran was removed via rotary evaporator. Dichloromethane was added, the layers separated and the aqueous phase backwashed with DCM. The combined organics were dried over magnesium sulfate, filtered and concentrated and the residue purified by two successive silica gel chromatographies (10%→80% EtOAc/hexanes, then 5%→42% EtOAc/hexanes) to give the title compound (0.275 g). MS 234.0 (M+1).

Step C. 3-Azido-5-fluoropyridin-2-amine

N-(3-Azido-5-fluoropyridin-2-yl)-2,2-dimethylpropanamide (275 mg, 1.16 mmol) in 3 N HCl (5 mL) was heated to 100° C. After 2 h, the volatiles were removed in vacuo, to give the title compound as its HCl salt (180 mg). MS154.2 (M+1).

Step D. 5-Fluoropyridine-2,3-diamine

The HCl salt of 3-azido-5-fluoropyridin-2-amine (1.90 g, 10.0 mmol) was dissolved in tetrahydrofuran (100 mL) and treated with MP-Carbonate (Argonaut, 11.5 g). After 1 h, the mixture was filtered, rinsed with more tetrahydrofuran, and concentrated. This residue was dissolved in ethanol (50 mL), purged with argon, and 10% palladium on carbon was added (0.15 g). Hydrogen was introduced (1 atm) and the reaction stirred until complete. The catalyst was filtered and the solvent evaporated from the filtrate to give the title compound (1.18 g). MS 128.0 (M+1)

Step E. tert-Butyl 4-[(2-amino-5-fluoropyridin-3-yl)amino]piperidine-1-carboxylate Sodium triacetoxyborohydride (2.95 g, 13.9 mmol) was added to a solution of 5-fluoropyridine-2,3-diamine (1.18 g, 9.28 mmol), acetic acid (0.56 g, 9.28 mmol) and I-(t-butoxycarbonyl)-4-piperidone (1.85 g, 9.28 mmol) in 1,2-dichloroethane (20 mL) at room temperature. After 1 h, the reaction was quenched with water (20 mL) and extracted with dichloromethane. After drying over sodium sulfate, the solution was filtered and evaporated to give the crude product. This was purified by chromatography, (silica gel, 5%→15% MeOH/DCM; then C-18, 95% water/acetonitrile→5% water/acetonitrile with 0.1% trifluoroacetic acid) to give the title compound (0.73 g). MS 311.2 (M+1).

Step F. tert-Butyl 4-(6-fluoro-2-oxo-2,3-dihydro-1H-imidazo[4,5-b]pyridin-1-yl)piperidine-1-carboxylate Carbonyldiimidazole (1.53 g, 9.41 mmol) was added to a solution of tert-butyl 4-[(2-amino-5-fluoropyridin-3-yl)amino]piperidine-1-carboxylate (0.73 g, 2.35 mmol) in acetonitrile (10 mL) at room temperature. The reaction was stirred until all the starting material was consumed (approximately 2 h) and then the solvent was evaporated in vacuo. The residue was diluted with water, extracted with dichloromethane (3×), dried over magnesium sulfate and then concentrated. The crude product was purified by chromatography (silica gel, 1% to 10% methanol in methylene chloride gradient elution), which gave the title compound (0.309 g). MS 337.2 (M+1)

Step G. 4-Fluoro-2-oxo-1-(4-piperidinyl)-2,3-dihydro-1H-imidazo[4,5-b]pyridine tert-Butyl 4-(6-fluoro-2-oxo-2,3-dihydro-1H-imidazo[4,5-b]pyridin-1-yl)piperidine-1-carboxylate (340 mg, 1.01 mmol) was dissolved in dichloromethane (5 mL) and trifluoroacetic acid (5 mL) was added. After 2 h, the reation was concentrated, diluted with dichlormethane (5 mL) and a solution of 1N hydrochloric acid in 1,4-dioxane (2 mL) was added at room temperature. Concentration afforded the title compound (302 mg). MS 237.2 (M+1) $^1$H NMR (500 MHz, CDODl$_3$) δ 7.92 (br s, 1H), 7.70 (dd, 1H), 4.60 (m, 1H), 3.60 (s, 2H), 3.25 (dd, 2H), 2.70 (m, 2H), 2.10 (d, 2H).

Intermediate 10

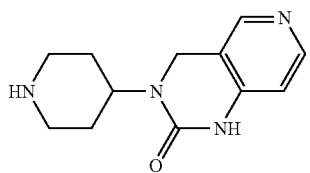

3-Piperidin-4-yl-3,4-dihydropyrido[4,3-d]pyrimidin-2(1H)-one

Step A. Ethyl 4-[({4-[(tert-butoxycarbonyl)amino]pyridin-3-yl}methyl)amino]piperidine-1-carboxylate Sodium triacetoxyborohydride (1.70 g, 8.03 mmol) and acetic acid (0.29, 4.82 mmol) were added to a solution of N-Boc-4-amino-3-pyridine carboxaldehyde (0.36 g, 1.61 mmol) and ethyl 4-aminopiperidine-1-carboxylate (0.33 g, 1.93 mmol) in dichloroethane (5 mL) at room temperature. The reaction was stirred overnight, and quenched with saturated aqueous sodium bicarbonate. This was separated, extracted with ethyl acetate and the combined organics were dried over sodium sulfate. The solution was filtered and evaporated to give the crude product. This was purified by chromatography (silica gel, 0 to 12% methanol in methylene chloride gradient elution), which gave the title compound (0.24 g). MS 379.2.

Step B. Ethyl 4-(2-oxo-1,4-dihydropyrido[4,3-d]pyrimidin-3(2H)-yl)piperidine-1-carboxylate Trifluoroacetic acid (0.50 mL) was a add to a solution of the material from Step A (0.24 g, 0.63 mmol) in dichloromethane (5 mL). After stirring overnight, another 0.5 mL of trifluoroacetic acid was added. After an additional 2 h, the reaction was concentrated. This material was dissolved in acetonitrile (5 mL) and carbonyldiimidazole (0.31 g, 1.89 mmol) was added at room temperature. After 2 h, the acetonitrile was evaporated in vacuo, the residue partitioned between 1N NaOH and dichloromethane, and the organic phase dried over magnesium sulfate. The crude product was purified by chromatography (silica gel, 10 to 15% methanol in methylene chloride gradient elution), which gave the title compound (0.089 g). MS 305.3.

Step C. 3-Piperidin-4-yl-3,4-dihydropyrido[4,3-d]pyrimidin-2(1H)-one

Ethyl 4-(2-oxo-1,4-dihydropyrido[4,3-d]pyrimidin-3(2H)-yl)piperidine-1-carboxylate (0.089 g, 0.29 mmol) was diluted in 1N NaOH (5 mL) and heated to reflux. After 4 h, the reaction was concentrated in vacuo, the residue was diluted with MeOH:DCM, filtered and concentrated. The crude material was purified by reverse phase HPLC (C-18, 5% to 95% 0.1% trifluoroacetic acid/acetonitrile in 0.1% aqueous trifluoroacetic acid gradient elution) to give TFA salt of the title compound (0.12 g). MS 233.3 (M+1).

Intermediate 11

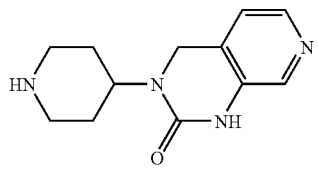

3-Piperidin-4-yl-3,4-dihydropyrido[3,4-d]pyrimidin-2(1H)-one

Step A. Ethyl 4-[({3-[(tert-butoxycarbonyl)amino]pyridin-4-yl}methyl)amino]piperidine-1-carboxylate Sodium triacetoxyborohydride (0.57 g, 2.70 mmol) and acetic acid (0.41, 6.75 mmol) were added to a solution of N-Boc-3-amino-4-pyridine carboxaldehyde (0.50 g, 2.25 mmol) and ethyl 4-aminopiperidine-1-carboxylate (0.47 g, 2.70 mmol) in dichloroethane (5 mL) at room temperature. The reaction was stirred overnight, and quenched with saturated aqueous sodium bicarbonate. This was separated, extracted with ethyl acetate and the combined organics were dried over sodium sulfate. The solution was filtered and evaporated to give the crude product. This was purified by chromatography (silica gel, 1 to 12% methanol in methylene chloride gradient elution), which gave the title compound (0.47 g). MS 379.3.

Step B. Ethyl 4-(2-oxo-1,4-dihydropyrido[3,4-d]pyrimidin-3(2H)-yl)piperidine-1-carboxylate Trifluoroacetic acid (1.43 g) was added to a solution of the material from Step A (0.47 g, 1.24 mmol) in dichloromethane (10 mL). After stirring overnight, the reaction was concentrated. This material was dissolved in acetonitrile (5 mL) and carbonyldiimidazole (0.62 g, 3.73 mmol) was added at room temperature. After 2 d, the acetonitrile was evaporated in vacuo, the residue partitioned between 1N NaOH and dichloromethane, and the organic phase dried over magnesium sulfate. The crude product was purified by chromatography (silica gel, 1 to 20% methanol in methylene chloride gradient elution), which gave the title compound (0.15 g). MS 305.2.

Step C. 3-Piperidin-4-yl-3,4-dihydropyrido[3,4-d]pyrimidin-2(1H)-one

Ethyl 4-(2-oxo-1,4-dihydropyrido[3,4-d]pyrimidin-3(2H)-yl)piperidine-1-carboxylate (0.15 g, 0.48 mmol) was diluted in 1N NaOH (10 mL) and heated to reflux. After 5 h, the reaction was concentrated in vacuo, the residue was diluted with MeOH: DCM, filtered and concentrated. The crude material was purified by reverse phase HPLC (C-18, 5% to 95% 0.1% trifluoroacetic acid/acetonitrile in 0.1% aqueous trifluoroacetic acid gradient elution) to give TFA salt of the title compound (0.17 g). MS 233.3 (M+1).

Intermediate 12

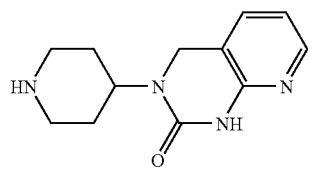

3-Piperidin-4-yl-3,4-dihydropyrido[2,3-d]pyrimidin-2(1H)-one

Step) A.
2-[(2,4-Dimethoxybenzyl)amino]nicotinonitrile 2,4-Dimethoxybenzylamine (2.90 g, 17.3 mmol) and triethylamine (1.75 g, 17.3 mmol) were added sequentially to a solution of 2-chloronicotinonitrile (2.0 g, 14.4 mmol) in N,N-dimethylacetamide (29 mL). The reaction was heated at 80° C. for 4 h, quenched with water and extracted with diethyl ether (3×). The combined organic extracts were washed water, saturated brine, dried over magnesium sulfate and concentrated. The crude product was purified by flash chromatography (silica gel, 0-5% ethyl acetate (with 0.1 triethylamine) in dichloromethane gradient elution) to produce the title compound (2.80 g). MS 270.3 (M+1).

Step B. 3-(Aminomethyl)-N-(2,4-dimethoxybenzyl)pyridin-2-amine

Lithium aluminum hydride (1.0 M in THF, 11.4 mL, 11.4 mmol) was added slowly to a solution of 2-[(2,4-dimethoxybenzyl)amino]nicotinonitrile (2.80 g, 10.4 mmol) in tetrahydrofuran (35 mL) at 0° C. The reaction was allowed to warm to room temperature and stir for 4 h. The reaction was carefully quenched with a saturated aqueous solution of sodium sulfate, filtered with copious dichloromethane and concentrated to produce the title compound (2.92 g). MS 274.3 (M+1).

Step C. tert-Butyl 4-[({2-[(2,4-dimethoxybenzyl)amino]pyridin-3-yl}methyl)amino]piperidine-1-carboxylate Sodium triacetoxyborohydride (0.78 g, 3.66 mmol) and acetic acid (0.22 g, 3.66 mmol) were added to a solution of a portion of the material form Step B (1.00 g, <3.66 mmol) and N-(t-butoxycarbonyl)-4-piperidone (0.73 g, 3.66 mmol) in dichloroethane (20 mL) at room temperature. After 3 h, the reaction was washed with saturated aqueous sodium bicarbonate, dried over sodium sulfate, the solution was filtered and evaporated to give the product (1.83 g). MS 457.3 (M+1).

Step D. tert-Butyl 4-[1-(2,4-dimethoxybenzyl)-2-oxo-1,4-dihydropyrido[2,3-d]pyrimidin-3(2H)-yl]piperidine-1-carboxylate Carbonyldiimidazole (0.65 g, 4.0 mmol) was added to a solution of the material from Step C in dimethylformamide (20 mL) and the reaction was heated to 150° C. After 1 d, further carbonyldiimidazole (0.65 g, 4.0 mmol) was added and the reaction heated for an additional 3 h. The reaction was diluted with water and extracted with dichloromethane, and the organic phase dried over sodium sulfate. The crude product was purified by chromatography (silica gel, 20 to 80% ethyl acetate in methylene chloride gradient elution), which gave the title compound (0.35 g). MS 483.3 (M+1).

Step E. 3-Piperidin-4-yl-3,4-dihydropyrido[2,3-d]pyrimidin-2(1H)-one tert-Butyl 4-[1-(2,4-dimethoxybenzyl)-2-oxo-1,4-dihydropyrido[2,3-d]pyrimidin-3(2H)-yl]piperidine-1-carboxylate (0.21 g, 0.43 mmol) was dissolved in trifluoroacetic acid (5 mL) and stirred overnight. The reaction was then heated to 50° C. for 3 h and concentrated to afford the bisTFA salt of the title compound (0.11 g). MS 233.3 (M+1).

Intermediate 13

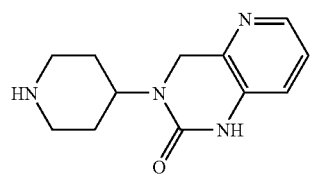

3-Piperidin-4-yl-3,4-dihydropyrido[3,2-d]pyrimidin-2(1H)-one

Step A. 3-[(2,4-Dimethoxybenzyl)amino]pyridine-2-carbonitrile 2,4-Dimethoxybenzylamine (3.29 g, 19.7 mmol) and triethylamine (1.99 g, 19.7 mmol) were added sequentially to a solution of 2-cyano-3-fluoropyridine (2.0 g, 16.4 mmol) (Sakamoto et. al., Chem. Pharm. Bull., 1985, 33, 565-71) in N,N-dimethylacetamide (29 mL). The reaction was heated at 80° C. for 4 h, quenched with water and extracted with diethyl ether (3×). The combined organic extracts were washed water, saturated brine, dried over magnesium sulfate and concentrated. The crude product was purified by flash chromatography (silica gel, 0-12% ethyl acetate (with 0.1 triethylamine) in dichloromethane gradient elution) to produce the title compound (3.25 g). MS 270.3 (M+1).

Step B. 2-(Aminomethyl)-N-(2,4-dimethoxybenzyl)pyridin-3-amine

Lithium aluminum hydride (1.0 M in THF, 13.3 mL, 13.3 mmol) was added slowly to a solution of 3-[(2,4-dimethoxybenzyl)amino]pyridine-2-carbonitrile (3.25 g, 12.1 mmol) in tetrahydrofuran (40 mL) at 0° C. The reaction was warmed to room temperature and stirred for 4 h. The reaction was carefully quenched with a saturated aqueous solution of sodium sulfate, filtered with copious dichloromethane and concentrated to produce the title compound (2.68 g). MS 274.3 (M+1).

Step C. tert-Butyl 4-[({3-[(2,4-dimethoxybenzyl)amino]pyridin-2-yl}methyl)amino]piperidine-1-carboxylate Sodium triacetoxyborohydride (1.16 g, 5.49 mmol) and acetic acid (0.22 g, 3.66 mmol) were added to a solution of a portion of the material form Step B (1.72 g, 3.66 mmol) and N-(t-butoxycarbonyl)-4-piperidone (0.88 g, 4.39 mmol) in dichloroethane (20 mL) at room temperature. After 3 h, the reaction was washed with saturated aqueous sodium bicarbonate, dried over sodium sulfate, the solution was filtered and evaporated to give the product (1.72 g). MS 457.3 (M+1).

Step D. tert-Butyl 4-[1-(2,4-dimethoxybenzyl)-2-oxo-1,4-dihydropyrido[3,2-d]pyrimidin-3(2H)-yl]piperidine-1-carboxylate Carbonyldiimidazole (1.22 g, 7.53 mmol) was added to a solution of the material from Step C in dimethylformamide (20 mL) and the reaction was heated to 150° C. overnight. The reaction was diluted with water and extracted with dichloromethane, and the organic phase dried over sodium sulfate. The crude product was purified by chromatography (silica gel, 30 to 100% ethyl acetate in methylene chloride gradient elution), which gave the title compound (0.10 g). MS 483.3 (M+1).

Step E. 3-Piperidin-4-yl-3,4-dihydropyrido[3,2-d]pyrimidin-2(1H)-one tert-Butyl 4-[1-(2,4-dimethoxybenzyl)-2-oxo-1,4-dihydropyrido[3,2-d]pyrimidin-3(2H)-yl]piperidine-1-carboxylate (0.10 g, 0.21 mmol) was dissolved in trifluoroacetic acid (5 mL) and stirred overnight. The reaction was concentrated to afford the bis-TFA salt of the title compound (0.048 g). MS 233.2 (M+1).

Intermediate 14

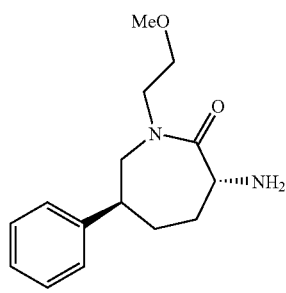

(3R,6S)-3-Amino-1-(2-methoxyethyl)-6-phenylazepan-2-one

Step A: 2-Bromo-N-(2,4-dimethoxybenzyl)prop-2-en-1-amine

Triethylamine (16.0 mL, 114 mmol) was added to a solution of 2,4-dimethoxybenzylamine hydrochloride (11.1 g, 54.5 mmol) and 2,3-dibromopropene (10.9 g, 54.5 mmol) in dichloromethane (200 mL). After 18 h, water was added and the mixture was extracted with dichloromethane (3×). The combined organic extracts were washed with saturated brine, dried over magnesium sulfate, filtered and concentrated. Purification by silica gel chromatography [100% dichloromethane→95% dichloromethane/5% (10% ammonium hydroxide/methanol)] gave the title compound (7.85 g).

Step B: Benzyl (1R)-1-{[(2-bromoprop-2-enyl)(2,4-dimethoxybenzyl)amino]carbonyl}but-3-enylcarbamate 1-[3-(Dimethylamino)propyl]-3-ethylcarbodiimide hydrochloride (55 mg, 0.285 mmol) was added to a solution of 2-bromo-N-(2,4-dimethoxybenzyl)prop-2-en-1-amine (73 mg, 0.256 mmol) and (2R)-2-{[(benzyloxy)carbonyl]amino}pent-4-enoic acid (71 mg, 0.285 mmol) in dichloromethane (5 mL). After 18 h the mixture was concentrated. Purification by silica gel chromatography (5% ethyl acetate/hexanes→30% ethyl acetate/hexanes) gave the title compound (77 mg). MS 517 (M+1).

Step C: Benzyl (1R)-1-{[(2,4-dimethoxybenzyl)(2-phenylprop-2-enyl)amino]carbonyl}but-3-enylcarbamate Tetrakis(triphenylphosphine)palladium(0) (1.11 g, 0.962 mmol) was added to a solution of benzyl (1R)-1-{[(2-bromoprop-2-enyl)(2,4-dimethoxybenzyl)amino]carbonyl}but-3-enylcarbamate (2.49 g, 4.81 mmol), phenylboronic acid (0.65 g, 5.29 mmol) and sodium carbonate (2M in water; 4.81 mL, 9.63 mmol) in tetrahydrofuran (54 mL) and water (20 mL), and the mixture heated to 60° C. After 1 h, the mixture was allowed to cool to ambient temperature and extracted with dichloromethane (3×). The combined organic extracts were washed with saturated brine, dried over magnesium sulfate, filtered and concentrated. Purification by silica gel chromatography (5% ethyl acetate/hexanes→30% ethyl acetate/hexanes) gave the title compound (2.02 g). MS 515 (M+1).

Step D: Benzyl (3R)-1-(2,4-dimethoxybenzyl)-2-oxo-6-phenyl-2,3,4,7-tetrahydro-1H-azepin-3-ylcarbamate

[1,3-bis-(2,4,6-trimethylphenyl-2-imidazolidinylidene)dichloro(phenylmethylene)-(tricyclohexylphosphine)ruthenium] (Grubbs second generation catalyst) (0.68 g, 0.79 mmol) was added to a solution of benzyl (1R)-1-{[(2,4-dimethoxybenzyl)(2-phenylprop-2-enyl)amino]carbonyl}but-3-enylcarbamate (2.02 g, 3.93 mmol) in dichloromethane (395 mL) and heated to 40° C. After 40 h, the mixture was allowed to cool to ambient temperature and concentrated. Purification by silica gel chromatography (5% ethyl acetate/hexanes→30% ethyl acetate/hexanes) gave title compound (1.00 g). MS 487 (M+1). $^1$H NMR (500 MHz, CDCl$_3$) δ7.39-7.31 (m, 5H), 7.26-7.19 (m, 3H), 7.17 (d, J=8.3 Hz, 1H), 6.99 (d, J=7.1 Hz, 2H), 6.41 (dd, J=8.3, 2.0 Hz, 1H), 6.33 (s, 1H), 6.22 (d, J=6.4 Hz, 1H), 5.77-5.76 (m, 1H), 5.16-5.09 (m, 3H), 4.82 (d, J=14.7 Hz, 1H), 4.65 (dd, J=17.6, 2.7 Hz, 1H), 4.54 (d, J=14.4 Hz, 1H), 3.93 (d, J=17.6 Hz, 1H), 3.77 (s, 3H), 3.64 (s, 3H), 2.91-2.86 (m, 1H), 2.42-2.36 (m, 1H).

Step E: Benzyl (3R)-2-oxo-6-phenyl-2,3,4,7-tetrahydro-1H-azepin-3-ylcarbamate A solution of L-methionine (2.56 g, 17.2 mmol) in trifluoroacetic acid (15 mL) was added to a solution of benzyl (3R)-1-(2,4-dimethoxybenzyl)-2-oxo-6-phenyl-2,3,4,7-tetrahydro-1H-azepin-3-ylcarbamate (0.84 g, 1.72 mmol) in dichloromethane (20 mL). After 18 h, the mixture was concentrated and water was added. The mixture was extracted with ethyl acetate, washed with water (2×), saturated aqueous sodium bicarbonate (2×), saturated brine, dried over magnesium sulfate, filtered and concentrated. Purification by silica gel chromatography (5% ethyl acetate/hexanes→50% ethyl acetate/hexanes) gave the title compound (0.44 g). MS 337 (M+1).

Step F: tert-Butyl (3R,6S)-2-oxo-6-phenylazepan-3-ylcarbamate

10% Palladium on carbon (75 mg) was added to a solution of benzyl (3R)-2-oxo-6-phenyl-2,3,4,7-tetrahydro-1H-azepin-3-ylcarbamate (596 mg, 1.77 mmol) and di-tert-butyl dicarbonate (773 mg, 3.54 mmol) in ethyl acetate (30 mL). The reaction vessel is evacuated and back-filled with nitrogen (3×), then back-filled with hydrogen (1 atm). After 2 h, the mixture was filtered and concentrated. Purification by silica gel chromatography (30% ethyl acetate/hexanes→50% ethyl acetate/hexanes) gave the title compound (289 mg).

Step G: tert-Butyl (3R,6S)-1-(2-methoxyethyl)-2-oxo-6-phenylazepan-3-ylcarbamate Sodium hydride (60% dispersion in mineral oil; 6.2 mg, 0.158 mmol) was added to a solution of tert-butyl (3R,6R)-2-oxo-6-phenylazepan-3-ylcarbamate (40 mg, 0.131 mmol) and 2-bromoethyl methyl ether (0.013 mL, 0.138 mmol) in N,N-dimethylformamide (2 mL) at 0° C. After addition, the mixture was allowed to warm to ambient temperature. After 4 h, the reaction was quenched with water and the mixture was extracted with ethyl acetate. The organic layer was washed with water (3×), saturated brine, dried over magnesium sulfate, filtered and concentrated. Purification by silica gel chromatography (5% ethyl acetate/hexanes→30% ethyl acetate/hexanes) gave the title compound (41 mg). MS 363 (M+1).

Step H: (3R,6S)-3-Amino-1-(2-methoxyethyl)-6-phenyl azepan-2-one

Trifluoroacetic acid (2.5 mL) was added to a solution of tert-butyl (3R,6S)-1-(2-methoxyethyl)-2-oxo-6-phenylazepan-3-ylcarbamate (41 mg, 0.113 mmol) in dichloromethane (5 mL). After 1 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated. MS 263 (M+1). $^1$H NMR (500 MHz, CDCl$_3$) δ 7.32 (t, J=7.3 Hz, 2H), 7.25-7.22 (m, 1H), 7.18 (d, J=8.3 Hz, 2H), 3.83-3.76 (m, 3H), 3.56-3.49 (m, 3H), 3.35 (s, 3H), 3.34-3.30 (m, 1H), 2.77-2.72 (m, 1H), 2.13-2.10 (m, 1H), 2.03-1.94 (m, 2H), 1.74-1.68 (m, 1H).

Essentially following the procedures outlined for the preparation of Intermediate 14, the Intermediates in Table I-1 were prepared.

TABLE I-1

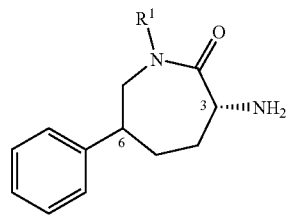

| Intermediate | C-3 | C-6 | R$^1$ | MS (M + 1) |
|---|---|---|---|---|
| 15 | R | S | H | 205 |
| 16 | R | R | H | 205 |
| 17 | R | S | CH$_3$ | 219 |
| 18 | R | S | CH$_2$CH$_3$ | 233 |
| 19 | R | S | CH$_2$CF$_3$ | 287 |
| 20 | R | S | CH$_2$CO$_2$CH$_3$ | 277 |
| 21 | R | S | (CH$_2$)$_2$OCH$_2$CH$_3$ | 277 |
| 22 | R | S | CH$_2$CN | 244 |
| 23 | R | S | cyclopropyl-CH$_2$ | 259 |
| 24 | R | S | 1,3-dioxolan-2-yl-CH$_2$ | 291.1 |
| 25 | R | S | CH$_2$CH$_2$F | 251.1 |
| 26 | R | S | CH$_2$CHF$_2$ | 269.1 |
| 27 | R | S | CH$_2$CHCF$_2$ | 281 |
| 28 | R | S | phenyl-CH$_2$ | 295 |
| 29 | R | S | pyridin-2-yl-CH$_2$ | 296 |
| 30 | R | S | (tetrahydrofuran-2-yl)-CH$_2$ | 289 |
| 31 | R | S | (tetrahydrofuran-2-yl)-CH$_2$ | 289 |
| 32 | R | S | iPrOCH$_2$ | 291 |
| 33 | R | S | MeOCH$_2$CH$_2$ | 277 |
| 34 | R | S | CH$_3$SCH$_2$ | 279 |
| 35 | R | S | CH$_3$SO$_2$CH$_2$ | 311 |
| 36 | R | S | (CH$_2$)$_2$OCF$_3$ | 317 |

TABLE I-1-continued

| Intermediate | C-3 | C-6 | R¹ | MS (M + 1) |
|---|---|---|---|---|
| 37 | R | S | cyclopropylmethoxy-CH₂ | 289 |
| 38 | R | S | (CH₃)(HO)CH-CH₂ | 263.2 |
| 39 | R | S | (tetrahydrofuran-3-yl)-CH₂ | 289 |
| 40 | R | S | (F₃C)(HO)CH-CH₂ | 317.1 |
| 41 | R | S | Ph | 281 |
| 42 | R | S | (CH₃)₂(HO)C-CH₂ | 277.2 |

Intermediate 43

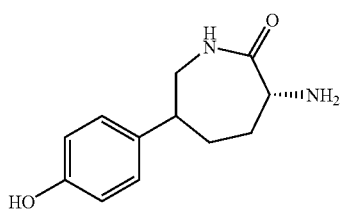

(3R)-3-Amino-6-(4-hydroxyphenyl)azepan-2-one

Step A: Benzyl (3R)-6-bromo-1-(2,4-dimethoxybenzyl)-2-oxo-2,3,4,7-tetrahydro-1H-azepin-3-ylcarbamate

[1,3-bis-(2,4,6-trimethylphenyl-2-imidazolidinylidene) dichloro(phenylmethylene)-(tricyclohexylphosphine)ruthenium] (Grubbs second generation catalyst) (1.78 g, 2.05 mmol) was added to a solution of benzyl (1R)-1-{([(2-bromoprop-2-enyl)(2,4-dimethoxybenzyl) amino] carbonyl}but-3-enylcarbamate (5.29 g, 10.2 mmol) in dichloromethane (1000 mL) and heated to 40° C. After 18 h, the mixture was allowed to cool to ambient temperature and concentrated. Purification by silica gel chromatography (5% ethyl acetate/hexanes→30% ethyl acetate/hexanes) gave the title compound (0.79 g). MS 489 (M+1). ¹H NMR (500 MHz, CDCl₃) δ 7.36-7.35 (m, 4H), 7.33-7.30 (m, 1H), 7.17-7.15 (m, 1H), 6.46-6.43 (m, 2H), 6.13 (d, J=6.1 Hz, 1H), 6.04-6.03 (m, 1H), 5.13-5.07 (m, 2H), 4.93-4.88 (m, 1H), 4.75 (d, J=14.4 Hz, 1H), 4.64-4.60 (m, 1H), 4.47 (d, J=14.4 Hz, 1H), 3.86 (d, J=18.3 Hz, 1H), 3.81 (s, 3H), 3.80 (s, 3H), 2.68-2.63 (m, 1H), 2.24-2.05 (m, 1H).

Step B: Benzyl (3R)-6-bromo-2-oxo-2,3,4,7-tetrahydro-1H-azepin-3-ylcarbamate

A solution of L-methionine (274 mg, 1.84 mmol) in trifluoroacetic acid (5 mL) was added to a solution of benzyl (3R)-6-bromo-1-(2,4-dimethoxybenzyl)-2-oxo-2,3,4,7-tetrahydro-1H-azepin-3-ylcarbamate (90 mg, 0.184 mmol) in dichloromethane (5 mL). After 18 h, the mixture was concentrated. Purification by reverse phase HPLC (C-18, 95% water/acetonitrile→5% water/acetonitrile with 0.1% trifluoroacetic acid) gave the title compound (17 mg). MS 339 (M+1).

Step C: Benzyl (3R)-6-(4-hydroxyphenyl)-2-oxo-2,3,4,7-tetrahydro-1H-azepin-3-ylcarbamate Palladium acetate (1 mg, 0.003 mmol) was added to a solution of benzyl (3R)-6-bromo-2-oxo-2,3,4,7-tetrahydro-1H-azepin-3-ylcarbamate (18 mg, 0.053 mmol), 4-hydroxyphenylboronic acid (9 mg, 0.064 mmol), sodium carbonate (2M in water; 0.066 mL, 0.133 mmol) and trisodium 3-[bis (3-sulfonatophenyl)phosphino]benzenesulfonate (5 mg, 0.088 mmol) in N,N-dimethylformamide (0.45 mL) and water (0.15 mL) and heated to 80° C. After 1.5 h, the mixture was allowed to cool to ambient temperature and filtered. Purification by reverse phase HPLC (C-18, 95% water/acetonitrile→5% water/acetonitrile with 0.1% trifluoroacetic acid) gave the title compound (15 mg). MS 353 (M+1).

Step D: (3R)-3-Amino-6-(4-hydroxyphenyl)azepan-2-one

10% Palladium on carbon (10 mg) was added to a solution of benzyl (3R)-6-(4-hydroxyphenyl)-2-oxo-2,3,4,7-tetrahydro-1H-azepin-3-ylcarbamate (15 mg, 0.043 mmol) in toluene (5 mL) and methanol (1 mL). The reation vessel is evacuated and back-filled with nitrogen (3×), then back-filled with hydrogen (1 atm). After 18 h, the mixture was filtered and concentrated. MS 221 (M+1).

Essentially following the procedures outlined for the preparation of Intermediate 43, the Intermediates in Table I-2 were prepared. Compounds along the route to the Intermediates in Table I-2, can be further processed (e.g. alkylation of N1) according to those skilled in the art following essentially the same procedures as outlined above to afford another set of intermediates.

TABLE I-2

[Structure: azepan-2-one with 3-NH2 and 6-R1, C-3 position marked 3, C-6 position marked 6]

| Intermediate | C-3 | C-6 | R¹ | MS (M + 1) |
|---|---|---|---|---|
| 44 | R | R or S | 2-fluorophenyl | 223.2 |
| 45 | R | R or S | 3-fluorophenyl | 223.2 |
| 46 | R | R or S | 4-fluorophenyl | 223.2 |
| 47 | R | R or S | 2,3-difluorophenyl | 241.2 |
| 48 | R | R or S | pyridin-2-yl | 206.3 |
| 49 | R | R or S | pyridin-3-yl | 206.3 |
| 50 | R | R or S | pyridin-4-yl | 206.2 |
| 51 | R | R or S | 3,5-difluorophenyl | 241.2 |
| 52 | R | R or S | 2,5-difluorophenyl | 241.2 |
| 53 | R | R or S | 2-(trifluoromethyl)phenyl | 273.2 |
| 54 | R | R or S | 2-methylphenyl | 219.2 |
| 55 | R | R or S | 3-methylphenyl | 219.2 |
| 56 | R | R or S | 4-methylphenyl | 219.2 |

Intermediate 57

[Structure: (3R)-3-Amino-6-(2,3-dichlorophenyl)azepan-2-one]

(3R)-3-Amino-6-(2,3-dichlorophenyl)azepan-2-one

Step A. Benzyl (5R or S)—N,N-bis(tert-butoxycarbonyl)-5-(2,3-dichlorophenyl)-6-nitro-D-norleucinate To a slurry of 1-bromo-2,3-dichlorobenzene (1.46 g, 6.46 mmol) in diethyl ether (10 mL) was added magnesium (0.157 g, 6.46 mmol) and a crystal of iodine. This mixture was refluxed for 3 h, and then cooled to room temperature. A solution of benzyl (2R,5E)-2-[bis(tert-butoxycarbonyl)amino]-6-nitrohex-5-enoate (0.50 g, 1.08 mmol) in diethyl ether (10 mL) was cooled to 0° C., and 2.0 mL of the Grignard solution prepared above was added. After 1 and 2 h, respectively, 2.0 and 1.0 mL of the Grignard solution was added. The reaction was quenched with a saturated aqueous solution of ammonium chloride, the phases separated and the organic phase washed with saturated aqueous sodium potassium tartrate and brine. The combined organics were dried over magnesium sulfate, filtered and concentrated to give a residue that was purified by silica gel chromatography (0%→3% methanol/dichloromethane) to give the title compound (0.52 g). MS 411.0 (M+1-2Boc).

Step B. Benzyl $N^2,N^2$-bis(tert-butoxycarbonyl)-5-(2,3-dichlorophenyl)-D-lysinate To an EtOH rinsed (4×5 mL) slurry of Raney Ni (1 mL) was added a solution of benzyl (5R or S)—N,N-bis(tert-butoxycarbonyl)-5-(2,3-dichlorophenyl)-6-nitro-D-norleucinate (0.52 g, 0.85 mmol) in EtOH (5 mL). This slurry was hydrogenated under a balloon of hydrogen for 2 h. The reaction was filtered through Celite with more EtOH and concentrated to afford the title compound (0.45 g). MS 581 (M+1).

Step C. (3R)-3-Amino-6-(2,3-dichlorophenyl)azepan-2-one

To a solution benzyl $N^2,N^2$-bis(tert-butoxycarbonyl)-5-(2,3-dichlorophenyl)-D-lysinate (0.45 g, 0.77 mmol) in MeOH (4 mL) and water (2 mL) was added 1N NaOH (3.1 mL, 3.1 mmol). This solution was heated to 40° C. for 6 h, then neutralized with 1N HCl and concentrated. To a solution of this residue in DCM (10 mL) were added EDC (0.19 g, 0.97 mmol) and HOAT (53 mg, 0.39 mmol) followed by triethylamine (0.32 mL, 0.73 mmol). After 2 h, NaHCO₃ was added, the layers separated and the aqueous phase backwashed with DCM. The combined organics were dried over magnesium sulfate, filtered and concentrated. This residue was purified by silica gel chromatography (0.5%→10% MeOH/DCM) to give di-tert-butyl [(3R)-6-(2,3-dichlorophenyl)-2-oxoazepan-3-yl]imidodicarbonate (300 mg). MS 473 (M+1). Standard deprotection of a portion of this material gave the title product. MS 273 (M+1).

Essentially following the procedures outlined for the preparation of Intermediate 57, the Intermediates in Table I-3 were prepared. Compounds along the route to the Intermediates in Table I-3, can be further processed (e.g. alkylation of N1) according to those skilled in the art following essentially the same procedures as outlined above to afford another set of intermediates.

TABLE I-3

| Intermediate | C-3 | C-6 | $R^1$ | MS (M + 1) |
|---|---|---|---|---|
| 58 | R | R or S | 2-Cl-phenyl | 239.1 |
| 59 | R | R or S | 3-Cl-phenyl | 439.2 diBoc |
| 60 | R | R or S | cyclohexyl | 211.3 |
| 61 | R | R or S | isopropyl | 371.3 diBoc |
| 62 | R | R or S | benzyl | 219.2 |
| 63 | R | R or S | 3-Cl-2-F-phenyl | 257.2 |

Intermediate 64

(2S,6R)-6-Amino-4-(cyclopropylmethyl)-2-phenyl-1,4-oxazepan-5-one

Step A. tert-Butyl cyclopropylmethyl[(2S)-2-hydroxy-2-phenylethyl]carbamate (S)-Styrene oxide (4.83 g, 40.3 mmol) and cyclopropanemethylamine (4.00 g, 56.4 mmol) were dissolved in isopropyl alcohol (100 mL) and heated to reflux. After 8 h, the reaction was allowed to cool to ambient temperature and concentrated. Triethylamine (5.61 mL, 40.3 mmol) was added to a solution of the crude amine and di-tert-butyl dicarbonate (8.78 g, 40.3 mmol) in dichloromethane (100 mL). After 18 h, water was added, and the mixture was extracted with ethyl acetate. The organic layer was washed with brine, dried over magnesium sulfate, filtered and concentrated. Purification by silica gel chromatography (5% ethyl acetate/hexanes→20% ethyl acetate/hexanes) gave the title compound (5.48 g).

Step B. Methyl N-[(benzyloxy)carbonyl]-O-{(1S)-2-[(tert-butoxycarbonyl)(cyclopropylmethyl)amino]-1-phenylethyl}D -serinate Boron trifluoride diethyl etherate (0.10 mL, 0.84 mmol) was added to a solution of tert-butyl cyclopropylmethyl[(2S)-2-hydroxy-2-phenylethyl]carbamate (2.45 g, 8.39 mmol) and 1-benzyl 2-methyl (2R)-aziridine-1,2-dicarboxylate (1.97 g, 8.39 mmol) in chloroform (20 mL). After 3 h, the reaction was concentrated. Purification by silica gel chromatography (100% hexanes→30% ethyl acetate/hexanes) gave the title compound (1.21 g).

Step C. N-[(Benzyloxy)carbonyl]-O-{(1S)-2-[(tert-butoxycarbonyl)(cyclopropylmethyl)amino]-1-phenylethyl}D -serine Aqueous sodium hydroxide (1N; 3.81 mL, 3.81 mmol) was added to a solution of methyl N-[(benzyloxy)carbonyl]-O-{(1S)-2-[(tert-butoxycarbonyl)(cyclopropylmethyl)amino]-1-phenylethyl}- D -serinate (1.30 g, 2.46 mmol) in tetrahydrofuran (20 mL). After 18 h, aqueous hydrochloric acid (1N; 3.81 mL, 3.81 mmol) was added. The mixture was extracted with dichloromethane (3×), and the combined organic extracts were dried over magnesium sulfate, filtered, and concentrated to give the title compound. (1.27 g) MS 535 (M+Na).

Step D. Benzyl (2S,6R)-4-(cyclopropylmethyl)-5-oxo-2-phenyl-1,4-oxazepan-6-ylcarbamate Trifluoroacetic acid (5.0 mL) was added to a solution N-[(benzyloxy)carbonyl]-O-{(1S)-2-[(tert-butoxycarbonyl)(cyclopropylmethyl)amino]-1-phenylethyl}-D-serine (1.27 g, 2.47 mmol) in dichloromethane (15 mL). After 2 h, the mixture was concentrated and azeotroped with toluene (3×) to give the crude amine. Diphenylphosphoryl azide (1.07 ml, 4.95 mmol) was added to a solution of the crude amine and 4-methylmorpholine (0.82 mL, 7.41 mmol) in N,N-dimethylformamide (100 mL). After 18 h, the mixture was concentrated and water was added. The mixture was extracted with ethyl acetate, and the organic layer was washed with water (2×) and saturated brine, dried over magnesium sulfate, filtered, and concentrated. Purification by silica gel chromatography (5% ethyl acetate/hexanes→50% ethyl acetate/hexanes) gave the title compound (0.426 g). MS 395 (M+1).

Step E. (2S,6R)-6-Amino-4-(cyclopropylmethyl)-2-phenyl-1,4-oxazepan-5-one

10% Palladium on carbon (20 mg) was added to a solution (2S,6R)-6-amino-4-(cyclopropylmethyl)-2-phenyl-1,4-oxazepan-5-one (179 mg, 0.454 mmol) in ethanol (15 mL). The reaction vessel was evacuated and back-filled with nitrogen (3×), then back-filled with hydrogen (1 atm). After 18 h, the mixture was filtered and concentrated to give the title compound (113 mg). MS 261 (M+1). $^1$H NMR (500 MHz, CDCl$_3$) δ 7.40-7.31 (m, 5H), 4.53 (d, J=8.5 Hz, 1H), 4.10-4.03 (m, 2H), 3.90 (dd, J=15.9, 7.1 Hz, 1H), 3.80-3.65 (m, 2H), 3.36 (d, J=15.9 Hz, 1H), 3.03 (dd, J=13.9, 6.6 Hz, 1H), 1.06-1.01 (m, 1H), 0.64-0.53 (m, 2H), 0.33-0.25 (m, 2H).

Intermediate 65

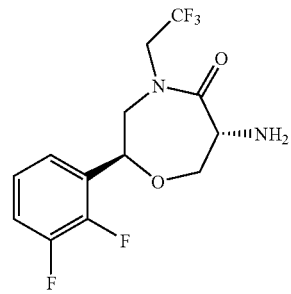

(2S,6R)-6-Amino-2-(2,3-difluorophenyl)-4-(2,2,2-trifluoroethyl)-1,4-oxazepan-5-one The title compound was prepared using a similar procedure to Intermediate 64. MS 325 (M+1).

Intermediate 66

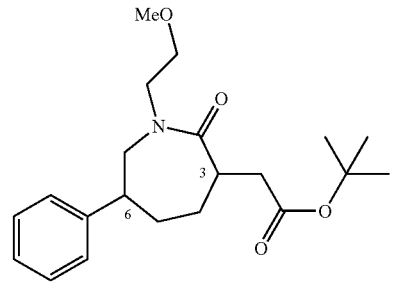

tert-Butyl[1-(2-methoxyethyl)-2-oxo-6-phenylazepan-3-yl]acetate

Step A. 1-(2-Methoxyethyl)-6-phenylazepan-2-one

Sodium hydride (60% dispersion in mineral oil; 0.32 g, 8.03 mmol) was added to a solution of 6-phenylazepan-2-one (0.76 g, 4.02 mmol) in N,N-dimethylformamide (15 mL) at 0° C., followed by the addition of 2-bromoethyl methyl ether (0.837 g, 6.03 mmol), and the mixture was allowed to warm to ambient temperature. After 21 h, water was added and the mixture was extracted with ethyl acetate (3×). The combined organic extracts were washed with water (3×), saturated brine, dried over sodium sulfate, filtered and concentrated. MS 248 (M+1).

Step B. tert-Butyl[1-(2-methoxyethyl)-2-oxo-6-phenylazepan-3-yl]acetate

Lithium diisopropylamide (1.8 M in heptane/tetrahydrofuran/ethylbenzene; 0.58 g, 5.41 mmol) was added to a solution of 1-(2-methoxyethyl)-6-phenylazepan-2-one (1.03 g, 4.16 mmol) in tetrahydrofuran (40 mL) at −78° C. After 2 h, tert-butylbromoacetate was added. After an additional 1.5 h, the reaction was quenched with methanol and allowed to warm to ambient temperature and concentrated. Purification by reverse phase HPLC (C-18, 95% water/acetonitrile→5% water/acetonitrile with 0.1% trifluoroacetic acid) gave 450 mg (cis isomer) and 350 mg (trans isomer) of the title compound. MS 362 (M+1). cis isomer: ¹H NMR (500 MHz, CDCl₃) δ 7.29 (t, J=7.6 Hz, 2H), 7.26 (m, 1H), 7.22-7.20 (m, 2H), 4.04 (br d, J=15.2 Hz, 1H), 3.84 (dt, J=13.9, 4.9 Hz, 1H), 3.51 (dd, J=15.4, 3.9 Hz, 1H), 3.40-3.35 (m, 1H), 3.30-3.21 (m, 2H), 3.24 (s, 3H), 3.02-3.00 (m, 1H), 2.84 (dd, J=16.4, 7.6 Hz, 1H), 2.68-2.66 (m, 1H), 2.33 (dd, J=16.4, 6.8 Hz, 1H), 2.11-2.07 (m, 1H), 2.05-1.95 (m, 1H), 1.80-1.76 (m, 2H), 1.46 (s, 9H). trans isomer: ¹H NMR (500 MHz, CDCl₃) δ 7.32 (t, J=7.3 Hz, 2H), 7.24-7.21 (m, 1H), 7.18 (d, J=7.1 Hz, 2H), 3.96 (dd, J=14.9, 10.0 Hz, 1H), 3.82-3.77 (m, 1H), 3.56-3.46 (m, 2H), 3.43-3.38 (m, 1H), 3.34 (s, 3H), 3.30 (d, J=15.1 Hz, 1H), 3.20-3.15 (m, 1H), 2.85 (dd, J=16.6, 7.8 Hz, 1H), 2.78 (br t, 1H), 2.26 (dd, J=16.6, 6.6 Hz, 1H), 2.10 (br d, J=22.7, 9.3 Hz, 1H), 1.77-1.73 (m, 1H), 1.62-1.59 (m, 1H), 1.46 (s, 9H).

Intermediate 67

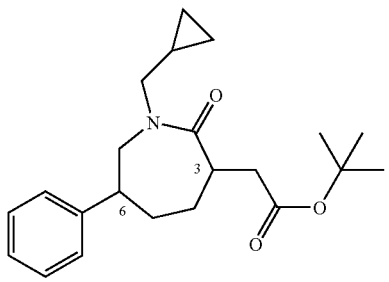

tert-Butyl[1-(cyclopropylmethyl)-2-oxo-6-phenylazepan-3-yl]acetate

The title compounds (both cis and trans) were prepared with cyclopropylmethyl bromide and 6-phenylazepan-2-one using a similar procedure to Intermediate 66. MS 358 (M+1).

Intermediate 68

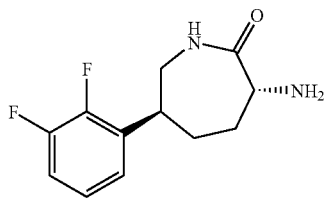

(3R,6S)-3-Amino-6-(2,3-difluorophenyl)azepan-2-one

Step A.
2-Bromo-N-(2,4-dimethoxybenzyl)prop-2-en-1-amine

Triethylamine (16.0 mL, 114 mmol) was added to a solution of 2,4-dimethoxybenzylamine hydrochloride (11.1 g, 54.5 mmol) and 2,3-dibromopropene (10.9 g, 54.5 mmol) in dichloromethane (200 mL). After 18 h, water was added and the mixture was extracted with dichloromethane (3×). The combined organic extracts were washed with saturated brine, dried over magnesium sulfate, filtered and concentrated. Purification by silica gel chromatography [100% dichloromethane→95% dichloromethane/5% (10% ammonium hydroxide/methanol)] gave the title compound (7.85 g).

Step B. Benzyl (1R)-1-{[(2-bromoprop-2-enyl)(2,4-dimethoxybenzyl)amino]carbonyl}but-3-enylcarbamate 1-[3-(Dimethylamino)propyl]-3-ethylcarbodiimide hydrochloride (55 mg, 0.285 mmol) was added to a solution of 2-bromo-N-(2,4-dimethoxybenzyl)prop-2-en-1-amine (73 mg, 0.256 mmol) and (2R)-2-{[(benzyloxy)carbonyl]amino}pent-4-enoic acid (71 mg, 0.285 mmol) in dichloromethane (5 mL). After 18 h the mixture was concentrated. Purification by silica gel chromatography (5% ethyl acetate/hexanes→30% ethyl acetate/hexanes) gave the title compound (77 mg). MS 517 (M+1).

Step C. Benzyl (1R)-1-{[[2-(2,3-difluorophenyl)prop-2-enyl](2,4-dimethoxybenzyl)amino]carbonyl}but-3-enylcarbamate Dichloro[1,1'-bis(diphenylphosphino)ferrocene]palladium dichloromethane adduct (0.726 g, 0.889 mmol) was added to a solution of benzyl (1R)-1-{[(2-bromoprop-2-enyl)(2,4-dimethoxybenzyl)amino]carbonyl}but-3-enylcarbamate (9.2 g, 17.8 mmol), 2,3-difluorophenylboronic acid (2.95 g, 18.7 mmol) and sodium carbonate (2M in water; 19.6 mL, 39.1 mmol) in N,N-dimethylformamide (60 mL) and the mixture was heated to 75° C. After 2 h, the mixture was allowed to cool to ambient temperature and extracted with dichloromethane (3×). The combined organic extracts were washed with saturated brine, dried over magnesium sulfate, filtered and concentrated. Purification by silica gel chromatography (5% ethyl acetate/hexanes→55% ethyl acetate/hexanes) gave the title compound (6.8 g). MS 551.2 (M+1).

Step D. Benzyl (3R)-6-(2,3-difluorophenyl)-1-(2,4-dimethoxybenzyl)-2-oxo-2,3,4,7-tetrahydro-1H-azepin-3-ylcarbamate

[1,3-bis-(2,4,6-Trimethylphenyl-2-imidazolidinylidene)dichloro(phenylmethylene)-(tricyclohexylphosphine)ruthenium] (Grubbs second generation catalyst) (2.62 g, 3.09 mmol) was added to a solution of benzyl (1R)-1-{[[2-(2,3-difluorophenyl)prop-2-enyl](2,4-dimethoxybenzyl)amino]carbonyl}but-3-enylcarbamate (6.8 g, 12.35 mmol) in dichloromethane (1800 mL) and the solution was heated to 40° C. After 48 h, additional catalyst was added (0.52 g, 0.61 mmol) and the reaction continued to heat at 40° C. for an additional 48 h. The mixture was allowed to cool to ambient temperature and concentrated. Purification by silica gel chromatography (5% ethyl acetate/hexanes→55% ethyl acetate/hexanes) gave the title compound (3.71 g). MS 523.1 (M+1).

Step, E. Benzyl (3R)-6-(2,3-difluorophenyl)-2-oxo-2,3,4,7-tetrahydro-1H-azepin-3-ylcarbamate Trifluoroacetic acid (60 mL) was added to a solution of benzyl (3R)-6-(2,3-difluorophenyl)-1-(2,4-dimethoxybenzyl)-2-oxo-2,3,4,7-tetrahydro-1H-azepin-3-ylcarbamate (3.70 g, 7.08 mmol) in dichloromethane (40 mL). After 18 h, the mixture was concentrated at 25° C., methanol (150 mL) was added, and the precipitate filtered. The filtrate was concentrated, diluted with dichloromethane (100 mL), washed with water (2×), saturated aqueous sodium bicarbonate (2×), saturated brine, dried over magnesium sulfate, filtered and concentrated. Purification by silica gel chromatography (5% ethyl acetate/hexanes→65% ethyl acetate/hexanes) gave the title compound (1.75 g). MS 373.1 (M+1).

Step F. tert-Butyl (3R,6S)-6-(2,3-difluorophenyl)-2-oxoazepan-3-ylcarbamate

10% Palladium on carbon (700 mg) was added to a solution of benzyl (3R)-6-(2,3-difluorophenyl)-2-oxo-2,3,4,7-tetrahydro-1H-azepin-3-ylcarbamate (2.6 g, 6.98 mmol) and di-tert-butyl dicarbonate (5.03 g, 23.0 mmol) in toluene (200 mL). The reaction vessel was evacuated and back-filled with nitrogen (3×), then back-filled with hydrogen (1 atm). After 24 h, the mixture was filtered and concentrated. Purification by preparative reverse phase chromatography (DeltaPak C18, 15μ, 47 mm×300 mm, 70 mL/min: 80% $H_2O/NH_4OAc$: 20% $CH_3CN$ to 100% $CH_3CN$ over 60 min) afforded the pure trans title compound (1.2 g). MS 341.2 (M+1). $^1H$ NMR (500 MHz, $CDCl_3$) δ 7.07-7.04 (m, 2H), 6.91-6.89 (m, 1H), 6.04 (br s, 1H), 5.93 (d, J=5.6 Hz, 1H), 4.46 (dd, J=10.5, 4.6 Hz, 1H), 3.65-3.59 (m, 1H), 3.21 (dd, J=15.1, 7.3 Hz, 1H), 3.05-3.00 (m, 1H), 2.25-2.20 (m, 1H), 2.17-2.10 (m, 2H), 1.79-1.71 (m, 1H), 1.46 (s, 9H).

Step G. (3R,6S)-3-Amino-6-(2,3-difluorophenyl)azepan-2-one

Trifluoroacetic acid (4 mL) was added to a solution of tert-butyl (3R,6S)-6-(2,3-difluorophenyl)-2-oxoazepan-3-ylcarbamate (82 mg, 0.241 mmol) in dichloromethane (4 mL). After 1 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated. MS 241.0 (M+1)

Alternatively, Intermediate 68 can be made in the following manner:

Step H. 1-Benzyl 5-methyl N,N-bis(tert-butoxycarbonyl)-D-glutamate

To a solution of Boc-D-Glu-OBn (50.0 g, 148.2 mmol) in DCM (400 ml) and MeOH (100 ml) was added trimethylsilyldiazomethane (88.9 mL of 2.0 M solution in hexanes, 117.8 mmol) at 0° C. dropwise via an addition funnel. After 60 min the reaction was concentrated. This residue was diluted with $CH_3CN$ (400 mL) and $(Boc)_2O$ (48.5 g, 222.3 mmol) was added followed by DMAP (18.1 g, 14.8 mmol). After 24 h the reaction was concentrated and purified by silica gel chromatography (10%→60% ethyl acetate/hexanes) to give the title compound (48.20 g, 72%). MS 252.2 (M+1-2Boc).

Step I. Benzyl (2R,5E)-2-[bis(tert-butoxycarbonyl)amino]-6-nitrohex-5-enoate To a −78° C. of 1-benzyl 5-methyl N,N-bis(tert-butoxycarbonyl)-D-glutamate (48.2 g, 106.8 mmol) in $Et_2O$ (400 mL), was added DIBAL (133.4 mL of 1.0 M solution in toluene, 133.4 mmol) slowly so as not to let the internal temperature exceed −65° C. After 15 min, 20 mL more of DIBAL was added. After stirring for additional 20 min, water (300 mL) was added and the reaction was warmed to room temperature and stirred for 30 min. This mixture was further diluted with $Et_2O$ and $H_2O$, the layers separated and the aqueous phase extracted with more $Et_2O$. The combined organics extracts were washed with a saturated aqueous solution of sodium potassium tartrate (2×), brine, dried over magnesium sulfate, filtered and concentrated to give benzyl N,N-bis(tert-butoxycarbonyl)-5-oxo-D-norvalinate (44.4 g) which was carried directly into the next step. MS 444.1 (M+Na). This material was dissolved in toluene (310 mL) and nitromethane (57.1 mL, 1.05 mol) and 1,1,3,3-tetramethylguanidine (1.3 mL, 10.5 mmol) were added at 0° C. After stirring for 30 min the nitroaldol reaction was complete, so methanesulfonyl chloride (12.2 mL, 158 mmol) was added followed triethylamine (22.0 mL, 158 mmol) at 0° C. and the reaction was allowed to warm to RT. After 1 h, 4 mL MsCl and 5.5 mL triethylamine were added. After stirring for an additional 30 min the mixture was diluted with $Et_2O$ and $NaHCO_3$, the phases separated and the aqueous layer backwashed with another portion of $Et_2O$. The combined organics were dried over magnesium sulfate, filtered and concentrated to give a residue that was purified by silica gel chromatography (5%→50% ethyl acetate/hexanes) to give the title compound (34.3 g, 70%). MS 487.1 (M+Na).

Step J. Benzyl (5S)—N,N-bis(tert-butoxycarbonyl)-5-(2,3-difluorophenyl)-6-nitro-D-norleucinate A solution of benzyl (2R,5E)-2-[bis(tert-butoxycarbonyl)amino]-6-nitrohex-5-enoate (34.0 g, 73.2 mmol), 2,3-difluorophenylboronic acid (28.9 g, 183.0 mmol) and water (4.62 mL, 256.2 mmol) in dioxane (240 mL) was degassed with argon for 15 min. To this solution was added sodium bicarbonate (3.08 g, 36.6 mmol), (S)-BINAP (1.28 g, 2.05 mmol) and acetylacetanotobis(ethylene)rhodium(I) (0.472 g, 1.83 mmol). The mixture was stirred at RT for 2 min then heated to 35° C. After 4 h, 255 mg of (S)-BINAP and 94 mg of acetylacetanotobis(ethylene)rhodium(I) were added. After an additional 2 h the reaction was diluted with $DCM/NaHCO_3$, the layers separated and the aqueous phase was backwashed with another portion of DCM. The combined organics were dried over magnesium sulfate, filtered and concentrated to give a residue that was purified by silica gel chromatography (5%→60% ethyl acetate/hexanes) to give the title compound (37.0 g, 87%) contaminated with ~5% SR isomer. MS 379.1 (M+1-2Boc).

Step K. (5S)—$N^2,N^2$-Bis(tert-butoxycarbonyl)-5-(2,3-difluorophenyl)-D-lysine A solution of benzyl (5S)—N,N-bis(tert-butoxycarbonyl)-5-(2,3-difluorophenyl)-6-nitro-D-norleucinate (15.5 g, 26.8 mmol) and 10% Pd/C (12.0 g) in EtOH (175 mL, SureSeal from Aldrich), was hydrogenated at 55 psi overnight. After 18 h, another 4 g of 10% Pd/C was added and the reaction hydrogenated at 55 psi for another 18 h. The reaction was filtered through Celite with more EtOH and concentrated to afford the title compound (12.0 g). MS 459.2 (M+1).

Step L. tert-Butyl (3R,6S)-6-(2,3-difluorophenyl)-2-oxoazepan-3-ylcarbamate

To a solution (5S)—$N^2,N^2$-bis(tert-butoxycarbonyl)-5-(2,3-difluorophenyl)-D-lysine (22.0 g, 48.0 mmol) in DCM (700 mL) were added EDC (11.0 g, 57.6 mmol) and HOAT (3.27 g, 24.0 mmol) followed by triethylamine (10.0 mL, 72.0 mmol). After 60 min, $NaHCO_3$ was added, the layers separated and the aqueous phase backwashed with DCM. The combined organics were dried over magnesium sulfate, filtered and concentrated. The residue was purified by silica gel Intermediate 69

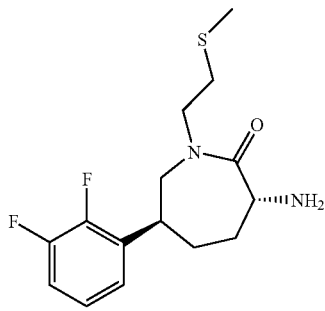

(3R,6S)-3-Amino-6-(2,3-difluorophenyl)-1-[2-(methylthio)ethyl]azepan-2-one

Step A. tert-butyl (3R,6S)-6-(2,3-difluorophenyl)-1-[2-(methylthio)ethyl]-2-oxoazepan-3-ylcarbamate Sodium hydride (60% dispersion in mineral oil; 40 mg, 0.600 mmol) was added to a solution of tert-butyl (3R,6S)-6-(2,3-difluorophenyl)-2-oxoazepan-3-ylcarbamate (170 mg, 0.500 mmol) in N,N-dimethylformamide (4 mL) at 0° C. After 5 min the mixture was cooled to −30° C. and 1-iodo-2-(methylthio)ethane [prepared according to known procedures: J. Org. Chem., 1987, 52, 2299-2301 (158 mg, 0.782 mmol)] was added. Additional sodium hydride (33 mg, 0.50 mmol) was added and after 4 h excess sodium hydride (33 mg, 0.50 mmol) and 1-iodo-2-(methylthio)ethane (75.6 mg, 0.374 mmol) were added. After 3 h, the final portions of sodium hydride (33 mg, 0.50 mmol) and 1-iodo-2-(methylthio) ethane (75.6 mg, 0.374 mmol) were added and the mixture stirred at −20° C. overnight. The reaction was quenched with water and the mixture was extracted with ethyl acetate. The organic layer was washed with water (3×), saturated brine, dried over magnesium sulfate, filtered and concentrated. Purification by silica gel chromatography (0% ethyl acetate/hexanes→50% ethyl acetate/hexanes) gave the title compound (77 mg). MS 415 (M+1).

Step B. (3R,6S)-3-Amino-6-(2,3-difluorophenyl)-1-[2-(methylthio)ethyl]azepan-2-one Trifluoroacetic acid (2 mL) was added to a solution of tert-butyl (3R,6S)-6-(2,3-difluorophenyl)-1-[2-(methylthio)ethyl]-2-oxoazepan-3-ylcarbamate (77 mg, 0.186 mmol) in dichloromethane (10 mL). After 30 min, the solution was concentrated and azeotroped with toluene (2×). Saturated aqueous sodium bicarbonate solution was added and the mixture was extracted with dichloromethane (3×). The combined organic extracts were washed with saturated brine, dried over magnesium sulfate, filtered and concentrated. MS 315.2 (M+1).

Intermediate 70

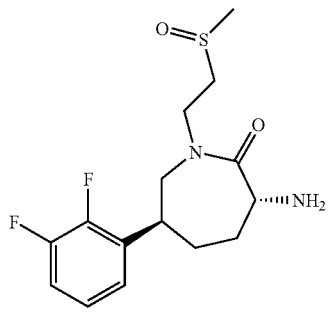

(3R,6S)-3-Amino-6-(2,3-difluorophenyl)-1-[2-(methylsulfinyl)ethyl]azepan-2-one

Step A. tert-Butyl (3R,6S)-6-(2,3-difluorophenyl)-1-[2-(methylsulfinyl)ethyl]-2-oxoazepan-3-ylcarbamate Sodium periodate (11.3 mg, 0.053 mmol) was added to a solution of tert-butyl (3R,6S)-6-(2,3-difluorophenyl)-1-[2-(methylthio)ethyl]-2-oxoazepan-3-ylcarbamate (22 mg, 0.053 mmol) in methanol (2 mL) and water (2 mL). After 30 min excess sodium periodate (22 mg, 0.11 mmol) was added. After 18 h, saturated aqueous sodium carbonate was added and the mixture was extracted with ethyl acetate. The organic layer was washed with saturated aqueous sodium carbonate (3×), saturated brine, dried over magnesium sulfate, filtered and concentrated to give the title compound. MS 431 (M+1).

Step B. (3R,6S)-3-Amino-6-(2,3-difluorophenyl)-1-[2-(methylsulfinyl)ethyl]azepan-2-one Trifluoroacetic acid (1 mL) was added to a solution of tert-butyl (3R,6S)-6-(2,3-difluorophenyl)-1-[2-(methylsulfinyl)ethyl]-2-oxoazepan-3-ylcarbamate (23 mg, 0.053 mmol) in dichloromethane (2 mL). After 3 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated to give the title compound. MS 331 (M+1).

Intermediate 71

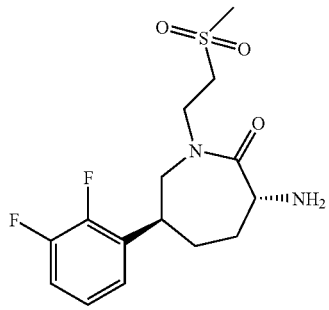

(3R,6S)-3-Amino-6-(2,3-difluorophenyl)-1-[2-(methylsulfonyl)ethyl]azepan-2-one

Step A. tert-Butyl (3R,6S)-6-(2,3-difluorophenyl)-1-[2-(methylsulfonyl)ethyl]-2-oxoazepan-3-ylcarbamate Oxone® ((16.1 mg, 0.11 mmol) was added to a solution of tert-butyl (3R,6S)-6-(2,3-difluorophenyl)-1-[2-(methylthio)ethyl]-2-oxoazepan-3-ylcarbamate (22 mg, 0.053 mmol) in methanol (2 mL) and water (2 mL). After 6 h excess oxone (32 mg, 0.22 mmol) was added. After 18 h, the reaction was quenched with aqueous sodium sulfite solution and the mixture was extracted with ethyl acetate. The organic layer was washed with saturated aqueous sodium carbonate (3×), saturated brine, dried over magnesium sulfate, filtered and concentrated to give the title compound. MS 447 (M+1).

Step B. (3R,6S)-3-Amino-6-(2,3-difluorophenyl)-1-[2-(methylsulfonyl)ethyl]azepan-2-one Trifluoroacetic acid (1 mL) was added to a solution of tert-butyl (3R,6S)-6-(2,3-difluorophenyl)-1-[2-(methylsulfonyl)ethyl]-2-oxoazepan-3-ylcarbamate (23.7 mg, 0.053 mmol) in dichloromethane (2 mL). After 4 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated to give the title compound. MS 347 (M+1).

Intermediate 72

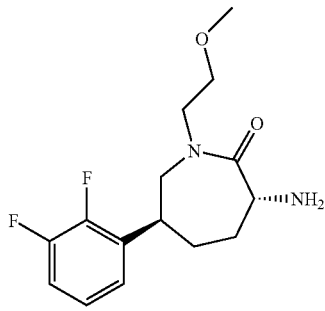

(3R,6S)-3-Amino-6-(2,3-difluorophenyl)-1-(2-methoxyethyl)azepan-2-one

Step A. tert-Butyl (3R,6S)-6-(2,3-difluorophenyl)-1-(2-methoxyethyl)-2-oxoazepan-3-ylcarbamate Sodium hydride (60% dispersion in mineral oil; 17.6 mg, 0.264 mmol) was added to a solution of tert-butyl (3R,6S)-6-(2,3-difluorophenyl)-2-oxoazepan-3-ylcarbamate (75 mg, 0.220 mmol) in N,N-dimethyl formamide (2 mL) at 0° C. After 5 min, 2-bromoethyl methyl ether (0.025 mL, 0.264 mmol) was added and the mixture was allowed to warm to ambient temperature. After 3 h, the reaction was quenched with water and the mixture was extracted with ethyl acetate. The organic layer was washed with water (2×), saturated brine, dried over magnesium sulfate, filtered and concentrated to give the title compound. MS 421 (M+Na).

Step B. (3R,6S)-3-Amino-6-(2,3-difluorophenyl)-1-(2-methoxyethyl)azepan-2-one Trifluoroacetic acid (2.5 mL) was added to a solution of tert-butyl (3R,6S)-6-(2,3-difluorophenyl)-1-(2-methoxyethyl)-2-oxoazepan-3-ylcarbamate (99 mg, 0.248 mmol) in dichloromethane (5 mL). After 1 h, the solution was concentrated and azeotroped with toluene (2×). Saturated aqueous sodium bicarbonate solution was added and the mixture was extracted with dichloromethane (3×). The combined organic extracts were washed with saturated brine, dried over magnesium sulfate, filtered and concentrated. MS 299.2 (M+1).

Intermediate 73

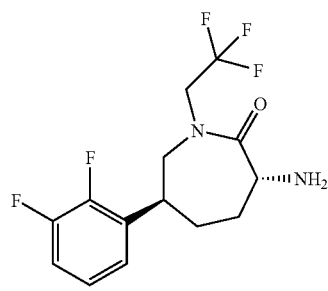

(3R,6S)-3-Amino-6-(2,3-difluorophenyl)-1-(2,2,2-trifluoroethyl)azepan-2-one

Step A: tert-Butyl (3R,6S)-6-(2,3-difluorophenyl)-2-oxo-1-(2,2,2-trifluoroethyl)azepan-3-ylcarbamate Sodium hydride (60% dispersion in mineral oil; 70.7 mg, 1.06 mmol) was added to a solution of tert-butyl (3R,6S)-6-(2,3-difluorophenyl)-2-oxoazepan-3-ylcarbamate (301 mg, 0.884 mmol) in N,N-dimethylformamide (7 mL) at −35° C. After 15 min, 2,2,2-trifluoroethyl trichloromethanesulfonate (0.314 mL, 1.91 mmol) was added and the reaction was stirred at −35° C. After 30 min, an additional amount of sodium hydride (27 mg, 0.40 mmol) and 2,2,2-trifluoroethyl trichloromethanesulfonate (0.140 mL, 0.85 mmol) were added. After 2 h, the reaction was quenched with water and the mixture was extracted with ethyl acetate. The organic layer was washed with water (3×), saturated brine, dried over magnesium sulfate, filtered and concentrated. Purification by silica gel chromatography (0% ethyl acetate/hexanes→30% ethyl acetate/hexanes) gave the title compound (306 mg). MS 423 (M+1).

Step B: (3R,6S)-3-Amino-6-(2,3-difluorophenyl)-1-(2,2,2-trifluoroethyl)azepan-2-one Trifluoroacetic acid (2.5 mL) was added to a solution of tert-butyl (3R,6S)-6-(2,3-difluorophenyl)-2-oxo-1-(2,2,2-trifluoroethyl)azepan-3-ylcarbamate (135 mg, 0.320 mmol) in dichloromethane (5 mL). After 30 min, the solution was concentrated and azeotroped with toluene (2×). Saturated aqueous sodium bicarbonate solution was added and the mixture was extracted with dichloromethane (3×). The combined organic extracts were washed with saturated brine, dried over magnesium sulfate, filtered and concentrated. MS 323.1 (M+1). $^1$H NMR (500 MHz, CDCl$_3$) δ 7.11-7.03 (m, 2H), 6.93-6.89 (m, 1H), 4.21-4.13 (m, 1H), 4.10-3.98 (m, 2H), 3.85 (d, J=11.0 Hz, 1H), 3.35 (d, J=15.4 Hz, 1H), 3.04-2.99 (m, 1H), 2.13-2.09 (m, 2H), 2.08-2.02 (m, 1H), 1.78-1.70 (m, 3H).

Intermediate 74

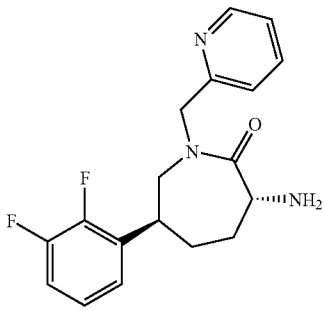

(3R,6S)-3-Amino-6-(2,3-difluorophenyl)-1-(pyridin-2-ylmethyl)azepan-2-one

Step A. tert-Butyl (3R,6S)-6-(2,3-difluorophenyl)-2-oxo-1-(pyridin-2-ylmethyl)azepan-3-ylcarbamate Sodium hydride (60% dispersion in mineral oil; 30 mg, 1.175 mmol) was added to a solution of tert-butyl (3R,6S)-6-(2,3-difluorophenyl)-2-oxoazepan-3-ylcarbamate (160 mg, 0.470 mmol) in N,N-dimethylformamide (6 mL) at 0° C. After 30 min, 2-bromomethylpyridine (0.125 mg, 0.494 mmol) was added. After 1 h, the reaction was quenched with water and the mixture was extracted with ethyl acetate. The organic layer was washed with water (2×), saturated brine, dried over magnesium sulfate, filtered and concentrated to give the title compound (202 mg). MS 432.2 (M+1).

Step B. (3R,6S)-3-Amino-6-(2,3-difluorophenyl)-1-(pyridin-2-ylmethyl)azepan-2-on Trifluoroacetic acid (3 mL) was added to a solution of tert-butyl (3R,6S)-6-(2,3-difluorophenyl)-2-oxo-1-(pyridin-2-ylmethyl)azepan-3-ylcarbamate (202 mg, 0.468 mmol) in dichloromethane (4 mL). After 18 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated. MS 332.2 (M+1).

Intermediate 75

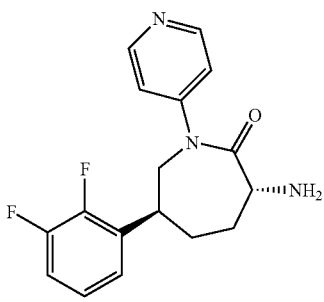

(3R,6S)-3-Amino-6-(2,3-difluorophenyl)-1-pyridin-4-ylazepan-2-one

Step A. tert-Butyl (3R,6S)-6-(2,3-difluorophenyl)-2-oxo-1-pyridin-4-ylazepan-3-ylcarbamate 4-Bromopyridine (286 mg, 1.47 mmol) was added to a solution of tert-butyl (3R,6S)-6-(2,3-difluorophenyl)-2-oxoazepan-3-ylcarbamate (200 mg, 0.588 mmol), 4,5-bis(diphenylphosphino)-9,9-dimethylxanthene (20 mg, 0.035 mmol), tris(dibenzylideneacetone)dipalladium(0) (22 mg, 0.024 mmol), and cesium carbonate (268 mg, 0.823 mmol) in dioxane (6 mL) and the mixture was heated at 150° C. in a Personal Chemistry Smith Creator™ microwave reactor. After 30 min, an additional amount of 4,5-bis(diphenylphosphino)-9,9-dimethylxanthene (20 mg, 0.035 mmol) and tris(dibenzylideneacetone)dipalladium(0) (22 mg, 0.024 mmol) were added. After 30 min, the mixture was partitioned between ethyl acetate and water. The organic layer was washed with water (2×), saturated brine, dried over magnesium sulfate, filtered and concentrated to give the title compound (55 mg). MS 418.2 (M+1).

Step B. (3R,6S)-3-Amino-6-(2,3-difluorophenyl)-1-pyridin-4-ylazepan-2-one

Trifluoroacetic acid (2 mL) was added to a solution of tert-butyl (3R,6S)-6-(2,3-difluorophenyl)-2-oxo-1-pyridin-4-ylazepan-3-ylcarbamate (55 mg, 0.132 mmol) in dichloromethane (2 mL). After 1 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated. MS 318.2 (M+1).

Essentially following the procedures outlined for the preparation of Intermediates 69-75, the Intermediates in Table I-4 were prepared.

TABLE I-4

| Intermediate | R | MS (M + 1) |
|---|---|---|
| 76 | $CH_3$ | 255.2 |
| 77 | $CH_2CH_3$ | 269.2 |
| 78 | cyclopropyl-$CH_2$ | 295.2 |
| 79 | $CH_2CH_2F$ | 287 |
| 80 | $CH_2CHF_2$ | 305.1 |
| 81 | (tetrahydrofuran-2-yl)-$CH_2$ | 325.2 |
| 82 | (tetrahydrofuran-2-yl)-$CH_2$ | 325.2 |

TABLE I-4-continued

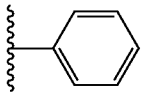

| Intermediate | R | MS (M + 1) |
|---|---|---|
| 83 | CH₂CO₂CH₃ | 313.1 |
| 84 | phenyl | 317.2 |
| 85 | 3-pyridyl | 318.1 |
| 86 | 4-(SO₂CH₃)phenyl | 395.1 |
| 87 | 3-(SO₂CH₃)phenyl | 395.1 |
| 88 | 6-methoxy-2-methylpyridin-3-yl | 362.2 |
| 89 | (pyridin-3-yl)methyl | 332 |
| 90 | (pyridin-3-yl)methyl | 332 |
| 91 | isopropoxymethyl-CH₂ | 327 |
| 92 | methoxyethyl-CH₂ | 313 |
| 93 | cyclopropoxymethyl-CH₂ | 325 |
| 94 | F₃C-O-CH₂ | 353 |
| 95 | (pyridin-2-yl N-oxide)methyl | 348 |
| 96 | pyrrolidin-1-yl-CH₂ | 338 |
| 97 | morpholin-4-yl-CH₂ | 354 |
| 98 | (CH₃)₂N-CH₂ | 312 |
| 99 | CH₂CO₂CH(CH₃)₂ | 341 |
| 100 | CbzNH-CH₂ | 418.2 |
| 101 | piperidin-1-yl-CH₂ | 352 |
| 102 | N(Cbz)(Me)-CH₂ | 432 |
| 103 | 4-methylpiperazin-1-yl-CH₂ | 367 |
| 104 | CH₂CH₂CF₃ | 337 |
| 105 | MeO₂C-CH(CH₃)-CH₂ | 341 |
| 106 | (pyrimidin-2-yl)methyl | 333 |

87

Intermediate 107

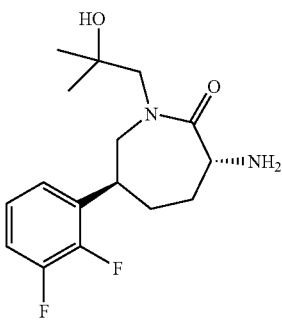

(3R,6S)-3-Amino-6-(2,3-difluorophenyl)-1-(2-hydroxy-2-methylpropyl)azepan-2-one

Step A. Di-tert-butyl [(3R,6S)-6-(2,3-difluorophenyl)-1-(2-hydroxy-2-methylpropyl)-2-oxoazepan-3-yl]imidodicarbonate A solution of (5S)—$N^2,N^2$-bis(tert-butoxycarbonyl)-5-(2,3-difluorophenyl)-D-lysine (0.569 g, 1.24 mmol), 1-chloro-2-methyl-2-propanol (0.202 g, 1.86 mmol) and diisopropylethylamine (0.529 g, 4.10 mmol) in EtOH (5 mL) was heated at 75° C. overnight. The reaction was concentrated to dryness, diluted with DCM (20 mL) and EDC (0.358 g, 1.87 mmol), HOAT (0.252 g, 1.87 mmol) were added followed by diisopropylethylamine (0.650 mL, 3.73 mmol). After stirring overnight, NaHCO$_3$ was added, the layers separated and the aqueous phase backwashed with DCM. The combined organics were dried over magnesium sulfate, filtered, concentrated and the residue purified by silica gel chromatography (10%→35% EtOAc/hexanes) to give the title compound (0.21 g). MS 513.1 (M+1). $^1$H NMR (500 MHz, CD$_3$OD) δ 7.1 (m, 3H), 5.24 (d, J=10.7 Hz, 1H), 4.02 (m, 1H), 3.69 (d, J=13.9 Hz, 1H), 3.60 (d, J=15.1 Hz, 1H), 3.39 (m, 1H), 3.24 (d, J=14.2 Hz, 1H), 2.4 (m, 1H), 2.1 (m, 3H), 1.5 (s, 18H), 1.20 (s, 3H), 1.16 (s, 3H).

Step B. (3R,6S)-3-Amino-6-(2,3-difluorophenyl)-1-(2-hydroxy-2-methylpropyl)azepan-2-one A solution of di-tert-butyl [(3R,6S)-6-(2,3-difluorophenyl)-1-(2-hydroxy-2-methylpropyl)-2-oxoazepan-3-yl]imidodicarbonate (0.095 g, 0.185 mmol) in DCM (10 mL) was treated with trifluoroacetic acid (3 mL). After 1 h the reaction was concentrated to dryness to afford the title compound as a TFA salt. MS 313.2 (M+1).

Intermediate 108

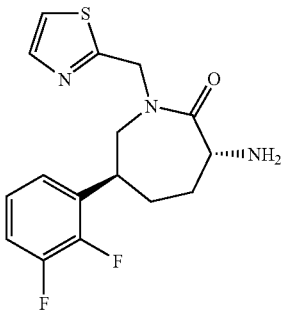

88

(3R,6S)-3-Amino-6-(2,3-difluorophenyl)-1-(1,3-thiazol-2-ylmethyl)azepan-2-one

Step A. Di-tert-butyl [(3R,6S)-6-(2,3-difluorophenyl)-2-oxo-1-(1,3-thiazol-2-ylmethyl)azepan-3-yl]imidodicarbonate A solution of (5S)—$N^2,N^2$-bis(tert-butoxycarbonyl)-5-(2,3-difluorophenyl)-D-lysine (0.871 g, 1.90 mmol), 2-formylthiazole (0.183 g, 1.62 mmol) and acetic acid (0.137 g, 2.28 mmol) in 1,2-dichloroethane (20 mL) was stirred at room temperature for 30 min. Sodium triacetoxyborohydride (0.604 g, 2.85 mmol) was added and the reaction stirred overnight. The reaction was diluted with saturated aqueous sodium bicarbonate, the layers separated, and the aqueous phase extracted with DCM (2×). The organic washes were combined, dried over magnesium sulfate, and concentrated. This residue was diluted with dichloromethane (20 mL) and EDC (0.569 g, 2.97 mmol), HOAT (0.401 g, 2.97 mmol) were added followed by diisopropylethylamine (1.04 mL, 5.94 mmol). After stirring overnight, NaHCO$_3$ was added, the layers separated and the aqueous phase backwashed with DCM. The combined organics were dried over magnesium sulfate, filtered, concentrated and the residue purified by silica gel chromatography (0%→40% EtOAc/hexanes) to give the title compound (0.49 g). MS 538.0 (M+1).) $^1$H NMR (500 MHz, CDCl$_3$) δ 7.73 (d, J=3.5 Hz, 1H), 7.37 (d, J=3.4 Hz, 1H), 7.0 (m, 2H), 6.8 (m, 1H), 5.20 (d, J=10.3 Hz, 1H), 5.03 (d, J=15.5 Hz, 1H), 4.96 (d, J=15.5 Hz, 1H), 3.84 (dd, J=10.3, 15.2 Hz, 1H), 3.48 (d, J=15.5 Hz, 1H), 2.94 (dd, J=11.0, 11.0 Hz, 1H), 2.50 (dd, 1H), 2.0 (m, 4H), 1.5 (s, 18H).

Step B. (3R,6S)-3-Amino-6-(2,3-difluorophenyl)-1-(1,3-thiazol-2-ylmethyl)azepan-2-one A solution of di-tert-butyl [(3R,6S)-6-(2,3-difluorophenyl)-2-oxo-1-(1,3-thiazol-2-ylmethyl)azepan-3-yl]imidodicarbonate (0.481 g, 0.895 mmol) in DCM (10 mL) was treated with trifluoroacetic acid (3 mL). After 1 h the reaction was diluted with saturated aqueous sodium bicarbonate, the layers separated, and the aqueous phase extracted with DCM (2×). The organic washes were combined, dried over magnesium sulfate, and concentrated to afford the title compound (0.30 mg). MS 338.2 (M+1).

Essentially following the procedures outlined for the preparation of Intermediates 107-108, the Intermediates in Table I-5 were prepared.

TABLE I-5

| Intermediate | R | MS (M + 1) |
|---|---|---|
| 109 | CH(CH$_3$)$_2$ | 283.2 |
| 110 | CH$_2$CH$_2$OH | 285.2 |

TABLE I-5-continued

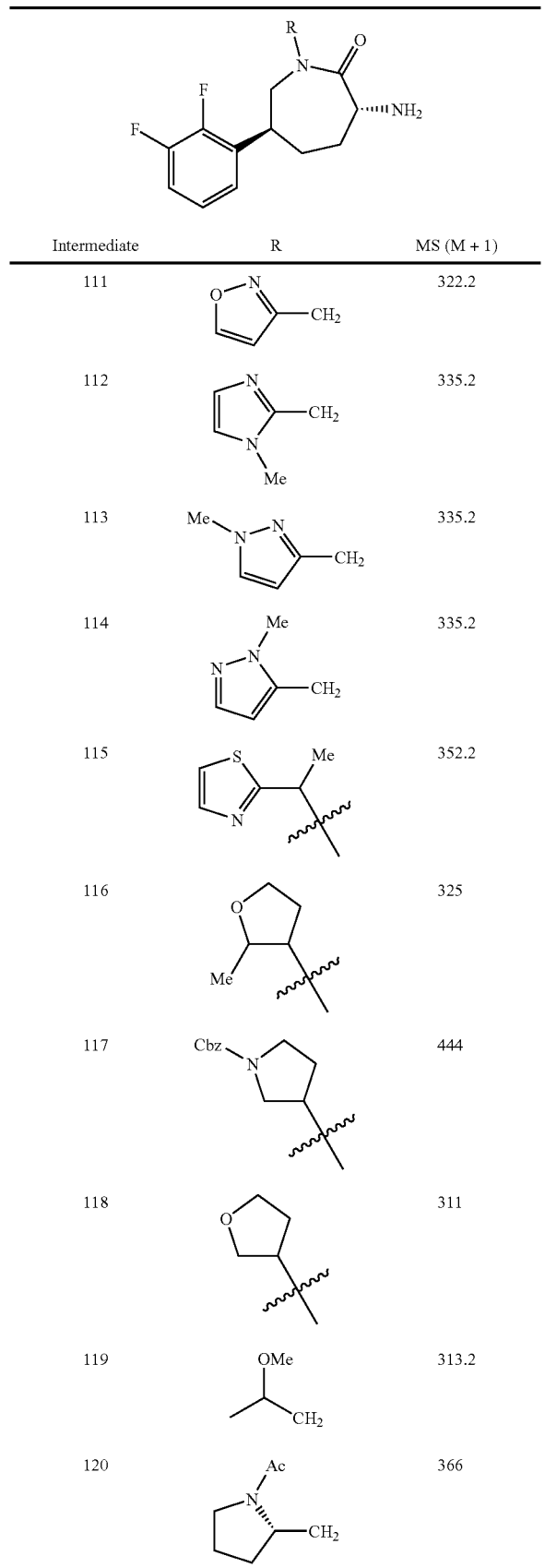

| Intermediate | R | MS (M + 1) |
|---|---|---|
| 111 | 3-methylisoxazol-CH₂ | 322.2 |
| 112 | 1-methylimidazol-2-yl-CH₂ | 335.2 |
| 113 | 1-methylpyrazol-3-yl-CH₂ | 335.2 |
| 114 | 1-methylpyrazol-5-yl-CH₂ | 335.2 |
| 115 | 1-(thiazol-2-yl)ethyl | 352.2 |
| 116 | 2-methyltetrahydrofuran-3-yl | 325 |
| 117 | N-Cbz-pyrrolidin-3-yl | 444 |
| 118 | tetrahydrofuran-3-yl | 311 |
| 119 | 2-methoxypropyl (OMe-CH(Me)-CH₂) | 313.2 |
| 120 | (2S)-N-Ac-pyrrolidin-2-yl-CH₂ | 366 |

TABLE I-5-continued

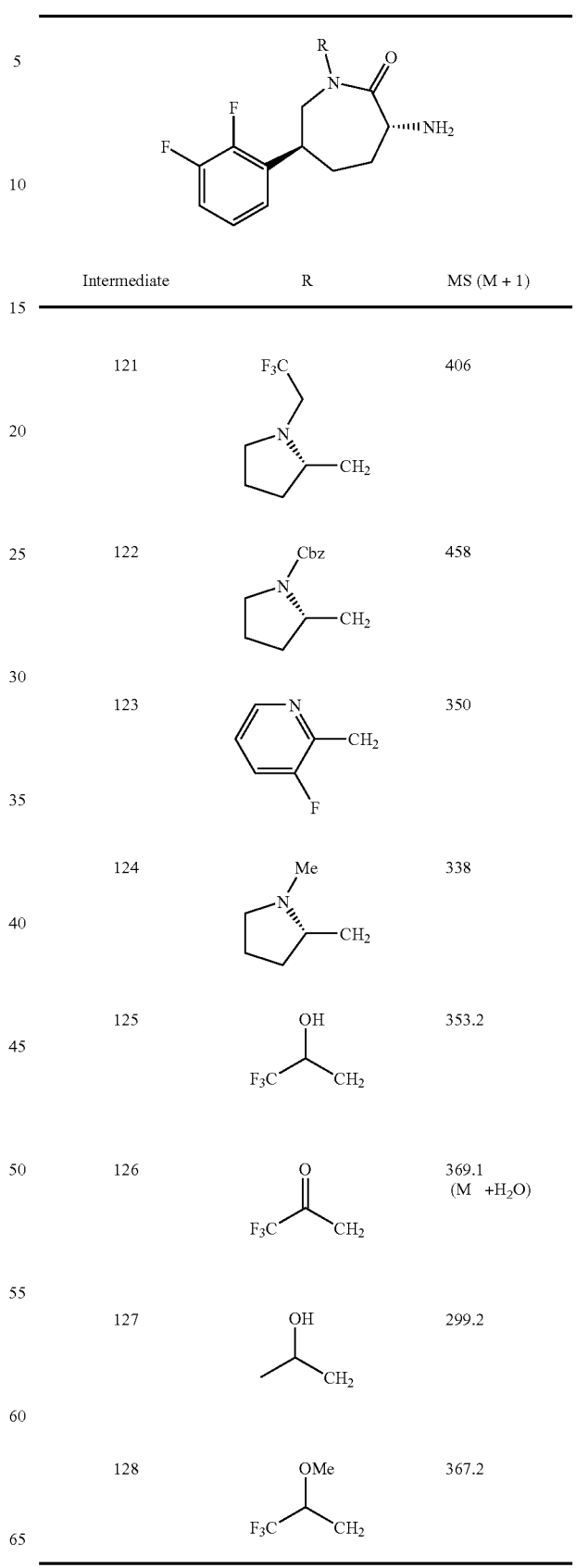

| Intermediate | R | MS (M + 1) |
|---|---|---|
| 121 | (2S)-N-(2,2,2-trifluoroethyl)pyrrolidin-2-yl-CH₂ | 406 |
| 122 | (2S)-N-Cbz-pyrrolidin-2-yl-CH₂ | 458 |
| 123 | 3-fluoropyridin-2-yl-CH₂ | 350 |
| 124 | (2S)-N-Me-pyrrolidin-2-yl-CH₂ | 338 |
| 125 | 3,3,3-trifluoro-2-hydroxypropyl | 353.2 |
| 126 | 3,3,3-trifluoro-2-oxopropyl | 369.1 (M +H₂O) |
| 127 | 2-hydroxypropyl | 299.2 |
| 128 | 2-methoxy-3,3,3-trifluoropropyl | 367.2 |

Example 1

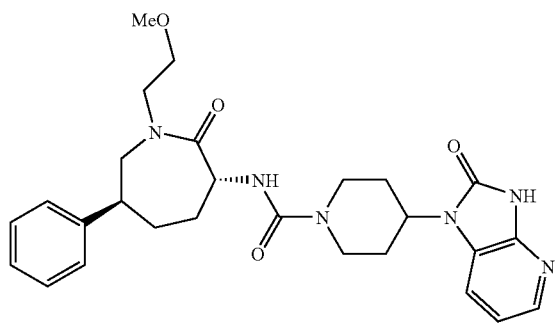

N-[(3R,6S)-1-(2-Methoxyethyl)-2-oxo-6-phenylazepan-3-yl]-4-(2-oxo-2,3-dihydro-1H-imidazo[4,5-b]pyridin-1-yl)piperidine-1-carboxamide Triethylamine (0.015 mL, 0.107 mmol) was added to a solution of (3R,6S)-3-amino-1-(2-methoxyethyl)-6-phenylazepan-2-one (28 mg, 0.107 mmol) and 4-nitrophenyl chloroformate (22 mg, 0.107 mmol) in tetrahydrofuran (2 mL) at 0° C. After 30 min, 2-oxo-1-(4-piperidinyl)-2,3-dihydro-1H-imidazo[4,5-b]pyridine dihydrochloride (37 mg, 0.128 mmol), diisopropylethylamine (0.074 mL, 0.427 mmol) and dichloromethane (2.5 mL) were added and the mixture allowed to warm to ambient temperature. After 18 h, saturated aqueous sodium carbonate was added and the mixture was extracted with ethyl acetate. The organic layer was washed with saturated aqueous sodium carbonate (3×), saturated brine, dried over magnesium sulfate, filtered and concentrated. Purification by silica gel chromatography (100% dichloromethane→93% dichloromethane/methanol) gave the title compound (45 mg). MS 507.2737 (M+1).

Essentially following the procedures outlined for the preparation of Example 1, the Examples in Table E-1 were prepared.

TABLE E-1

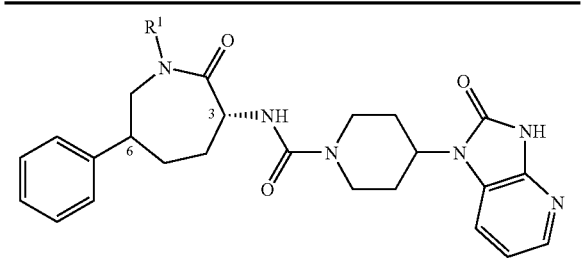

| Examples | C-3 | C-6 | $R^1$ | MS (M + 1) |
|---|---|---|---|---|
| 2 | R | S | H | 449 |
| 3 | R | R | H | 449 |
| 4 | R | S | $CH_3$ | 463 |
| 5 | R | S | $CH_2CH_3$ | 477 |
| 6 | R | S | $CH_2CF_3$ | 531.2326 |
| 7 | R | S | $CH_2CO_2CH_3$ | 521.2481 |
| 8 | R | S | $CH_2CO_2H$ | 507.2353 |
| 9 | R | S | $(CH_2)_2OCH_2CH_3$ | 521.2910 |
| 10 | R | S | $CH_2CN$ | 488.2378 |
| 11 | R | S | $(CH_2)_2OH$ | 493.2555 |

TABLE E-1-continued

| Examples | C-3 | C-6 | $R^1$ | MS (M + 1) |
|---|---|---|---|---|
| 12 | R | S | cyclopropyl-$CH_2$ | 503 |
| 13 | R | S | 1,3-dioxolan-2-yl-$CH_2$ | 535.2666 |
| 14 | R | S | $CH_2CH_2F$ | 495.2489 |
| 15 | R | S | $CH_2CHF_2$ | 513.2401 |
| 16 | R | S | $CH_2CHCF_2$ | 525.2392 |
| 17 | R | S | phenyl-$CH_2$ | 539.2747 |
| 18 | R | S | 2-pyridyl-$CH_2$ | 540.2715 |
| 19 | R | S | (tetrahydrofuran-2-yl)-$CH_2$ | 533.2858 |
| 20 | R | S | (tetrahydrofuran-2-yl)-$CH_2$ | 533.2858 |
| 21 | R | S | $H_2N$-$CH_2$ | 492.2712 |
| 22 | R | S | $iPrO$-$CH_2$ | 535.3008 |
| 23 | R | S | $MeO$-$CH_2CH_2$ | 521.2856 |
| 24 | R | S | $MeS$-$CH_2$ | 523.2440 |
| 25 | R | S | $MeSO_2$-$CH_2$ | 555.2379 |
| 26 | R | S | $(CH_2)_2OCF_3$ | 561 |
| 27 | R | S | cyclopropyl-$OCH_2$ | 533.2850 |
| 28 | R | S | $HO$-$CH(CH_3)$-$CH_2$ | 507.2703 |

TABLE E-1-continued

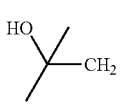

| Examples | C-3 | C-6 | R¹ | MS (M + 1) |
|---|---|---|---|---|
| 29 | R | S | HO-C(CH₃)₂-CH₂- | 521.2867 |
| 30 | R | S | H₂N-C(CH₃)₂-CH₂- | 506.2395 |
| 31 | R | S | HO-C(CF₃)(CH₃)-CH₂- | 561.2395 |
| 32 | R | S | (tetrahydrofuran-3-yl)CH₂- | 533.2821 |
| 33 | R | S | Ph | 525.2569 |
| 34 | R | S | Me₂N-C(O)-CH₂- | 534.2791 |

Example 35

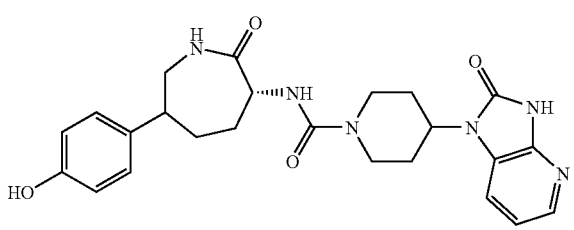

N-[(3R)-6-(4-Hydroxyphenyl)-2-oxoazepan-3-yl]-4-(2-oxo-2,3-dihydro-1H-imidazo[4,5-b]pyridin-1-yl)piperidine-1-carboxamide Triethylamine (0.009 mL, 0.091 mmol) was added to a solution of (3R)-3-amino-6-(4-hydroxyphenyl)azepan-2-one (10 mg, 0.045 mmol) and 4-nitrophenyl chloroformate (18 mg, 0.091 mmol) in N,N-dimethylformamide (0.2 mL) and tetrahydrofuran (0.2 mL) at 0° C. After 1 h, 2-oxo-1-(4-piperidinyl)-2,3-dihydro-1H-imidazo[4,5-b]pyridine dihydrochloride (26 mg, 0.091 mmol) and diisopropylethylamine (0.032 mL, 0.182 mmol) were added and the mixture was allowed to warm to ambient temperature. After 18 h, the mixture was purified by reverse phase HPLC (C-18, 95% water/acetonitrile→5% water/acetonitrile with 0.1% trifluoroacetic acid) to give the title compound (7 mg). MS 465.2243 (M+1).

Essentially following the procedures outlined for the preparation of Examples 1-35, the Examples in Table E-2 were prepared.

TABLE E-2

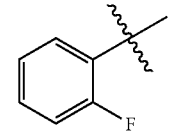

| Examples | C-6 | R¹ | R² | MS (M + 1) |
|---|---|---|---|---|
| 36 | R or S | H | 2-fluorophenyl | 467.2189 |
| 37 | S | H | 2-fluorophenyl | 467.2200 |
| 38 | R or S | H | 3-fluorophenyl | 467.2201 |
| 39 | R or S | H | 4-fluorophenyl | 467.2203 |
| 40 | R or S | H | 2,3-difluorophenyl | 485.2076 |
| 41 | R | H | 2,3-difluorophenyl | 485.2090 |

TABLE E-2-continued

| Examples | C-6 | R¹ | R² | MS (M + 1) |
|---|---|---|---|---|
| 42 | R or S | H | 2-pyridyl | 450 |
| 43 | R or S | H | 3-pyridyl | 450.2241 |
| 44 | R or S | H | 4-pyridyl | 450.2262 |
| 45 | R or S | cyclopropyl-CH₂ | 3-hydroxyphenyl | 519 |
| 46 | S | cyclopropyl-CH₂ | 3-hydroxyphenyl | 519 |
| 47 | S | cyclopropyl-CH₂ | 1H-pyrazol-3-yl | 493 |
| 48 | R | cyclopropyl-CH₂ | 1H-pyrazol-3-yl | 493 |
| 49 | R or S | H | 3,5-difluorophenyl | 485.2123 |
| 50 | R or S | H | 2,5-difluorophenyl | 485.2118 |
| 51 | R or S | H | 2-(trifluoromethyl)phenyl | 517.2165 |
| 52 | R or S | H | 2-methylphenyl | 463.2428 |
| 53 | R or S | H | 3-methylphenyl | 463.2431 |
| 54 | R or S | H | 4-methylphenyl | 463.2434 |
| 55 | R or S | H | 2-chlorophenyl | 483.1894 |
| 56 | S | H | 2-chlorophenyl | 483.1907 |

TABLE E-2-continued
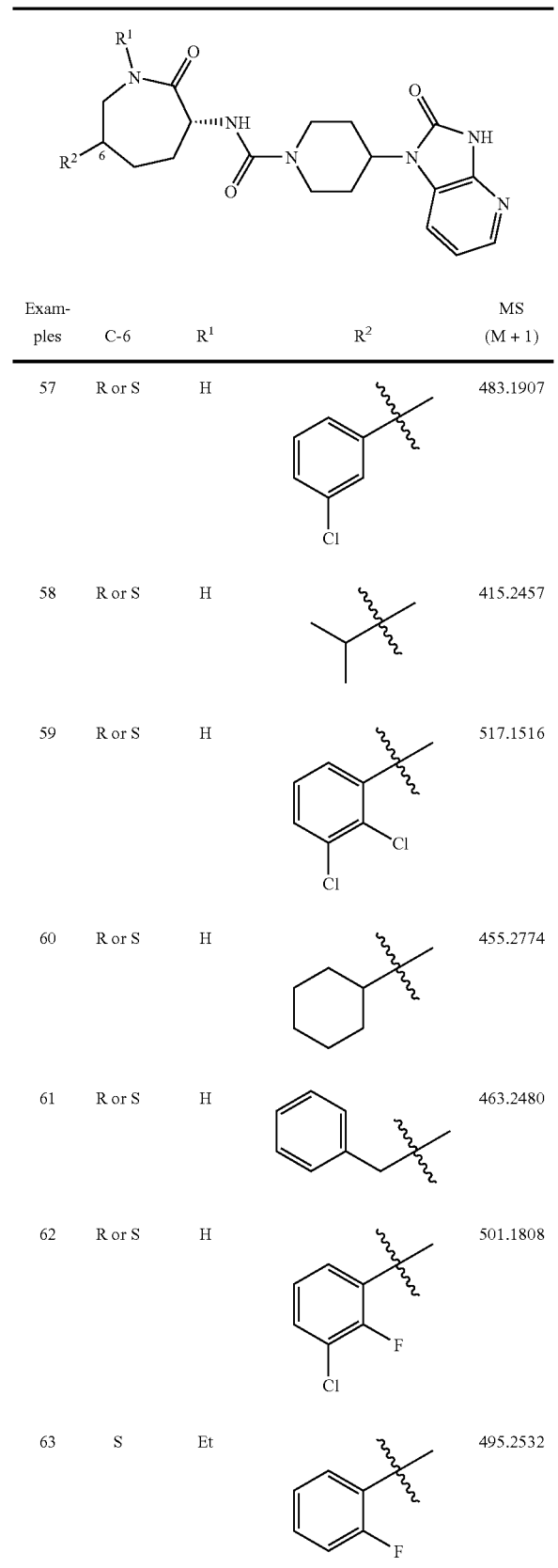
| Examples | C-6 | R¹ | R² | MS (M + 1) |
|---|---|---|---|---|
| 57 | R or S | H | 3-Cl-phenyl | 483.1907 |
| 58 | R or S | H | isopropyl | 415.2457 |
| 59 | R or S | H | 2,3-diCl-phenyl | 517.1516 |
| 60 | R or S | H | cyclohexyl | 455.2774 |
| 61 | R or S | H | benzyl | 463.2480 |
| 62 | R or S | H | 3-Cl-2-F-phenyl | 501.1808 |
| 63 | S | Et | 2-F-phenyl | 495.2532 |
TABLE E-2-continued
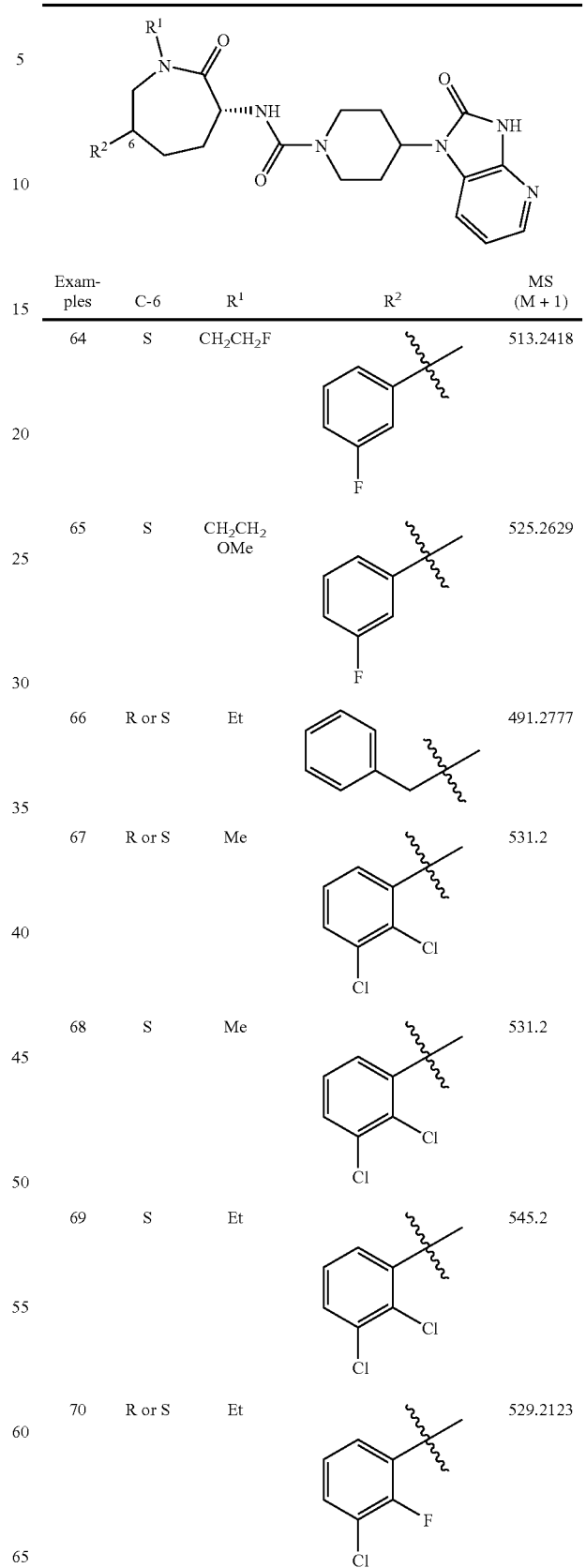
| Examples | C-6 | R¹ | R² | MS (M + 1) |
|---|---|---|---|---|
| 64 | S | CH₂CH₂F | 3-F-phenyl | 513.2418 |
| 65 | S | CH₂CH₂OMe | 3-F-phenyl | 525.2629 |
| 66 | R or S | Et | benzyl | 491.2777 |
| 67 | R or S | Me | 2,3-diCl-phenyl | 531.2 |
| 68 | S | Me | 2,3-diCl-phenyl | 531.2 |
| 69 | S | Et | 2,3-diCl-phenyl | 545.2 |
| 70 | R or S | Et | 3-Cl-2-F-phenyl | 529.2123 |

TABLE E-2-continued

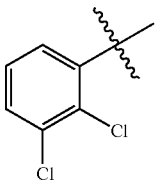

| Examples | C-6 | R¹ | R² | MS (M + 1) |
|---|---|---|---|---|
| 71 | R or S | CH₂CF₃ | 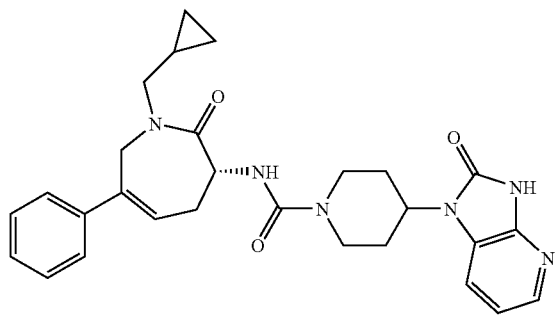 | 599.1538 |

Example 72

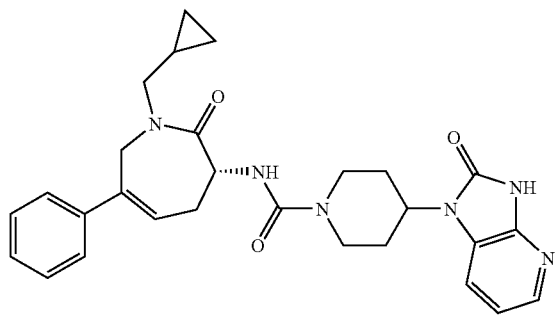

N-[(3R)-1-(Cyclopropylmethyl)-2-oxo-6-phenyl-2,3,4,7-tetrahydro-1H-azepin-3-yl]-4-(2-oxo-2,3-dihydro-1H-imidazo[4,5-b]pyridin-1-yl)piperidine-1-carboxamide The title compound was prepared using similar procedures to Examples 1-35. MS 501 (M+1).

Example 73

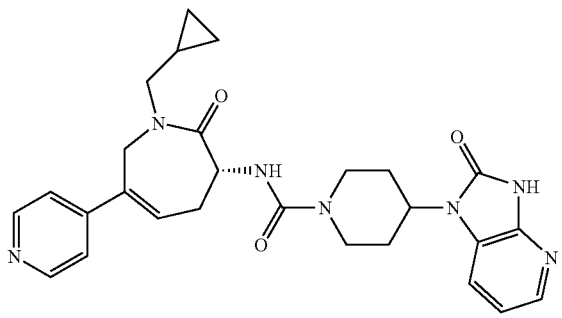

N-[(3R)-1-(Cyclopropylmethyl)-2-oxo-6-pyridin-4-yl-2,3,4,7-tetrahydro-1H-azepin-3-yl]-4-(2-oxo-2,3-dihydro-1H-imidazo[4,5-b]pyridin-1-yl)piperidine-1-carboxamide The title compound was prepared using similar procedures to Examples 1-35. MS 502 (M+1).

Example 74

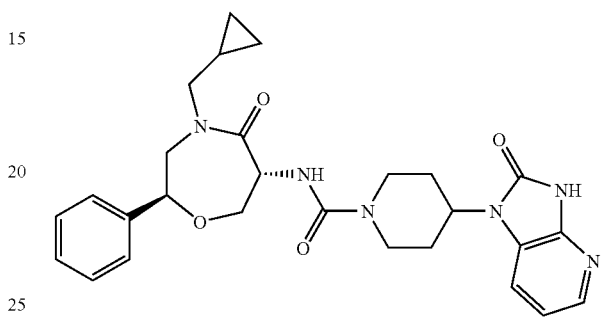

N-[(2S,6R)-4-(Cyclopropylmethyl)-5-oxo-2-phenyl-1,4-oxazepan-6-yl]-4-(2-oxo-2,3-dihydro-1H-imidazo[4,5-b]pyridin-1-yl)piperidine-1-carboxamide Triethylamine (0.015 mL, 0.109 mmol) was added to a solution of (2S,6R)-6-amino-4-(cyclopropylmethyl)-2-phenyl-1,4-oxazepan-5-one (27 mg, 0.104 mmol) and 4-nitrophenyl chloroformate (22 mg, 0.109 mmol) in tetrahydrofuran (2 mL) at 0° C. After 0.5 h, diisopropylethylamine (0.072 mL, 0.415 mmol), 2-oxo-1-(4-piperidinyl)-2,3-dihydro-1H-imidazo[4,5-b]pyridine dihydrochloride (36 mg, 0.124 mmol), and dichloromethane (2.5 mL) were added and the mixture warmed to ambient temperature. After 18 h, the mixture was concentrated. Purification by silica gel chromatography (100% dichloromethane→95% dichloromethane/methanol) gave the title compound (45 mg). MS 505.2559 (M+1).

Example 75

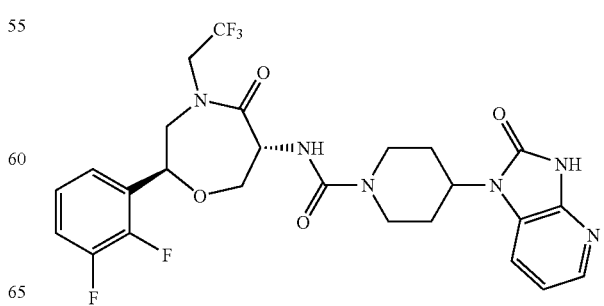

N-[(2S,6R)-2-(2,3-difluorophenyl)-5-oxo-4-(2,2,2-trifluoroethyl)-1,4-oxazepan-6-yl]-4-(2-oxo-2,3-dihydro-1H-imidazo[4,5-b]pyridin-1-yl)piperidine-1-carboxamide The title compound was prepared with using a similar procedure to Example 74. MS 569.1943 (M+1).

Example 76

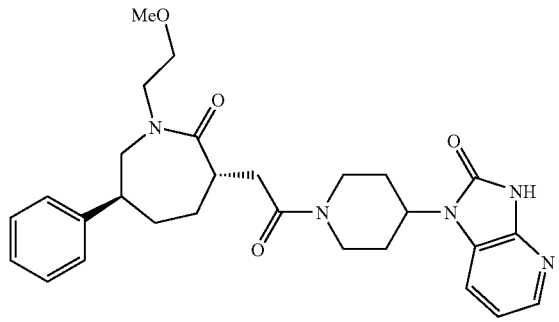

trans-1-(1-{[1-(2-Methoxyethyl)-2-oxo-6-phenylazepan-3-yl]acetyl}piperidin-4-yl)-2-oxo-2,3-dihydro-1H-imidazo[4,5-b]pyridin-4-ium trifluoroacetate

Step A. Trans-[1-(2-methoxyethyl)-2-oxo-6-phenylazepan-3-yl]acetic acid

Trifluoroacetic acid (1 mL) was added to a solution (trans)-tert-butyl[1-(2-methoxyethyl)-2-oxo-6-phenylazepan-3-yl]acetate (170 mg, 0.47 mmol) in dichloromethane (3 mL). After 2 h, the solution was concentrated. MS 306 (M+1).

Step B. trans-1-(1-{[1-(2-Methoxyethyl)-2-oxo-6-phenylazepan-3-yl]acetyl}piperidin-4-yl)-2-oxo-2,3-dihydro-1H-imidazo[4,5-b]pyridin-4-ium trifluoroacetate Triethylamine (0.33 mL, 2.35 mmol) was added to a solution of trans-[1-(2-methoxyethyl)-2-oxo-6-phenylazepan-3-yl]acetic acid (143.6 mg, 0.47 mmol), 2-oxo-1-(4-piperidinyl)-2,3-dihydro-1H-imidazo[4,5-b]pyridine dihydrochloride (136 mg, 0.47 mmol), 1-[3-(dimethylamino)propyl]-3-ethylcarbodiimide hydrochloride (180 mg, 0.941 mmol), and 1-hydroxybenzotriazole hydrate (72 mg, 0.47 mmol) in N,N-dimethylformamide (4 mL). After 18 h, the reaction was concentrated. Purification by reverse phase HPLC (C-18, 95% water/acetonitrile→5% water/acetonitrile with 0.1% trifluoroacetic acid) gave the title compound (187 mg). MS 506 (M+1).

Example 77

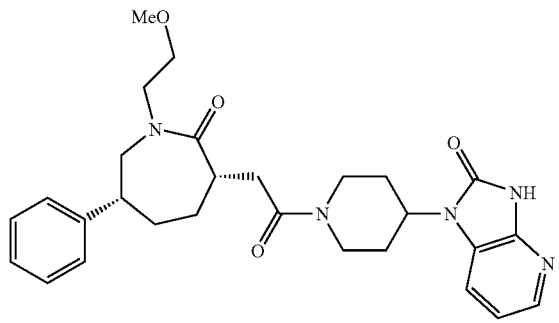

cis-1-(1-{[1-(2-Methoxyethyl)-2-oxo-6-phenylazepan-3-yl]acetyl}piperidin-4-yl)-2-oxo-2,3-dihydro-1H-imidazo[4,5-b]pyridin-4-ium trifluoroacetate The title compound was prepared with (cis)-tert-butyl[1-(2-methoxyethyl)-2-oxo-6-phenylazepan-3-yl]acetate using a similar procedure to Example 76. MS 506 (M+1).

Essentially following the procedures outlined for the preparation of Example 76, the Examples in Table E-3 were prepared.

TABLE E-3

| Examples | C-3 | C-6 | R¹ | MS (M + 1) |
|---|---|---|---|---|
| 78 | R | S | ▷—CH₂ | 502.2813 |
| 79 | S | R | ▷—CH₂ | 502 |
| 80 | R | R | ▷—CH₂ | 502 |
| 81 | S | S | ▷—CH₂ | 502 |

Example 82

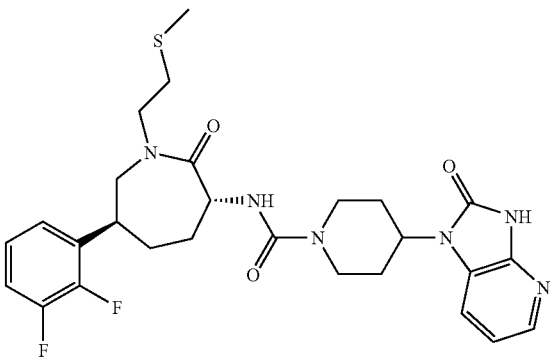

N-(3R,6S)-6-(2,3-Difluorophenyl)-1-[2-(methylthio)ethyl]-2-oxoazepan-3-yl-4-(2-oxo-2,3-dihydro-1H-imidazo[4,5-b]pyridin-1-yl)piperidine-1-carboxamide Triethylamine (0.020 mL, 0.143 mmol) was added to a solution of (3R,6S)-3-amino-6-(2,3-difluorophenyl)-1-[2-(methylthio)ethyl]azepan-2-one (45 mg, 0.143 mmol) and 4-nitrophenyl chloroformate (29 mg, 0.143 mmol) in tetrahydrofuran (3 mL) at 0° C. After 15 min, 2-oxo-1-(4-piperidinyl)-2,3-dihydro-1H-imidazo[4,5-b]pyridine dihydrochloride (46 mg, 0.157 mmol), triethylamine (0.080 mL, 0.572 mmol) and dichloromethane (5 mL) were added and the mixture was heated to 50° C. After 30 min, the mixture was allowed to cool to ambient temperature and concentrated. Purification by silica gel chromatography [100% dichloromethane→95% dichloromethane/methanol (10% ammonium hydroxide/methanol)] gave the title compound (60 mg). The title compound was converted to the HCl salt with 2M HCl in ether. MS 559.2 (M+1). $^1$H NMR (500 MHz, CD$_3$OD) δ 8.11 (dd, J=7.8 Hz, 1.0 Hz, 1H), 7.99 (dd, J=6.1 Hz, 1.0 Hz, 1H), 7.38-7.35 (m, 1H), 7.18-7.14 (m, 3H), 4.76 (d, J=10.7 Hz, 1H), 4.61-4.54 (m, 1H), 4.31-4.26 (m, 2H), 4.15-4.09 (m, 1H), 3.85-3.80 (m, 1H), 3.67-3.58 (m, 1H), 3.37 (d, J=15.4 Hz, 1H), 3.20-3.16 (m, 1H), 3.08-2.96 (m, 2H), 2.75-2.70 (m, 2H), 2.49-2.41 (m, 1H), 2.34-2.26 (m, 1H), 2.21-2.16 (m, 1H), 2.14 (s, 3H), 2.11-2.07 (m, 2H), 1.90-1.85 (m, 3H).

Example 83

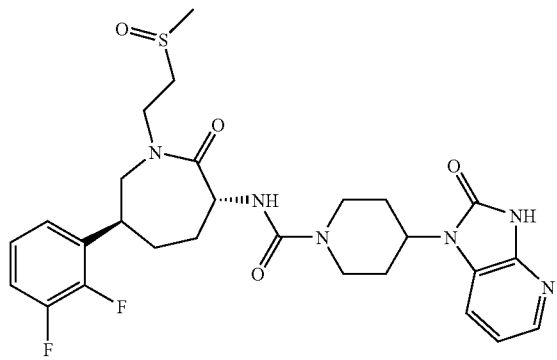

N-{(3R,6S)-6-(2,3-Difluorophenyl)-1-[2-(methylsulfinyl)ethyl]-2-oxoazepan-3-yl}-4-(2-oxo-2,3-dihydro-1H-imidazo[4,5-b]pyridin-1-yl)piperidine-1-carboxamide Triethylamine (0.010 mL, 0.027 mmol) was added to a solution of (3R,6S)-3-amino-6-(2,3-difluorophenyl)-1-[2-(methylsulfinyl)ethyl]azepan-2-one (8.9 mg, 0.027 mmol) and 4-nitrophenyl chloroformate (5.4 mg, 0.027 mmol) in tetrahydrofuran (0.700 mL) at 0° C. After 45 min, 2-oxo-1-(4-piperidinyl)-2,3-dihydro-1H-imidazo[4,5-b]pyridine dihydrochloride (7.9 mg, 0.027 mmol) and triethylamine (0.040 mL, 0.108 mmol) were added and the mixture allowed to warm to ambient temperature. After 16 h, the mixture was concentrated. Purification by reverse phase HPLC (C-18, 95% water/acetonitrile→5% water/acetonitrile with 0.1% trifluoroacetic acid) gave the title compound. MS 575 (M+1).

Example 84

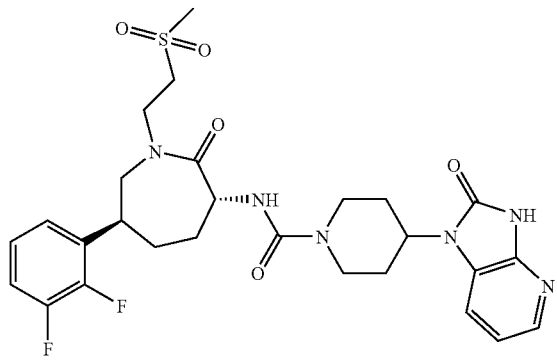

N-{(3R,6S)-6-(2,3-Difluorophenyl)-1-[2-(methylsulfonyl)ethyl]-2-oxoazepan-3-yl}-4-(2-oxo-2,3-dihydro-1H-imidazo[4,5-b]pyridin-1-yl)piperidine-1-carboxamide Triethylamine (0.010 mL, 0.023 mmol) was added to a solution of (3R,6S)-3-amino-6-(2,3-difluorophenyl)-1-[2-(methylsulfonyl)ethyl]azepan-2-one (8 mg, 0.023 mmol) and 4-nitrophenyl chloroformate (4.6 mg, 0.023 mmol) in tetrahydrofuran (0.700 mL) at 0° C. After 15 min, 2-oxo-1-(4-piperidinyl)-2,3-dihydro-1H-imidazo[4,5-b]pyridine dihydrochloride (6.7 mg, 0.023 mmol) and triethylamine (0.040 mL, 0.092 mmol) were added and the mixture allowed to warm to ambient temperature. After 16 h, the mixture was concentrated. Purification by reverse phase HPLC (C-18, 95% water/acetonitrile→5% water/acetonitrile with 0.1% trifluoroacetic acid) gave the title compound. MS 591 (M+1).

Example 85

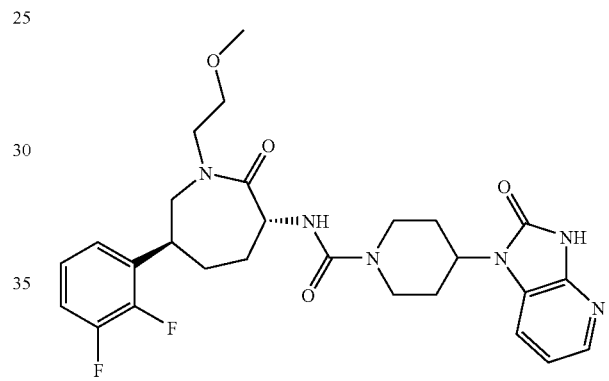

N-[(3R,6S)-6-(2,3-Difluorophenyl)-1-(2-methoxyethyl)-2-oxoazepan-3-yl]-4-(2-oxo-2,3-dihydro-1H-imidazo[4,5-b]pyridin-1-yl)piperidine-1-carboxamide Triethylamine (0.030 mL, 0.218 mmol) was added to a solution of (3R,6S)-3-amino-6-(2,3-difluorophenyl)-1-(2-methoxyethyl)azepan-2-one (65 mg, 0.218 mmol) and 4-nitrophenyl chloroformate (44 mg, 0.218 mmol) in tetrahydrofuran (3 mL) at 0° C. After 30 min, 2-oxo-1-(4-piperidinyl)-2,3-dihydro-1H-imidazo[4,5-b]pyridine dihydrochloride (70 mg, 0.240 mmol), triethylamine (0.120 mL, 0.872 mmol), and dichloromethane (5 mL) were added and the mixture allowed to warm to ambient temperature. After 4.5 h, the mixture was concentrated. Purification by silica gel chromatography [100% dichloromethane→95% dichloromethane/methanol (10% ammonium hydroxide/methanol)] gave the title compound (88 mg). The title compound was converted to the HCl salt with 2M HCl in ether. MS 543.3 (M+1). $^1$H NMR (500 MHz, CD$_3$OD) δ 8.09 (dd, J=7.8 Hz, 1.0 Hz, 1H), 7.99 (dd, J=6.1 Hz, 1.0 Hz, 1H), 7.36 (m, 1H), 7.17-7.10 (m, 3H), 4.78 (d, J=11.0 Hz, 1H), 4.61-4.54 (m, 1H), 4.31-4.24 (m, 2H), 4.18-4.13 (m, 1H), 3.94-3.89 (m, 1H), 3.57-3.53 (m, 2H), 3.48-3.43 (m, 1H), 3.39 (d, J=15.1 Hz, 1H), 3.34 (s, 3H), 3.19-3.15 (m, 1H), 3.07-2.96 (m, 2H), 2.49-2.41 (m, 1H), 2.35-2.26 (m, 1H), 2.19-2.06 (m, 3H), 1.90-1.76 (m, 3H).

Example 86

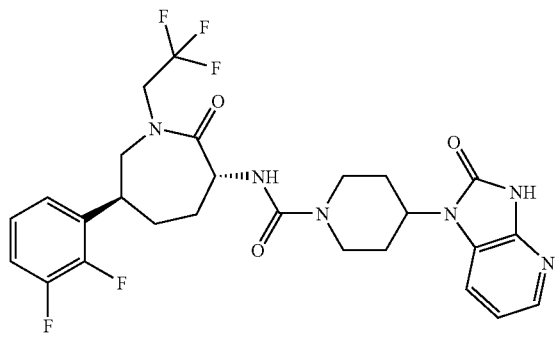

N-[(3R,6S)-6-(2,3-Difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide Triethylamine (0.038 mL, 0.276 mmol) was added to a solution of (3R,6S)-3-amino-6-(2,3-difluorophenyl)-1-(2,2,2-trifluoroethyl)azepan-2-one (89 mg, 0.276 mmol) and 4-nitrophenyl chloroformate (56 mg, 0.276 mmol) in tetrahydrofuran (3 mL) at 0° C. After 30 min, 2-oxo-1-(4-piperidinyl)-2,3-dihydro-1H-imidazo[4,5-b]pyridine dihydrochloride (88 mg, 0.304 mmol), triethylamine (0.152 mL, 1.104 mmol), and dichloromethane (5 mL) were added and the mixture allowed to warm to ambient temperature. After 48 h, the mixture was concentrated. Purification by silica gel chromatography [100% dichloromethane→95% dichloromethane/methanol (10% ammonium hydroxide/methanol)] gave the title compound (98 mg). The title compound was converted to the HCl salt with 2M HCl in ether. MS 567.2 (M+1). $^1$H NMR (500 MHz, CD$_3$OD) δ 8.11 (dd, J=7.8 Hz, 1.0 Hz, 1H), 8.00 (dd, J=5.9 Hz, 1.0 Hz, 1H), 7.34-7.31 (m, 1H), 7.19-7.13 (m, 3H), 4.86-4.83 (m, 1H), 4.62-4.57 (m, 1H), 4.49-4.41 (m, 1H), 4.33-4.25 (m, 3H), 4.12-4.04 (m, 1H), 3.51-3.46 (m, 1H), 3.18-3.14 (m, 1H), 3.09-2.96 (m, 2H), 2.51-2.44 (m, 1H), 2.33-2.25 (m, 1H), 2.22-2.10 (m, 3H), 1.90-1.81 (m, 3H).

Example 87

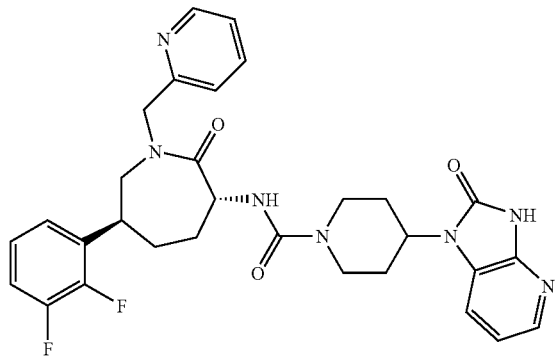

N-[(3R,6S)-6-(2,3-Difluorophenyl)-2-oxo-1-(pyridin-2-ylmethyl)azepan-3-yl]-4-(2-oxo-2,3-dihydro-1H-imidazo[4,5-b]pyridin-1-yl)piperidine-1-carboxamide Triethylamine (0.065 mL, 0.468 mmol) was added to a solution of (3R,6S)-3-amino-6-(2,3-difluorophenyl)-1-(pyridin-2-ylmethyl)azepan-2-one (180 mg, 0.417 mmol) and 4-nitrophenyl chloroformate (94 mg, 0.468 mmol) in tetrahydrofuran (3 mL) at 0° C. After 1 h, 2-oxo-1-(4-piperidinyl)-2,3-dihydro-1H-imidazo[4,5-b]pyridine dihydrochloride (136 mg, 0.468 mmol) and triethylamine (0.195 mL, 1.404 mmol) were added and the mixture allowed to warm to ambient temperature. After 18 h, the mixture was partitioned between ethyl acetate and water. The organic layer was washed with water (2×), saturated brine, dried over magnesium sulfate, filtered and concentrated. Purification by silica gel chromatography [100% dichloromethane→95% dichloromethane/methanol (10% ammonium hydroxide/methanol)] gave the title compound (240 mg). The title compound was converted to the HCl salt with 2M HCl in ether. MS 576.3 (M+1). $^1$H NMR (500 MHz, CD$_3$OD) δ 8.78 (d, J=5.9 Hz, 1H), 8.62-8.59 (m, 1H), 8.07 (d, J=8.3 Hz, 1H), 8.03-7.98 (m, 3H), 7.32 (dd, J=8.1 Hz, 6.1, 1H), 7.18-7.15 (m, 3H), 5.43 (d, J=16.9 Hz, 1H), 4.75 (d, J=17.1 Hz, 1H), 4.56-4.51 (m, 1H), 4.36-4.28 (m, 3H), 3.51 (d, J=15.1 Hz, 1H), 3.48 (s, 1H), 3.22-3.17 (m, 1H), 3.05-2.98 (m; 2H), 2.44-2.40 (m, 1H), 2.34-2.23 (m, 2H), 2.18-2.14 (m, 2H), 1.97-1.92 (m, 1H), 1.89-1.88 (m, 2H).

Example 88

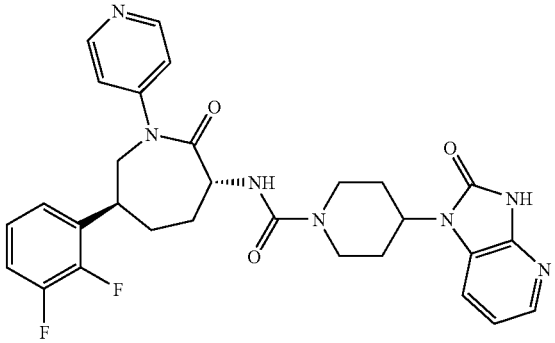

N-[(3R,6S)-6-(2,3-Difluorophenyl)-2-oxo-1-pyridin-4-ylazepan-3-yl]-4-(2-oxo-2,3-dihydro-1H-imidazo[4,5-b]pyridin-1-yl)piperidine-1-carboxamide Triethylamine (0.018 mL, 0.132 mmol) was added to a solution of (3R,6S)-3-amino-6-(2,3-difluorophenyl)-1-pyridin-4-ylazepan-2-one (42 mg, 0.132 mmol) and 4-nitrophenyl chloroformate (27 mg, 0.132 mmol) in tetrahydrofuran (2 mL) at 0° C. After 1 h, 2-oxo-1-(4-piperidinyl)-2,3-dihydro-1H-imidazo[4,5-b]pyridine dihydrochloride (38 mg, 0.132 mmol) and triethylamine (0.054 mL, 0.396 mmol) were added and the mixture allowed to warm to ambient temperature. After 18 h, the mixture was partitioned between ethyl acetate and water. The organic layer was washed with water (2×), saturated brine, dried over magnesium sulfate, filtered and concentrated. Purification by silica gel chromatography [100% dichloromethane→95% dichloromethane/methanol (10% ammonium hydroxide/methanol)] gave the title compound (53 mg). The title compound was converted to the HCl salt with 2M HCl in ether. MS 562.2 (M+1). $^1$H NMR (500

MHz, CD₃OD) δ 8.76 (d, J=7.6 Hz, 2H), 8.11 (d, J=7.3 Hz, 2H), 8.00 (d, J=6.4 Hz, 2H), 7.30 (t, J=7.0 Hz, 1H), 7.27-7.21 (m, 3H), 5.11 (d, J=11.5 Hz, 1H), 4.72-4.65 (m, 1H), 4.60-4.55 (m, 1H), 4.35-4.33 (m, 2H), 4.14 (d, J=16.1 Hz, 1H), 3.42-3.39 (m, 1H), 3.09-3.02 (m, 2H), 2.47-2.44 (m, 1H), 2.37-2.30 (m, 2H), 2.24-2.18 (m, 2H), 2.06-2.03 (m, 1H), 1.91 (br. s, 2H).

Example 89

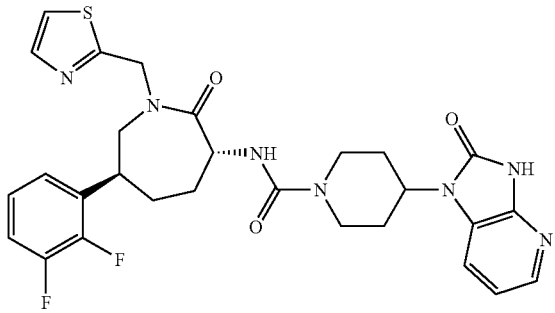

N-[(3R,6S)-6-(2,3-Difluorophenyl)-2-oxo-1-(1,3-thiazol-2-ylmethyl)azepan-3-yl]-4-(2-oxo-2,3-dihydro-1H-imidazo[4,5-b]pyridin-1-yl)piperidine-1-carboxamide Triethylamine (0.156 mL, 0.1.12 mmol) was added to a solution of (3R,6S)-3-amino-6-(2,3-difluorophenyl)-1-(1,3-thiazol-2-ylmethyl)azepan-2-one (302 mg, 0.895 mmol) and 4-nitrophenyl chloroformate (217 mg, 1.074 mmol) in tetrahydrofuran (15 mL) at 0° C. After 30 min, 2-oxo-1-(4-piperidinyl)-2,3-dihydro-1H-imidazo[4,5-b]pyridine dihydrochloride (782 mg, 2.685 mmol), triethylamine (5.37 mmol) and dichloromethane (15 mL) were added and the mixture allowed to warm to ambient temperature. The reaction was stirred overnight, concentrated, diluted with saturated aqueous sodium bicarbonate and extracted with dichloromethane (2×). The organic layer was washed with water, saturated brine, dried over magnesium sulfate, filtered and concentrated. Purification by silica gel chromatography (0% →8% methanol/dichloromethane) gave the title compound (400 mg). MS 582.2109 (M+1). ¹H NMR (500 MHz, CDCl₃) δ 8.06 (d, J=4.5 Hz, 1H), 7.73 (d, J=3.4 Hz, 1H), 7.35 (m, 2H), 7.0 (m, 2H), 6.98 (dd, J=5.4, 7.8 Hz, 1H), 6.85 (m, 1H), 6.21 (d, J=5.3 Hz, 1H), 5.0 (app q, J=15 Hz, 2H), 4.85 (dd, J=5.0, 11.1 Hz, 1H), 4.58 (m, 1H), 4.27 (br dd, 2H), 4.00 (dd, J=10.6, 15.1 Hz, 1H), 3.50 (d, J=15.1 Hz, 1H), 3.0 (br dd, 1H), 2.88 (dd, J=10.0, 10.0 Hz, 1H), 2.2-1.6 (m, 8H).

Example 90

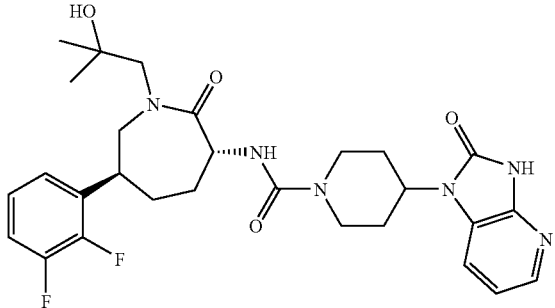

N-[(3R,6S)-6-(2,3-difluorophenyl)-1-(2-hydroxy-2-methylpropyl)-2-oxoazepan-3-yl]-4-(2-oxo-2,3-dihydro-1H-imidazo[4,5-b]pyridin-1-yl)piperidine-1-carboxamide Triethylamine (0.054 mL, 0.389 mmol) was added to a solution of (3R,6S)-3-amino-6-(2,3-difluorophenyl)-1-(2-hydroxy-2-methylpropyl)azepan-2-one (54 mg, 0.173 mmol) and 4-nitrophenyl chloroformate (40 mg, 0.199 mmol) in tetrahydrofuran (15 mL) at 0° C. After 30 min, 2-oxo-1-(4-piperidinyl)-2,3-dihydro-1H-imidazo[4,5-b]pyridine dihydrochloride (151 mg, 0.519 mmol), triethylamine (1.04 mmol) and chloroform (15 mL) were added and the mixture allowed to warm to ambient temperature. The reaction was then heated to 50° C. for 2 h, concentrated, diluted with saturated aqueous sodium bicarbonate and extracted with dichloromethane (2×). The organic layer was washed with water, saturated brine, dried over magnesium sulfate, filtered and concentrated. Purification by silica gel chromatography (1.5%→11% methanol/dichloromethane) gave the title compound (70 mg). MS 557.2653 (M+1). ¹H NMR (500 MHz, CDCl₃) δ 8.03 (d, J=4.8 Hz, 1H), 7.34 (d, J=7.7 Hz, 1H), 7.1 (m, 2H), 7.0-6.9 (m, 2H), 6.17 (d, J=5.1 Hz, 1H), 4.84 (dd, J=10.9, 5.0 Hz, 1H), 4.5 (m, 1H), 4.3 (br dd, 2H), 4.02 (dd, J=10.1, 15.1 Hz, 1H), 3.76 (d, J=14.1 Hz, 1H), 3.42 (d, J=15.1 Hz, 1H), 3.31 (d; J=14.1 Hz, 1H), 3.15-2.95 (m, 4H), 2.3-1.9 (m, 8H), 1.26 (s, 3H), 1.24 (s, 3H).

Essentially following the procedures outlined for the preparation of Examples 82-90, the Examples in Table E-4 were prepared.

TABLE E-4

| Example | R | MS (M + 1) |
|---|---|---|
| 91 | CH₃ | 499.2 |
| 92 | CH₂CH₃ | 513.2 |
| 93 | cyclopropyl-CH₂ | 539.3 |
| 94 | CH₂CH₂F | 531.1 |
| 95 | CH₂CHF₂ | 549.1 |
| 96 | (S)-tetrahydrofuran-2-ylmethyl | 569.3 |
| 97 | (R)-tetrahydrofuran-2-ylmethyl | 569.3 |
| 98 | CH₂CO₂CH₃ | 557.2287 |

TABLE E-4-continued

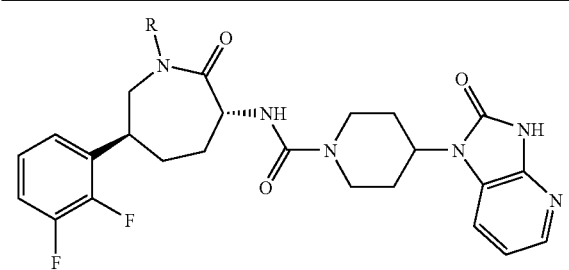

| Example | R | MS (M + 1) |
|---|---|---|
| 99 | phenyl | 561.2 |
| 100 | pyridin-3-yl | 562.2 |
| 101 | 4-SO₂CH₃-phenyl | 639.2 |
| 102 | 3-SO₂CH₃-phenyl | 639.2 |
| 103 | 6-methoxy-2-methylpyridin-3-yl | 606.3 |
| 104 | isoxazol-3-ylmethyl | 566.2344 |
| 105 | CH(CH₃)₂ | 527.2545 |
| 106 | (1-methylimidazol-2-yl)methyl | 579.2658 |
| 107 | (1-methylpyrazol-3-yl)methyl | 579.2656 |
| 108 | (1-methylpyrazol-5-yl)methyl | 579.2657 |

TABLE E-4-continued

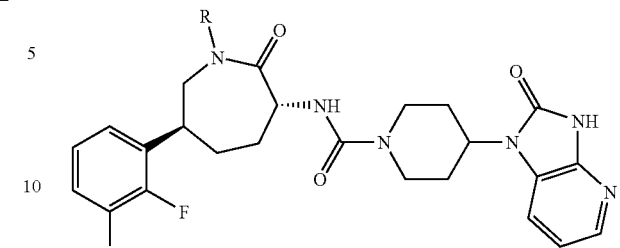

| Example | R | MS (M + 1) |
|---|---|---|
| 109 | 2-(thiazol-2-yl)propan-2-yl | 596.2242 |
| 110 | pyridin-3-ylmethyl | 576.2496 |
| 111 | pyridin-4-ylmethyl | 576.2499 |
| 112 | isopropoxyethyl | 571 |
| 113 | methoxyethyl | 557.2 |
| 114 | cyclopropylmethoxymethyl | 569.2651 |
| 115 | trifluoromethoxyethyl | 597.2193 |
| 116 | CH₂CO₂H | 543.2163 |
| 117 | (1-oxido-pyridin-2-yl)methyl | 592.2433 |
| 118 | CH₂CH₂SO₂CH₃ | 591.2169 |
| 119 | pyrrolidin-1-ylethyl | 582.2972 |
| 120 | morpholin-4-ylethyl | 598.2944 |
| 121 | (CH₃)₂NCH₂CH₂ | 556.2834 |
| 122 | CH₂CO₂CH(CH₃)₂ | 585 |
| 123 | H₂NCH₂CH₂ | 528.3 |

TABLE E-4-continued
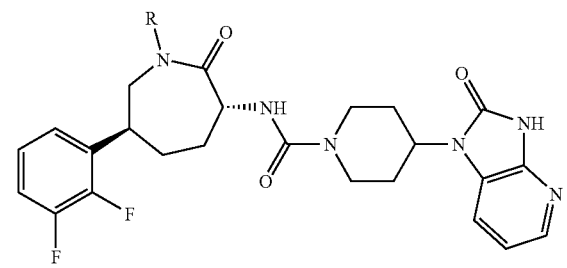
| Example | R | MS (M + 1) |
|---|---|---|
| 124 | 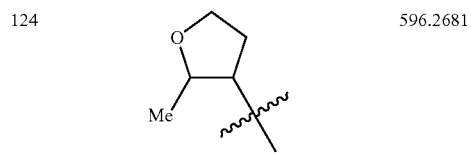 | 596.2681 |
| 125 | 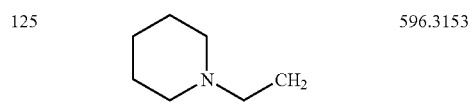 | 596.3153 |
| 126 | 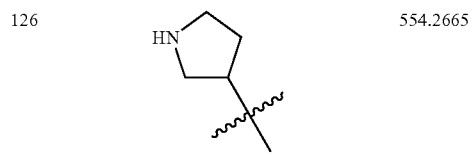 | 554.2665 |
| 127 | 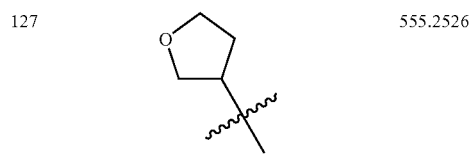 | 555.2526 |
| 128 | 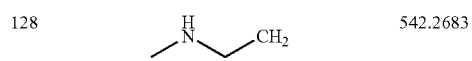 | 542.2683 |
| 129 | 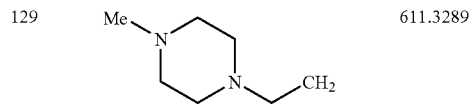 | 611.3289 |
| 130 | 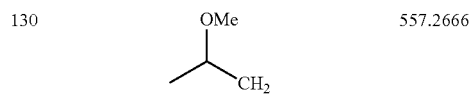 | 557.2666 |
| 131 | $CH_2CH_2CF_3$ | 581.2296 |
| 132 | 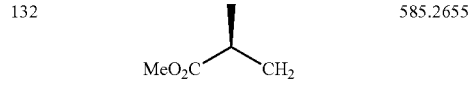 | 585.2655 |
| 133 | 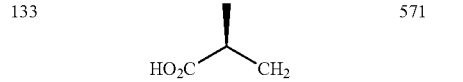 | 571 |
| 134 | 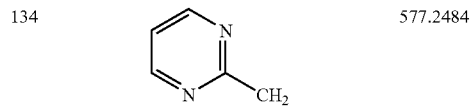 | 577.2484 |
TABLE E-4-continued
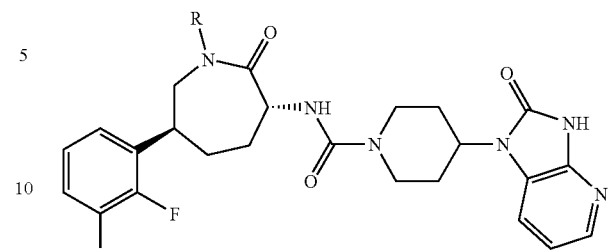
| Example | R | MS (M + 1) |
|---|---|---|
| 135 | 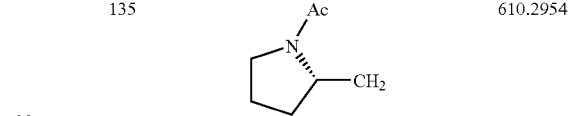 | 610.2954 |
| 136 | 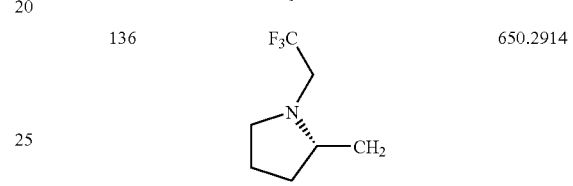 | 650.2914 |
| 137 | 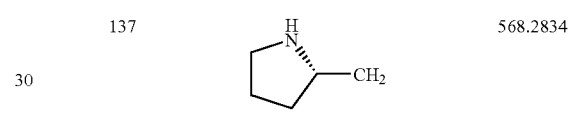 | 568.2834 |
| 138 | 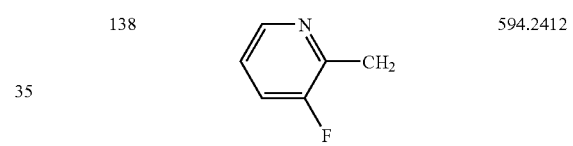 | 594.2412 |
| 139 | 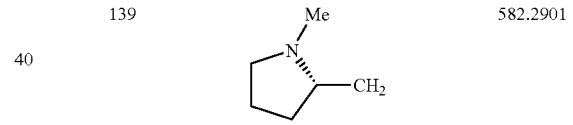 | 582.2901 |
| 140 | $CH_2CH_2OH$ | 529.2383 |
| 141 | 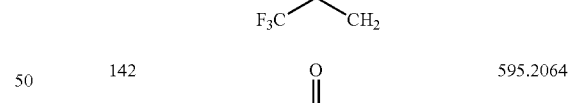 | 597.2244 |
| 142 | 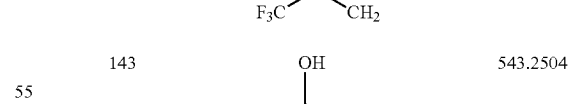 | 595.2064 |
| 143 | 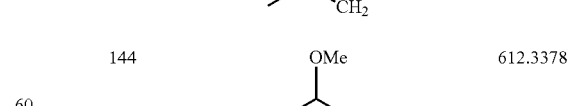 | 543.2504 |
| 144 | 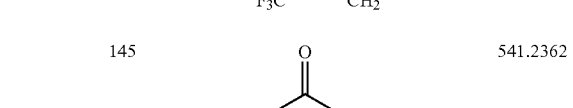 | 612.3378 |
| 145 |  | 541.2362 |

Example 146

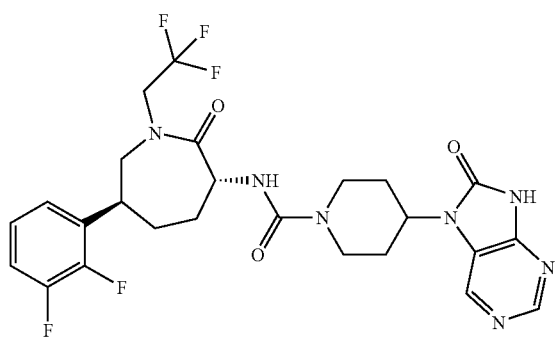

N-[(3R,6S)-6-(2,3-Difluorophenyl)-2-oxo-1-(2,2,2-trifluoroethyl)azepan-3-yl]-4-(8-oxo-8,9-dihydro-7H-purin-7-yl)piperidine-1-carboxamide Triethylamine (0.030 mL, 0.215 mmol) was added to a solution of (3R,6S)-3-amino-6-(2,3-difluorophenyl)-1-(2,2,2-trifluoroethyl)azepan-2-one (80 mg, 0.248 mmol) and 4-nitrophenyl chloroformate (44 mg, 0.218 mmol) in tetrahydrofuran (3 mL) at 0° C. After 0.5 h, 7-piperidin-4-yl-7,9-dihydro-8H-purin-8-one hydrochloride (73 mg, 0.248 mmol) and triethylamine (0.120 mL, 0.860 mmol) were added and the mixture allowed to warm to ambient temperature. After 18 h, the mixture was partitioned between ethyl acetate and water. The organic layer was washed with water (2×), saturated brine, dried over magnesium sulfate, filtered and concentrated. Purification by silica gel chromatography (100% dichloromethane→95% dichloromethane/methanol) gave the title compound (114 mg). MS 567.2123 (M+1).

Essentially following the procedures outlined for the preparation of Example 146, the Examples in Table E-5 were prepared.

TABLE E-5

| Example | R | MS (M + 1) |
|---|---|---|
| 147 | CH₃ | 500.2182 |
| 148 | cyclopropyl-CH₂ | 540.2493 |
| 149 | CH₂CHF₂ | 550.2159 |
| 150 | CH₂CH₂OCF₃ | 598.2147 |
| 151 | CH₂CH₂SCH₃ | 560.2217 |
| 152 | CH₂CH₂SOCH₃ | 576.2174 |
| 153 | CH₂CH₂SO₂CH₃ | 592.2 |
| 154 | CH₂CH₂OCH₃ | 544.2473 |
| 155 | CH₂CH₂OH | 530.2336 |
| 156 | phenyl | 562.2338 |
| 157 | F₃C-CH(OMe)-CH₂ | 612.2349 |

Example 158

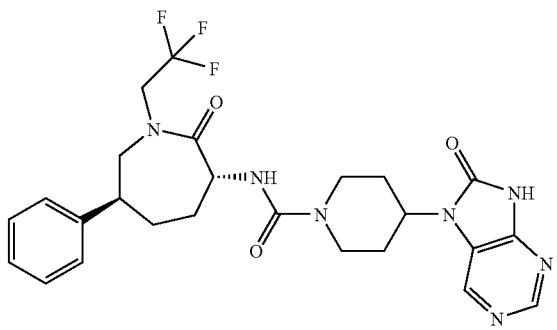

N-[(3R,6S)-6-Phenyl-2-oxo-1-(2,2,2-trifluoroethyl)azeyan-3-yl]-4-(8-oxo-8,9-dihydro-7H-purin-7-yl)piperidine-1-carboxamide Prepared essentially following the procedure outlined for the preparation of Example 146. MS 532.2250 (M+1).

Example 159

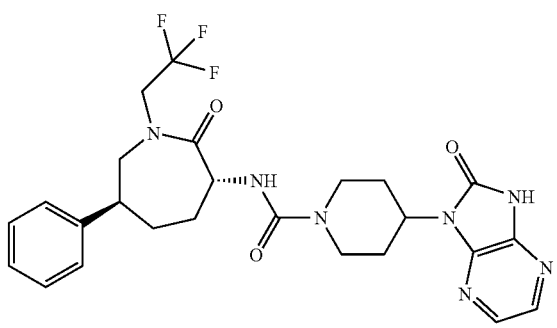

115

4-(2-oxo-2,3-dihydro-1H-imidazo[4,5-b]pyrazin-1-yl)-N-[(3R,6S)-2-oxo-6-phenyl-1-(2,2,2-trifluoroethyl)azepan-3-yl]piperidine-1-carboxamide Prepared essentially following the procedure outlined for the preparation of Example 146. MS 532.2292 (M+1).

Example 160

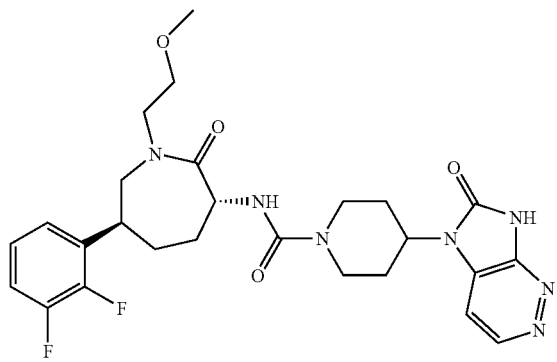

N-[(3R,6S)-6-(2,3-Difluorophenyl)-1-(2-methoxyethyl)-2-oxoazepan-3-yl]-4-(6-oxo-6,7-dihydro-5H-imidazo[4,5-c]pyridazin-5-yl)piperidine-1-carboxamide Prepared essentially following the procedure outlined for the preparation of Example 146. MS 544.2465 (M+1).

Example 161

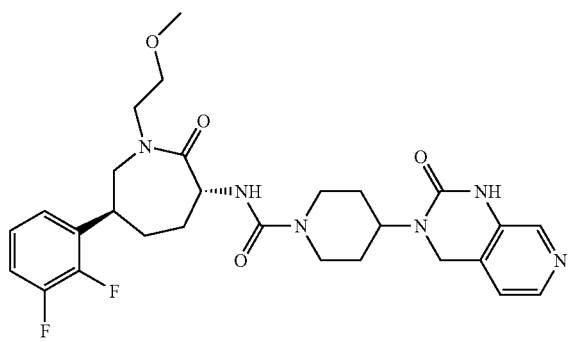

116

N-[(3R,6S)-6-(2,3-Difluorophenyl)-1-(2-methoxyethyl)-2-oxoazepan-3-yl]-4-(2-oxo-1,4-dihydropyrido[3,4-d]pyrimidin-3(2H)-yl)piperidine-1-carboxamide Prepared essentially following the procedure outlined for the preparation of Example 146. MS 557.2645

Example 162

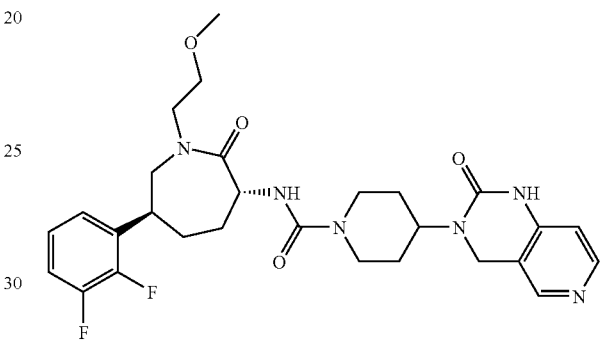

N-[(3R,6S)-6-(2,3-Difluorophenyl)-1-(2-methoxyethyl)-2-oxoazepan-3-yl]-4-(2-oxo-1,4-dihydropyrido[4,3-d]pyrimidin-3(2H)-yl)piperidine-1-carboxamide Prepared essentially following the procedure outlined for the preparation of Example 146 MS 557.2683

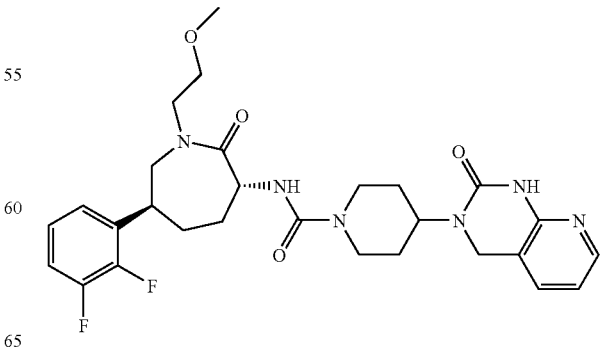

N-[(3R,6S)-6-(2,3-Difluorophenyl)-1-(2-methoxy-ethyl)-2-oxoazepan-3-yl]-4-(2-oxo-1,4-dihydropyrido[2,3-d]pyrimidin-3(2H)-yl)piperidine-1-carboxamide Prepared essentially following the procedure outlined for the preparation of Example 146. MS 557.2701

Example 164

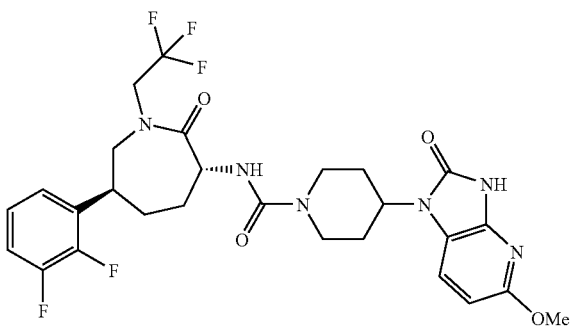

N-[(3R,6S)-6-(2,3-Difluorophenyl)-2-oxo-1-(2,2,2-trifluoroethyl)azepan-3-yl]-4-(5-methoxy-2-oxo-2,3-dihydro-1H-imidazo[4,5-b]pyridin-1-yl)piperidine-1-carboxamide Prepared essentially following the procedure outlined for the preparation of Example 146. MS 597.2228 (M+1).

Example 165

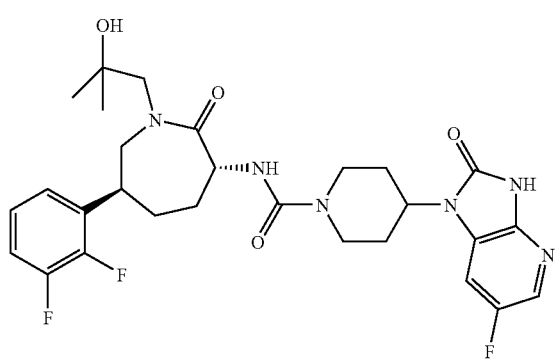

N-[(3R,6S)-6-(2,3-Difluorophenyl)-1-(2-hydroxy-2-methylpropyl)-2-oxoazepan-3-yl]-4-(6-fluoro-2-oxo-2,3-dihydro-1H-imidazo[4,5-b]pyridin-1-yl)piperidine-1-carboxamide Prepared essentially following the procedure outlined for the preparation of Example 146. MS 575.2584 (M+1).

Example 166

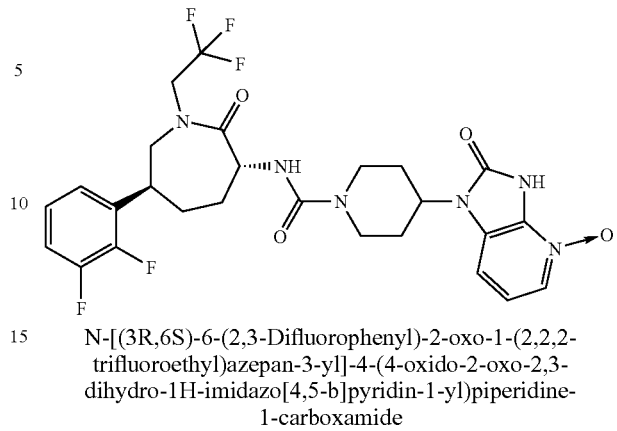

N-[(3R,6S)-6-(2,3-Difluorophenyl)-2-oxo-1-(2,2,2-trifluoroethyl)azepan-3-yl]-4-(4-oxido-2-oxo-2,3-dihydro-1H-imidazo[4,5-b]pyridin-1-yl)piperidine-1-carboxamide Prepared essentially following the procedure outlined for the preparation of Example 146. MS 583.2076 (M+1).

Example 167

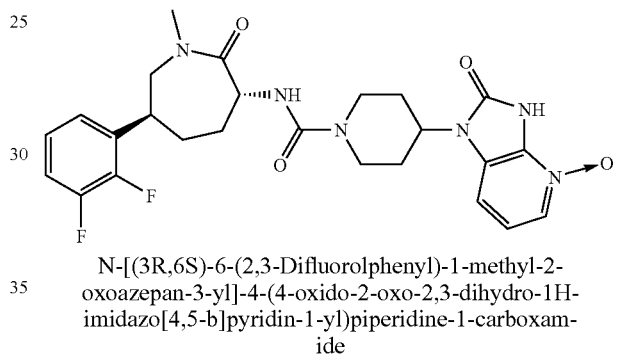

N-[(3R,6S)-6-(2,3-Difluorolphenyl)-1-methyl-2-oxoazepan-3-yl]-4-(4-oxido-2-oxo-2,3-dihydro-1H-imidazo[4,5-b]pyridin-1-yl)piperidine-1-carboxamide Prepared essentially following the procedure outlined for the preparation of Example 146. MS 515.2205 (M+1).

Example 168

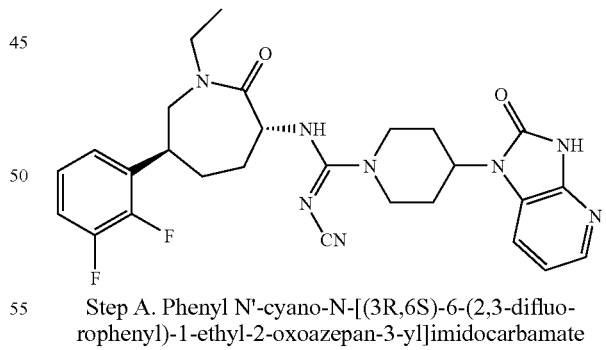

Step A. Phenyl N'-cyano-N-[(3R,6S)-6-(2,3-difluorophenyl)-1-ethyl-2-oxoazepan-3-yl]imidocarbamate A solution of (3R,6S)-3-amino-6-(2,3-difluorophenyl)-1-ethylazepan-2-one (135 mg, 0.503 mmol) in dichloromethane was treated N,N-diisopropylethylamine (65 mg, 0.503 mmol) and diphenyl N-cyanocarbonimidate (204 mg, 0.855 mmol). After 5 h, the reaction was quenched with 0.5N NaOH and the organic layer washed with water and brine. The combined aqueous layers were extracted with EtOAc. The combined organics were dried, filtered and concentrated. Purification by silica gel chromatography (EtOAc/hexanes) gave the title compound (166 mg). MS 413.3 (M+1).

Step B. N'-Cyano-N-[(3R,6S)-6-(2,3-difluorophenyl)-1-ethyl-2-oxoazepan-3-yl]-4-(2-oxo-2,3 dihydro-1H-imidazo[4,5-b]pyridin-1-yl)piperidine-1-carboximidamide A solution of phenyl N'-cyano-N-[(3R,6S)-6-(2,3-difluorophenyl)-1-ethyl-2-oxoazepan-3-yl]imidocarbamate (166 mg, 0.402 mmol) and 2-oxo-1-(4-piperidinyl)-2,3-dihydro-1H-imidazo[4,5-b]pyridine dihydrochloride (116 mg, 0.402 mmol), in 1-pentanol (10 mL) was treated with N,N-diisopropylethylamine (52 mg, 0.402 mmol). This mixture was heated to reflux for 24 h. Concentration and purification by silica gel chromatography (0%→10% methanol/dichloromethane) followed by reverse phase HPLC (C-18, 95% water/acetonitrile→5% water/acetonitrile with 0.1% trifluoroacetic acid) gave the title compound (10 mg). MS 537.5 (M+1).

Example 169

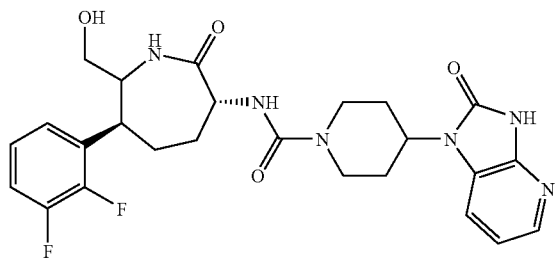

N-[(3R,6S)-6-(2,3-Difluorophenyl)-7-(hydroxymethyl)-2-oxoazepan-3-yl]-4-(2-oxo-2,3-dihydro-1H-imidazo[4,5-b]pyridin-1-yl)piperidine-1-carboxamide

Step A. Benzyl (2R,5S)-2-[bis(tert-butoxycarbonyl)amino]-5-(2,3-difluorophenyl)-7-hydroxy-6-nitroheptanoate To a solution of (5S)—N,N-bis(tert-butoxycarbonyl)-5-(2,3-difluorophenyl)-6-nitro-D-norleucinate (2.30 g, 3.975 mmol) and 1,1,3,3-tetramethylguanidine (46 mg, 0.40 mmol) in acetonitrile (20 mL) was added formaldehyde (0.15 mL, 37% aqueous solution). After stirring for 60 min, more formaldehyde (0.050 mL, 37% aqueous solution) was added. After stirring for an additional 60 min the mixture was diluted with saturated aqueous NaHCO$_3$ and extracted with CH$_2$Cl$_2$ (3×). The combined organics were dried over magnesium sulfate, filtered and concentrated to give a residue that was purified by silica gel chromatography (25%→75% ethyl acetate/hexanes) to give the title compound (1.44 g,). MS 409.1 (M+1-2Boc).

Step B. (5S)—N$^2$,N$^2$-bis(tert-Butoxycarbonyl)-5-(2,3-difluorophenyl)-6-(hydroxymethyl)-D-lysine A solution of benzyl (2R,5S)-2-[bis(tert-butoxycarbonyl)amino]-5-(2,3-difluorophenyl)-7-hydroxy-6-nitroheptanoate (180 mg, 0.49 mmol) and 10% Pd/C (300 mg) in EtOH (5 mL, SureSeal from Aldrich), was hydrogenated at 55 psi for 7 d (200 mg more Pd/C was added after 3 d). The reaction was filtered through Celite with more EtOH and concentrated to afford the title compound (180 mg). MS 489.1 (M+1).

Step C. Di-tert-butyl [(3R,6S)-6-(2,3-difluorophenyl)-7-(hydroxymethyl)-2-oxoazepan-3-yl]imidodicarbonate To a solution (5S)—N$^2$,N$^2$-bis(tert-butoxycarbonyl)-5-(2,3-difluorophenyl)-6-(hydroxymethyl)-D-lysine (180 mg, 0.37 mmol) in DCM (5 mL) were added EDC (106 mg, 0.55 mmol) and HOAT (50 mg, 0.37 mmol). After 30 min, NaHCO$_3$ was added, the layers separated and the aqueous phase backwashed with DCM. The combined organics were dried over magnesium sulfate, filtered and concentrated and the residue purified by silica gel chromatography (0%→10% MeOH/DCM) to give the title compound (100 mg). MS 471.1 (M+1).

Step D. (3R,6S)-3-amino-6-(2,3-difluorophenyl)-7-(hydroxymethyl)azepan-2-one Di-tert-butyl [(3R,6S)-6-(2,3-difluorophenyl)-7-(hydroxymethyl)-2-oxoazepan-3-yl]imidodicarbonate (100 mg, 0.213 mmol) was diluted DCM (30 mL) and TFA (8 mL) was added. After 2 h, the reaction was concentrated to give the title compound as its TFA salt (57 mg). MS 271.0 (M+1).

Step E. N-[(3R,6S)-6-(2,3-difluorophenyl)-7-(hydroxymethyl)-2-oxoazepan-3-yl]-4-(2-oxo-2,3-dihydro-1H-imidazo[4,5-b]pyridin-1-yl)piperidine-1-carboxamide Triethylamine (0.68 mL, 0.49 mmol) was added to a solution of (3R,6S)-3-amino-6-(2,3-difluorophenyl)-7-(hydroxymethyl)azepan-2-one (57 mg, 0.21 mmol) and 4-nitrophenyl chloroformate (47 mg, 0.23 mmol) in tetrahydrofuran (10 mL) at 0° C. After 30 min, 2-oxo-1-(4-piperidinyl)-2,3-dihydro-1H-imidazo[4,5-b]pyridine dihydrochloride (98 mg, 0.34 mmol), triethylamine (0.84 mmol) and chloroform (10 mL) were added and the mixture allowed to warm to ambient temperature. The reaction was stirred overnight, concentrated, diluted with saturated aqueous sodium bicarbonate and extracted with dichloromethane (2×). The organic layer was washed with water, saturated brine, dried over magnesium sulfate, filtered and concentrated. Purification by silica gel chromatography (1%→12% methanol/dichloromethane) gave the title compound (17 mg). MS 515.2203 (M+1).

Example 170

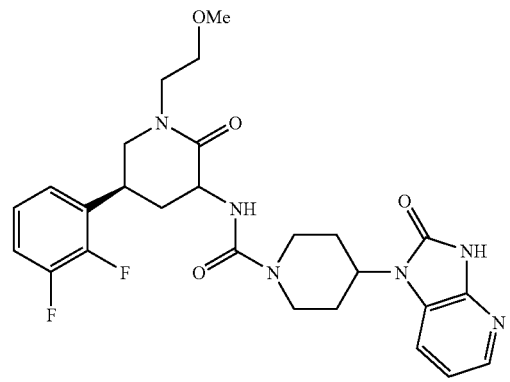

N-[5-(2,3-Difluorophenyl)-1-(2-methoxyethyl)-2-oxopiperidin-3-yl]-4-(2-oxo-2,3-dihydro-1H-imidazo[4,5-b]pyridin-1-yl)piperidine-1-carboxamide

Step A. 5-Bromo-1-(2-methoxyethyl)-3-nitropyridin-2(1H)-one

Cesium carbonate (14.88 g, 45.66 mmol) was added to a solution of 5-bromo-3-nitropyridin-2-ol (10.0 g, 45.7 mmol) and 2-bromoethyl methyl ether (4.29 mL, 45.66 mmol) in N,N-dimethylformamide (400 mL). After 3 h, additional 2-bromoethyl methyl ether (4.29 mL, 45.7 mmol) was added, and the reaction was heated to 60° C. After 4 h, water was added. The mixture was extracted with ethyl acetate (3×), and the combined organic extracts were washed with saturated brine, dried over sodium sulfate, filtered and concentrated. Purification by silica gel chromatography (100% hexanes→40% ethyl acetate/hexanes) gave the title compound (7.39 g). MS 277 (M).

Step B. 5-(2,3-Difluorophenyl)-1-(2-methoxyethyl)-3-nitropyridin-2(1H)-one

Palladium acetate (41.0 mg, 0.18 mmol) was added to a solution of 5-bromo-1-(2-methoxyethyl)-3-nitropyridin-2(1H)-one (500 mg, 1.81 mmol), 2,3-difluorophenyl boronic acid (570 mg, 3.61 mmol), diisopropylamine (0.759 mL, 5.41 mmol) and 3,3',3"-phosphinidynetris(benzenesulfonic acid) trisodium salt (310 mg, 0.541 mmol), in N,N-dimethylformamide (15 mL) and water (5 mL) and heated to 80° C. After 2 h, the mixture was allowed to cool to ambient temperature and filtered. Purification by reverse phase HPLC (C-18, 95% water/acetonitrile→5% water/acetonitrile with 0.1% trifluoroacetic acid) gave the title compound (335 mg). MS 311 (M+1). $^1$H NMR (500 MHz, CDCl$_3$) δ 8.56 (d, J=2.7 Hz, 1H), 8.03 (d, J=2.4 Hz, 1H), 7.23-7.18 (m, 2H), 7.15-7.12 (m, 1H), 4.33 (t, J=4.8 Hz, 2H), 3.74 (t, J=4.8 Hz, 2H), 3.35 (s, 3H).

Step C. 3-Amino-5-(2,3-difluorophenyl)-1-(2-methoxyethyl)piperridin-2-one

10% Platinum on carbon (320 mg) was added to a solution of 5-(2,3-difluorophenyl)-1-(2-methoxyethyl)-3-nitropyridin-2(1H)-one (300 mg, 0.967 mmol) in acetic acid (10 mL). The reaction vessel was evacuated and back-filled with nitrogen (3×), then back-filled with hydrogen (56 psi). After 65 h, the mixture was filtered and concentrated. MS 285 (M+1).

Step D. N-[5-(2,3-Difluorophenyl)-1-(2-methoxyethyl)-2-oxopiperidin-3-yl]-4-(2-oxo-2,3-dihydro-1H-imidazo[4,5-b]pyridin-1-yl)piperidine-1-carboxamide Triethylamine (83 µL, 0.598 mmol) was added to a solution of 3-amino-5-(2,3-difluorophenyl)-1-(2-methoxyethyl)piperidin-2-one (170 mg, 0.598 mmol) and 4-nitrophenylchloroformate (121 mg, 0.598 mmol) in tetrahydrofuran (4 mL) at 0° C. After 1 h, 2-oxo-1-(4-piperidinyl)-2,3-dihydro-1H-imidazo[4,5-b]pyridine dihydrochloride (174 mg, 0.651 mmol), triethylamine (249 µL, 1.794 mmol) were added and the mixture allowed to warm to ambient temperature. After 18 h, saturated aqueous sodium bicarbonate was added and the mixture was extracted with ethyl acetate. The organic layer was washed with saturated aqueous sodium bicarbonate (3×), saturated brine, dried over sodium sulfate, filtered and concentrated. Purification by silica gel chromatography [100% dichloromethane→95% dichloromethane/5% (10% ammonium hydroxide/methanol)] gave the title compound (0.135 g). MS 529.2353 (M+1). $^1$H NMR (500 MHz, CDCl$_3$) δ 8.03 (dd, J=5.3, 1.1 Hz, 1H), 7.38 (dd, J=7.8, 1.2 Hz, 1H), 7.11-7.03 (m, 2H), 7.01-6.96 (m, 2H), 5.82 (d, J=3.4 Hz, 1H), 4.58-4.53 (m, 1H), 4.34-4.30 (m, 1H), 4.23 (d, J=6.6 Hz, 2H), 3.71-3.62 (m, 3H), 3.60-3.53 (m, 3H), 3.52-3.46 (m, 1H), 3.33 (s, 3H), 2.96 (dd, J=23.4, 10.5 Hz, 2H), 2.80-2.78 (m, 1H), 2.28-2.21 (m, 2H), 1.90 (dd, J=10.5, 2.0 Hz, 2H).

Essentially following the procedures outlined for the preparation of Example 170, the Examples in Table E-6 were prepared.

TABLE E-6

| Examples | C-3 | C-5 | R$^1$ | R$^2$ | MS (M + 1) |
|---|---|---|---|---|---|
| 171 | R or S | R or S | CH$_2$CH$_2$OCH$_3$ | phenyl | 493.2519 |
| 172 | R or S | R or S | CH$_3$ | phenyl | 449.2285 |

TABLE E-6-continued
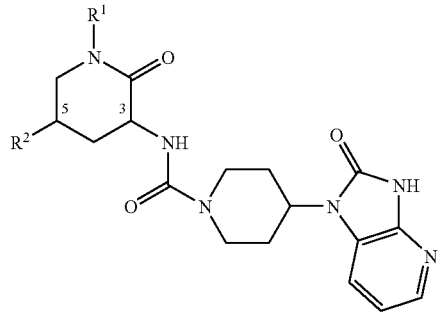
| Examples | C-3 | C-5 | R¹ | R² | MS (M + 1) |
|---|---|---|---|---|---|
| 173 | R or S | R or S | $CH_3$ | 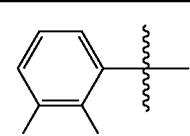 | 485.2098 |
| 174 | R or S | R or S | $CH_2CF_3$ | 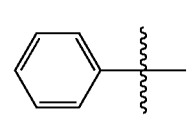 | 517.2154 |
| 175 | R or S | R or S | $CH_2CF_3$ | 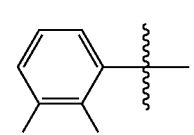 | 553.1962 |
| 176 | R | R | $CH_2CF_3$ | 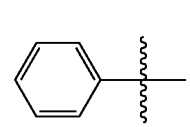 | 517 |
| 177 | R | S | $CH_2CF_3$ | 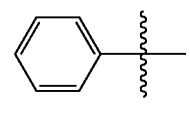 | 517 |
| 178 | S | R | $CH_2CF_3$ | 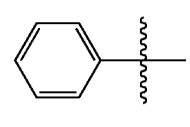 | 517 |
| 179 | S | S | $CH_2CF_3$ | 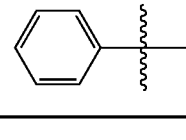 | 517 |

Example 180

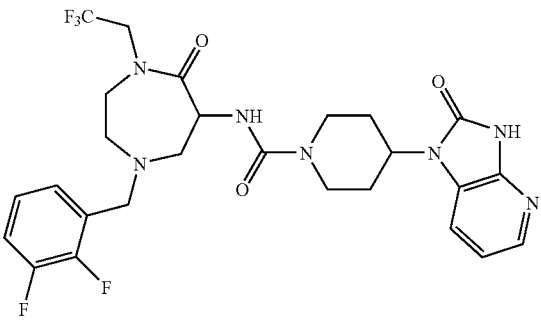

N-[1-(2,3-Difluorobenzyl)-5-oxo-4-(2,2,2-trifluoroethyl)-1,4-diazepan-6-yl]-4-(2-oxo-2,3-dihydro-1H-imidazo[4,5-b]pyridin-1-yl)piperidine-1-carboxamide

Step A: Benzyl 6-[(tert-butoxycarbonyl)amino]-5-oxo-1,4-diazepane-1-carboxylate Triethylamine (0.56 mL, 3.99 mmol) was added to a solution of benzyl-6-amino-5-oxo-1,4-diazepane-1-carboxylate (1.05 g, 3.99 mmol) and di-tert-butyl dicarbonate (1.31 g, 6.00 mmol) in dichloromethane (30 mL). After 18 h, water was added, and the mixture was extracted with ethyl acetate. The organic layer was washed with brine, dried over magnesium sulfate, filtered and concentrated. Purification by silica gel chromatography (100% dichloromethane→95% dichloromethane/methanol) gave the title compound (1.35 g). MS 364 (M+1).

Step B: Benzyl 6-[(tert-butoxycarbonyl)amino]-5-oxo-4-(2,2,2-trifluoroethyl)-1,4-diazepane-1-carboxylate Sodium hydride (60% dispersion in mineral oil; 180 mg, 4.43 mmol) was added to a solution of benzyl 6-[(tert-butoxycarbonyl)amino]-5-oxo-1,4-diazepane-1-carboxylate (1.34 g, 3.69 mmol) in N,N-dimethylformamide (25 mL) at −35° C. After 15 min, 2,2,2-trifluoroethyl trichloromethanesulfonate (0.911 mL, 5.54 mmol) was added and the reaction was stirred at −35° C. After 2 h, an additional amount of sodium hydride (100 mg, 2.5 mmol) and trichloromethanesulfonate (0.500 mL, 3.04 mmol) were added. After 18 h, the reaction was quenched with water and the mixture was extracted with ethyl acetate. The organic layer was washed with water (3×), saturated brine, dried over magnesium sulfate, filtered and concentrated. Purification by silica gel chromatography (hexanes→30% ethyl acetate/hexanes) gave the title compound (690 mg). MS 446 (M+1).

Step C: tert-Butyl 7-oxo-1-(2,2,2-trifluoroethyl)-1,4-diazepan-6-ylcarbamate 10% Palladium on carbon (77 mg) was added to a solution of benzyl 6-[(tert-butoxycarbonyl)amino]-5-oxo-4-(2,2,2-trifluoroethyl)-1,4-diazepane-1-carboxylate (590 mg, 1.32 mmol) in ethanol (20 mL). The reaction vessel was evacuated and back-filled with nitrogen (3×), then back-filled with hydrogen (1 atm). After 18 h, the mixture was filtered and concentrated to give. the title compound (420 mg). MS 312 (M+1). $^1$H NMR (500 MHz, CDCl$_3$) δ 5.83 (s, 1H), 4.53-4.49 (m, 1H), 4.29-4.20 (m, 1H), 3.96-3.88 (m, 1H), 3.81-3.77 (m, 1H), 3.38 (d, J=15.6 Hz, 1H), 3.26 (d, J=12.9 Hz, 1H), 3.16-3.13 (m, 1H), 2.81-2.79 (m, 1H), 2.72-2.67 (m, 1H), 1.83 (br s, 1H), 1.45 (s, 9H).

Step D. tert-Butyl 1-(2,3-difluorobenzyl)-5-oxo-4-(2,2,2-trifluoroethyl)-1,4-diazepan-6-ylcarbamate A mixture of tert-butyl 7-oxo-1-(2,2,2-trifluoroethyl)-1,4-diazepan-6-ylcarbamate (51 mg, 0.16 mmol), 2,3-difluorobenzaldehyde (0.053 mL, 0.49 mmol), and sodium cyanoborohydride (31 mg, 0.49 mmol) in methanol (5 mL) was adjusted to pH 4 with acetic acid. After 0.5 h, saturated aqueous sodium bicarbonate was added and the mixture was extracted with dichloromethane (3×). The combined organic extracts were dried over magnesium sulfate, filtered, and concentrated. Purification by silica gel chromatography [100% dichloromethane→95% dichloromethane/5% (10% ammonium hydroxide/methanol)] gave the title compound (62 mg). MS 438 (M+1).

Step E: 6-Amino-1-(2,3-difluorobenzyl-4-(2,2,2-trifluoroethyl)-1,4-diazepan-5-one Trifluoroacetic acid (2.5 mL) was added to a solution of tert-butyl 1-(2,3-difluorobenzyl)-5-oxo-4-(2,2,2-trifluoroethyl)-1,4-diazepan-6-ylcarbamate (62 mg, 0.142 mmol) in dichloromethane (5 mL). After 1 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated to give the title compound (45 mg). MS 338 (M+1).

Step F: N-[1-(2,3-Difluorobenzyl)-5-oxo-4-(2,2,2-trifluoroethyl)-1,4-diazepan-6-yl]-4-(2-oxo-2,3-dihydro-1H-imidazo[4,5-b]pyridin-1-yl)piperidine-1-carboxamide Triethylamine (0.012 mL, 0.133 mmol) was added to a solution of 6-amino-1-(2,3-difluorobenzyl)-4-(2,2,2-trifluoroethyl)-1,4-diazepan-5-one (45 mg, 0.133 mmol) and 4-nitrophenyl chloroformate (27 mg, 133 mmol) in tetrahydrofuran (2.5 mL) at 0° C. After 1 h, 2-oxo-1-(4-piperidinyl)-2,3-dihydro-1H-imidazo[4,5-b]pyridine dihydrochloride (43 mg, 0.147 mmol) and triethylamine (0.048 mL, 0.532 mmol) were added and the mixture allowed to warm to ambient temperature. After 18 h, the mixture was partitioned between ethyl acetate and water. The organic layer was washed with water (2×), saturated brine, dried over magnesium sulfate, filtered and concentrated. Purification by silica gel chromatography [100% dichloromethane→92% dichloromethane/methanol (10% ammonium hydroxide/methanol)] gave the title compound (67 mg). MS 582.2262 (M+1). $^1$H NMR (500 MHz, CDCl$_3$) δ 8.77 (s, 1H), 8.03 (d, J=5.4 Hz, 1H), 7.31 (d, J=8.1 Hz, 1H), 7.27-7.24 (m, 1H), 7.09-7.05 (m, 2H), 6.98 (dd, J=8.1, 5.4 Hz, 1H), 5.99 (d, J=4.9 Hz, 1H), 4.91-4.88 (m, 1H), 4.57-4.50 (m, 1H), 4.25-4.16 (m, 3H), 4.00-3.92 (m, 2H), 3.84 (dd, J=32.7, 14.2 Hz, 2H), 3.36-3.34 (m, 1H), 3.20 (d, J=12.5 Hz, 1H), 2.99-2.91 (m, 3H), 2.44-2.37 (m, 2H), 2.31-2.18 (m, 2H), 1.90 (d, J=11.0 Hz, 2H).

Essentially following the procedures outlined for the preparation of Example 180, the Examples in Table E-7 were prepared.

TABLE E-7

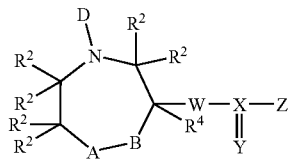

| Example | R² | MS (M + 1) |
|---------|-----|-----------|
| 181 | —CH₂—C₆H₅ | 546.2450 |
| 182 | H | 456.1983 |
| 183 | benzyloxycarbonyl group | 590.2295 |

What is claimed is:

1. A compound of Formula I:

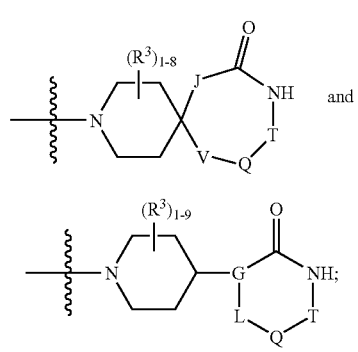

wherein:

Z is selected from:

Z1

Z2

A is $C(R^2)_2$;
B is $(C(R^2)_2)_n$;
D is selected from $R^1$, $OR^1$, $N(R^1)_2$, $NR^1C(O)R^1$, $C(O)R^1$, $S(O)_mR^1$, $C(O)OR^1$, $C(O)N(R^1)_2$, $C(O)NR^{10}R^{11}$, $C(NR^1)N(R^1)_2$, and $C(NR^1)R^1$;

$R^1$ is independently selected from:
1) H, $C_1$-$C_6$ alkyl, $C_2$-$C_6$ alkenyl, $C_2$-$C_6$ alkynyl, $C_{3\text{-}6}$ cycloalkyl, and heterocycle, unsubstituted or substituted with one or more substituents each independently selected from:
  a) $C_{1\text{-}6}$ alkyl,
  b) $C_{3\text{-}6}$ cycloalkyl,
  c) aryl, unsubstituted or substituted with 1-5 substituents each independently selected from $R^4$,
  d) heteroaryl, unsubstituted or substituted with 1-5 substituents each independently selected from $R^4$,
  e) heterocycle, unsubstituted or substituted with 1-5 substituents each independently selected from $R^4$,
  f) $(F)_pC_{1\text{-}3}$ alkyl,
  g) halogen,
  h) $OR^4$,
  i) $O(CH_2)_sOR^4$,
  j) $CO_2R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2NR^{10}R^{11}$,
  q) $N(R^{10})SO_2R^{11}$,
  r) $S(O)_mR^{10}$,
  s) CN,
  t) $NR^{10}R^{11}$,
  u) $N(R^{10})(CO)NR^4R^{11}$, and,
  v) $O(CO)R^4$, and
2) aryl or heteroaryl, unsubstituted or substituted with one or more substituents each independently selected from:
  a) $C_{1\text{-}6}$ alkyl,
  b) $C_{3\text{-}6}$ cycloalkyl,
  c) aryl, unsubstituted or substituted with 1-5 substituents each independently selected from $R^4$,
  d) heteroaryl, unsubstituted or substituted with 1-5 substituents each independently selected from $R^4$,
  e) heterocycle, unsubstituted or substituted with 1-5 substituents each independently selected from $R^4$,
  f) $(F)_pC_{1\text{-}3}$ alkyl,
  g) halogen,
  h) $OR^4$,
  i) $O(CH_2)_sOR^4$,
  j) $CO_2R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2NR^{10}R^{11}$,
  q) $N(R^{10})SO_2R^{11}$,
  r) $S(O)_mR^{10}$,
  s) CN,
  t) $NR^{10}R^{11}$,
  u) $N(R^{10})(CO)NR^4R^{11}$, and
  v) $O(CO)R^4$;

$R^1$ can be optionally joined to $R^2$ to form a 4-8 membered ring;

$R^2$ is independently selected from:
1) H, $C_0$-$C_6$ alkyl, $C_2$-$C_6$ alkenyl, $C_2$-$C_6$ alkynyl, $C_{3\text{-}6}$ cycloalkyl and heterocycle, unsubstituted or substituted with one or more substituents each independently selected from:
  a) $C_{1\text{-}6}$ alkyl,
  b) $C_{3\text{-}6}$ cycloalkyl, c) aryl, unsubstituted or substituted with 1-5 substituents where the substituents are independently selected from $R^4$,
d) heteroaryl, unsubstituted or substituted with 1-5 substituents each independently selected from $R^4$,
e) heterocycle, unsubstituted or substituted with 1-5 substituents each independently selected from $R^4$,
f) $(F)_p C_{1-3}$ alkyl,
g) halogen,
h) $OR^4$,
i) $O(CH_2)_s OR^4$,
j) $CO_2 R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2 NR^{10}R^{11}$,
q) $N(R^{10})SO_2 R^{11}$,
r) $S(O)_m R^{10}$,
s) CN,
t) $NR^{10}R^{11}$,
u) $N(R^{10})(CO)NR^4 R^{11}$, and,
v) $O(CO)R^4$, and
2) aryl or heteroaryl, unsubstituted or substituted with one or more substituents each independently selected from:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents each independently selected from $R^4$,
e) heterocycle, unsubstituted or substituted with 1-5 substituents each independently selected from $R^4$,
f) $(F)_p C_{1-3}$ alkyl,
g) halogen,
h) $OR^4$,
i) $O(CH_2)_s OR^4$,
j) $CO_2 R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2 NR^{10}R^{11}$,
q) $N(R^{10})SO_2 R^{11}$,
r) $S(O)_m R^{10}$,
s) CN,
t) $NR^{10}R^{11}$,
u) $N(R^{10})(CO)NR^4 R^{11}$, and
v) $O(CO)R^4$,
where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;
$R^{10}$ and $R^{11}$ are each independently selected from: H, $C_{1-6}$ alkyl, $(F)_p C_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl, and morpholinyl, which is ring is unsubstituted or substituted with 1-5 substituents each independently selected from $R^4$;
$R^4$ is independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;
W is O, $NR^4$ or $C(R^4)_2$;
X is C or S;
Y is O, $(R^4)_2$, NCN, $NSO_2 CH_3$ or $NCONH_2$, or Y is $O_2$ when X is S;
$R^6$ is independently selected from H and:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents each independently selected from $R^4$,
e) heterocycle, unsubstituted or substituted with 1-5 substituents each independently selected from $R^4$,
f) $(F)_p C_{1-3}$ alkyl,
g) halogen,
h) $OR^4$,
i) $O(CH_2)_s OR^4$,
j) $CO_2 R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2 NR^{10}R^{11}$,
q) $N(R^{10})SO_2 R^{11}$,
r) $S(O)_m R^{10}$,
s) CN,
t) $NR^{10}R^{11}$,
u) $N(R^{10})(CO)NR^4 R^{11}$, and
v) $O(CO)R^4$;
J is a bond, $C(R^6)_2$, O or $NR^6$;
V is selected from a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=N, $N(R^6)$—$C(R^6)_2$, N=$C(R^6)$, and $N(R^6)$—$N(R^6)$;
G-L is selected from: N, N—$C(R^6)_2$, C=$C(R^6)$, C=N, $C(R^6)$, $C(R^6)$—$C(R^6)_2$, $C(R^6)$—$C(R^6)_2$—$C(R^6)_2$, C=$C(R^6)$—$C(R^6)_2$, $C(R^6)$—$C(R^6)$=$C(R^6)$, $C(R^6)$—$C(R^6)_2$—$N(R^6)$, C=$C(R^6)$—$N(R^6)$, $C(R^6)$—$C(R^6)$=N, $C(R^6)$—$N(R^6)$—$C(R^6)_2$, C=N—$C(R^6)_2$, $C(R^6)$—N=$C(R^6)$, $C(R^6)$—$N(R^6)$—$N(R^6)$, C=N—$N(R^6)$, N—$C(R^6)_2$—$C(R^6)_2$, N—$C(R^6)$=$C(R^6)$, N—$C(R^6)_2$—$N(R^6)$, N—$C(R^6)$=N, N—$N(R^6)$—$C(R^6)_2$ and N—N=$C(R^6)$;
Q is selected from:
(1) =$C(R^{7a})$—,
(2) —$C(R^{7a})_2$—,
(3) —C(=O)—,
(4) —$S(O)_m$—,
(5) =N—, and
(6) —$N(R^{7a})$—;
T is selected from:
(1) =$C(R^{7b})$—,
(2) —$C(R^{7b})_2$—,
(3) —C(=O)—,
(4) —$S(O)_m$—,
(5) =N—, and
(6) —$N(R^{7b})$—;

$R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$ cycloalkyl, aryl, heterocycle, and heteroaryl, which ring is unsubstituted or substituted with 1-10 substituents each independently selected from $R^6$;

"heteroaryl" is a 5- to 7-membered monocyclic- or 9- to 10-membered fused bicyclic heterocyclic ring system which contains an aromatic ring, any ring of which may be saturated partially saturated, or unsaturated, and which consists of carbon atoms and from one to four heteroatoms selected from the group consisting of N, O and S, and wherein the N and S heteroatoms may optionally be oxidized, and the N may optionally be quaternized, and including any bicyclic group in which any of the above-defined heterocyclic rings is fused to a benzene ring;

"heterocyclic" is a 5- to 7-membered monocyclic- or 8- to 11-membered bicyclic heterocyclic ring system which is either saturated or unsaturatated, and which consists of carbon atoms and from one to four heteroatoms selected from the group consisting of N, O and S, and wherein the N and S heteroatoms may optionally be oxidized, and the N heteroatom may be optionally be quaternized, and including any bicyclic group in which any of the above-defined heterocyclic rings is fused to a benzene ring;

p is 0 to 2q+1, for a substituent with q carbons;

m is 0,1 or 2;

n is 1;

s is 1,2 or 3;

or a pharmaceutically acceptable salt or individual diastereomers thereof.

2. A compound of claim 1 having the formula Ia:

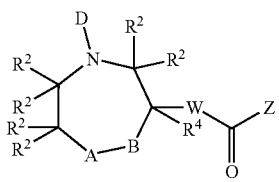

Ia wherein:

A is a bond, $C(R^2)_2$, O, $S(O)_m$ or $NR^2$;

B is $(C(R^2)_2)_n$;

n is 0 or 1; and or a pharmaceutically acceptable salt or individual diastereomers thereof.

3. A compound of claim 1 having the formula Ic:

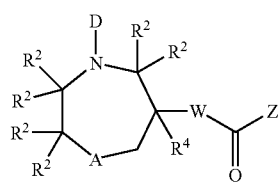

Ic wherein

A is $C(R^2)_2$, O, $S(O)_m$ or $NR^2$;

or a pharmaceutically acceptable salt or individual diastereomers thereof.

4. The compound of claim 1, wherein:

D is selected from $R^1$, $OR^1$, $N(R^1)_2$, $NR^1C(O)R^1$, $C(O)R^1$, $S(O)_mR^1$, $C(O)OR^1$, $C(O)N(R^1)_2$, $C(O)NR^{10}R^{11}$, $C(NR^1)N(R^1)_2$ and $C(NR^1)R^1$;

$R^1$ is selected from:

1) H, $C_1$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) CN,
   l) $NR^{10}R^{11}$, and
   m) $O(CO)R^4$; and 2) aryl or heteroaryl, unsubstituted or substituted with one or more substituents independently selected from:
   a) $C_{1-6}$ alkyl,
   b) $C_{3-6}$ cycloalkyl,
   c) $(F)_pC_{1-3}$ alkyl,
   d) halogen,
   e) $OR^4$,
   f) $CO_2R^4$,
   g) $(CO)NR^{10}R^{11}$,
   h) $SO_2NR^{10}R^{11}$,
   i) $N(R^{10})SO_2R^{11}$,
   j) $S(O)_mR^4$,
   k) CN,
   l) $NR^{10}R^{11}$, and,
   m) $O(CO)R^4$;

$R^2$ is selected from:

1) H, $C_0$-$C_6$ alkyl, $C_2$-$C_6$ alkynyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 sustituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $S(O)_mR^4$,
   l) CN,
   m) $NR^{10}R^{11}$, and
   n) $O(CO)R^4$; and 2) aryl or heteroaryl, unsubstituted or substituted with one more substituents independently selected from:
   a) $C_{1-6}$ alkyl,
   b) $C_{3-6}$ cycloalkyl, c) $(F)_pC_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_mR^4$,
k) CN,
l) $NR^{10}R^{11}$, and
m) $O(CO)R^4$, where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

$R^6$ is independently selected from H and:
  a) $C_{1-6}$ alkyl,
  b) $C_{3-6}$ cycloalkyl,
  c) $(F)_pC_{1-3}$ alkyl,
  d) halogen,
  e) $OR^4$,
  f) $CO_2R^4$,
  g) $(CO)NR^{10}R^{11}$,
  h) $SO_2NR^{10}R^{11}$,
  i) $N(R^{10})SO_2R^{11}$,
  j) $S(O)_mR^4$,
  k) CN,
  l) $NR^{10}R^{11}$ and
  m) $O(CO)R^4$;

Z is Z1 and:
  J is a bond and V is a bond, or
  J is a bond, V is a bond and T is —C(=O)—, or
  J is a bond, V is a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=N, $N(R^6)$—$C(R^6)_2$, N=$C(R^6)$ or $N(R^6)$—N($R^6$), or
  J is a bond, $C(R^5)_2$, O, or $NR^5$, V is a bond,
or Z is Z2 and G-L is selected from N, N—$C(R^6)_2$, C=C($R^6$), C=N and N—$C(R^6)_2$—$_{C(R^6)_2}$;

Q is selected from:
  (1) =$C(R^{7a})$—,
  (2) —$C(R^{7a})_2$—,
  (3) —C(=O)—,
  (4) —$S(O)_m$—,
  (5) =N—, and
  (6) —$N(R^{7a})$—;

T is selected from:
  (1) =$C(R^{7b})$—,
  (2) —$C(R^{7b})_2$—,
  (3) —C(=O)—,
  (4) —$S(O)_m$—,
  (5) =N—, and
  (6) —$N(R^{7b})$—;

$R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$cycloalkyl, aryl, heterocycle, and heteroaryl, which ring is unsubstituted or substituted with 1-10 substituents each each independently selected from $R^6$;

p is 0 to 2q+1, for a substituent with q carbons
m is 0 to 2;
s is 1 to 3;
or a pharmaceutically acceptable salt or individual diastereomers thereof.

5. The compound of claim 1, wherein:
$R^1$ is selected from:
1) H, $C_1$-$C_6$ alkyl, $C_{3-6}$ cycloalkyl and heterocycle, unsubstituted or substituted with one or more substituents each independently selected from:
  a) $C_{1-6}$ alkyl,
  b) $C_{3-6}$ cycloalkyl,
  c) phenyl, unsubstituted or substituted with 1-5 substituents each independently selected from $R^4$,
  d) heteroaryl, unsubstituted or substituted with 1-5 substituents each independently selected from $R^4$, and where heteroaryl is selected from: imidazole, isoxazole, oxazole, pyrazine, pyrazole, pyridazine, pyridine, pyrimidine, and thiazole;
  e) heterocycle, unsubstituted or substituted with 1-5 substituents each independently selected from $R^4$, and where heterocycle is selected from: azetidine, dioxane, dioxolane, morpholine, oxetane, piperazine, piperidine, pyrrolidine, tetrahydrofuran, and tetrahydropyran;
  f) $(F)_pC_{1-3}$ alkyl,
  g) halogen,
  h) $OR^4$,
  i) $O(CH_2)_sOR^4$,
  j) $CO_2R^4$,
  k) CN,
  l) $NR^{10}R^{11}$, and
  m) $O(CO)R^4$, and
2) aryl or heteroaryl, selected from: phenyl, imidazole, isoxazole, oxazole, pyrazine, pyrazole, pyridazine, pyridine, pyrimidine, and thiazole, unsubstituted or substituted with one or more substituents each independently selected from:
  a) $C_{1-6}$ alkyl,
  b) $C_{3-6}$ cycloalkyl,
  c) $(F)_pC_{1-3}$ alkyl,
  d) halogen,
  e) $OR^4$,
  f) $CO_2R^4$,
  g) $(CO)NR^{10}R^{11}$,
  h) $SO_2NR^{10}R^{11}$,
  i) $N(R^{10})SO_2R^{11}$,
  j) $S(O)_mR^4$,
  k) CN,
  l) $NR^{10}R^{11}$, and
  m) $O(CO)R^4$;

$R^2$ is selected from:
1) H, $C_0$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$, and where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;
   e) heterocycle, unsubstituted or substituted with 1-5 substituents where the substituents are independently selected from $R^4$, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10}R^{11}$, and
   m) $O(CO)R^4$; and
2) aryl or heteroaryl, selected from:
   phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole, unsubstituted or substituted with one or more substituents each independently selected from:
   a) $C_{1-6}$ alkyl,
   b) $C_{3-6}$ cycloalkyl,
   c) $(F)_p C_{l-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and
   m) $O(CO)R^4$, where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, $R^{10}$ and $R^{11}$ are each independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is independently selected from: H, $C_{1-6}$ alkyl, $(F)_p C_{1-6}$ alkyl, $C_{3-6}$ cycloalkyl, aryl, heteroaryl and phenyl, unsubstituted or substituted with hydroxy or $C_1$-$C_6$ alkoxy;

W is $NR^4$ or $C(R^4)_2$;

$R^6$ is independently selected from H and:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and
   m) $O(CO)R^4$;

Z is Z1 and:
   J is a bond, V is a bond, Q is —$N(R^{7a})$—, and T is —C(=O)—, or
   J is a bond, V is a bond, Q is —$C(R^{7a})_2$—, and T is —C(=O)—, or
   J is a bond, V is a bond, Q is —N=, and T is =$C(R^{7b})$—, or
   J is a bond, V is a bond, Q is —$C(R^{7a})_2$—, and T is —$C(R^{7b})_2$—, or
   J is a bond, V is a bond, Q is —$C(R^{7a})$=, T is =$C(R^{7b})$—, where the atoms to which $R^{7a}$ and $R^{7b}$ are attached join to form a benzene, pyridine, or diazine ring, or
   J is a bond, V is $C(R^6)_2$, Q is —$C(R^{7a})$=, T is =$C(R^{7b})$—, and the atoms to which $R^{7a}$ and $R^{7b}$ are attached join to form a benzene, or pyridine ring, or
   J is O, V is a bond, Q is —$C(R^{7a})$=, T is =$C(R^{7b})$—, and the atoms to which $R^{7a}$ and $R^{7b}$ are attached are joined together to form a benzene, or pyridine ring, or Z is Z2 and:
   G-L is N, Q is —$C(R^{7a})_2$—, and T is —$C(R^{7b})_2$—, or
   G-L is N, Q is —$C(R^{7a})$= and T is =$C(R^{7b})$—, or
   G-L is N, Q is —N=, and T is =$C(R^{7b})$—, or
   G-L is N, Q is —$C(R^{7a})_2$—, and T is —C(O)—, or
   G-L is C=$C(R^6)$, Q is —$C(R^{7a})$= and T is =$C(R^{7b})$—, or
   G-L is C=$C(R^6)$, Q is —$C(R^{7a})$= and T is =N—, or
   G-L is C=$C(R^6)$, Q is —N= and T is =$C(R^{7b})$—, or
   G-L is C=N, Q is —$C(R^{7a})$= and T is =$C(R^{7b})$—, or
   G-L is N, Q is —$C(R^{7a})$=, and T is =$C(R^{7b})$—, and the atoms to which $R^{7a}$ and $R^{7b}$ are attached join to form a benzene, pyridine, or diazine ring, or
   G-L is N—$C(R^6)_2$, Q is —$C(R^{7a})$=, and T is =$C(R^{7b})$—, and the atoms to which $R^{7a}$ and $R^{7b}$ are attached join to form a benzene, or pyridine ring, or
   G-J is C=N, Q is —$C(R^{7a})$=, and T is =$C(R^{7b})$—, and the atoms to which $R^{7a}$ and $R^{7b}$ are attached join to form a benzene ring, or
   G-L is C=$C(R^6)$, Q is —$C(R^{7a})$=, and T is =$C(R^{7b})$—, and the atoms to which $R^{7a}$ and $R^{7b}$ are attached join to form a benzene ring, or G-L is N—C(R⁶)₂—C(R⁶)₂, Q is —C(R⁷ᵃ)═, and T is ═C(R⁷ᵇ)—, and the atoms to which R⁷ᵃ and R⁷ᵇ are attached join to form a benzene ring;

R³ is independently selected from H, substituted or unsubstituted C₁-C₃ alkyl, F, CN and CO₂R⁴;

R⁷ᵃ and R⁷ᵇ are each independently selected from R², where R⁷ᵃ and R⁷ᵇ and the atom or atoms to which they are attached optionally join to form a ring selected from C₃₋₆cycloalkyl, aryl, heterocycle, and heteroaryl which is unsubstituted or substituted with 1-10 substituents each independently selected from R⁶;

p is 0 to 2q+1, for a substituent with q carbons m is 0 to 2;

s is 1 to 3;

or a pharmaceutically acceptable salt or and individual diastereomers thereof.

6. A compound selected from:

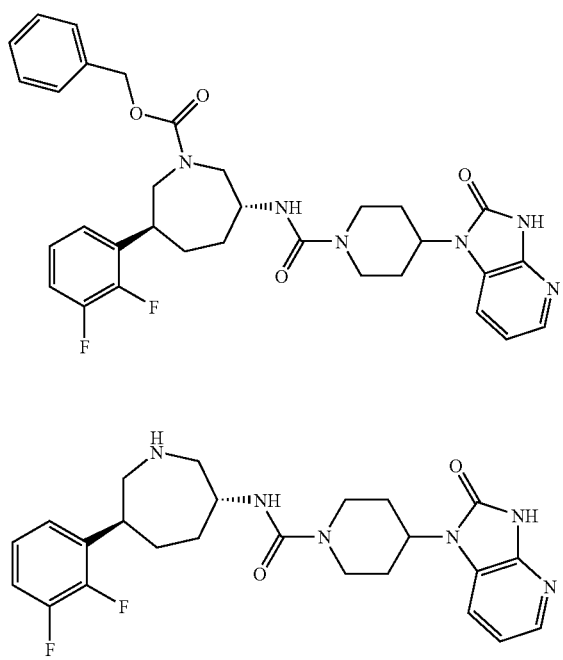

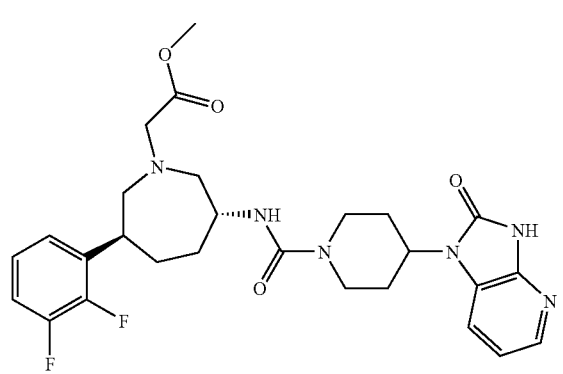

-continued

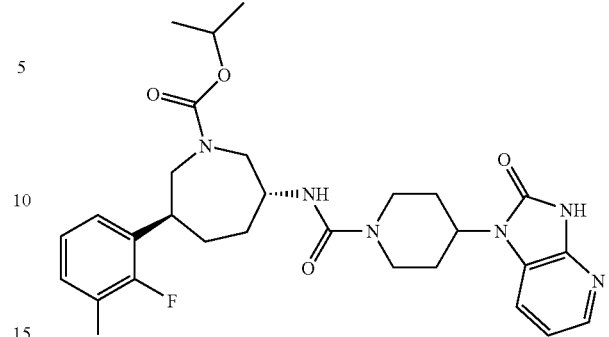

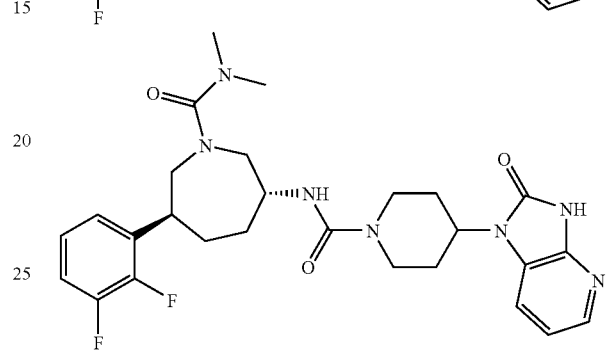

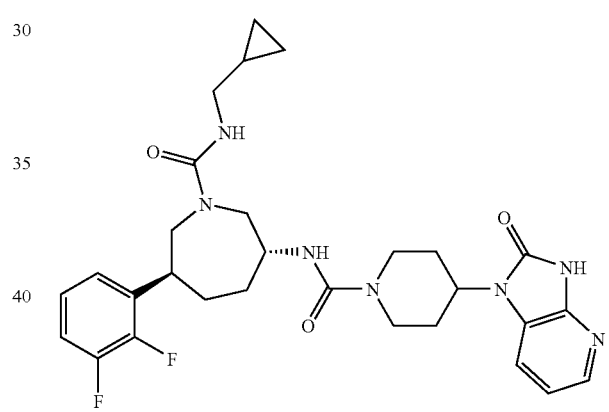

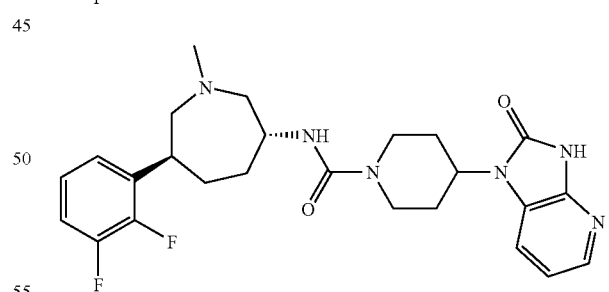

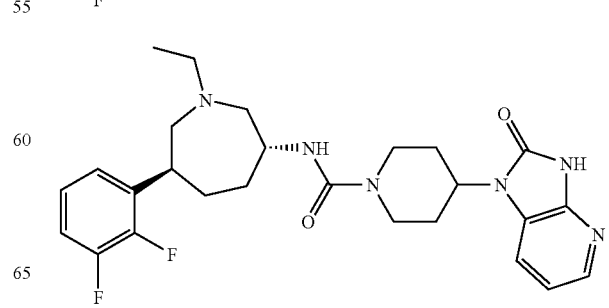

-continued
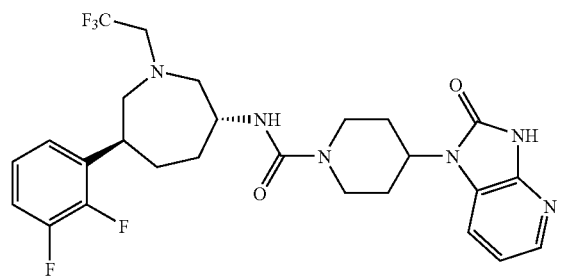
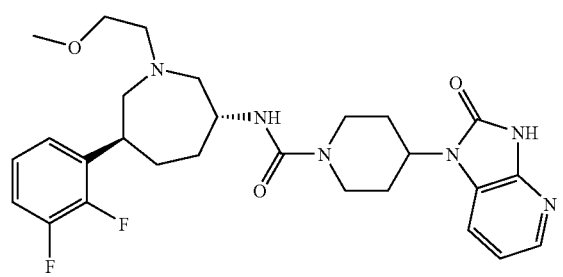
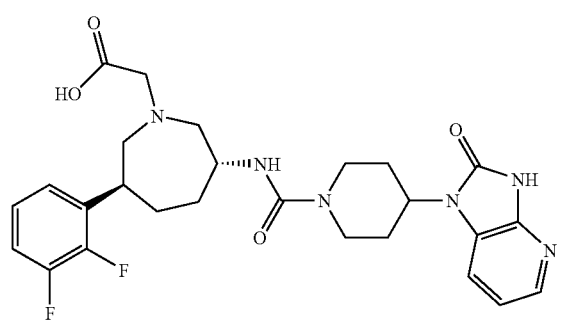
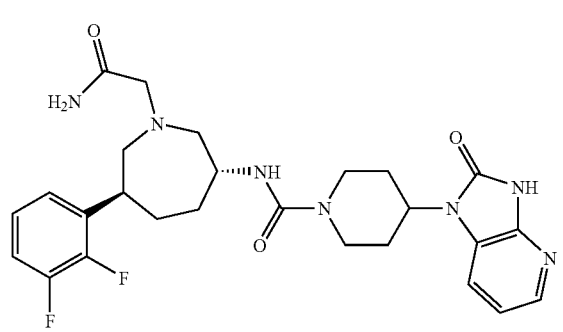
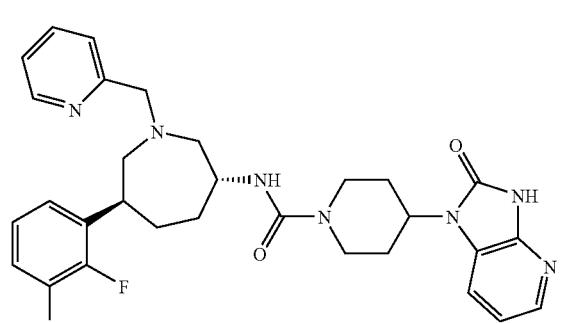
-continued
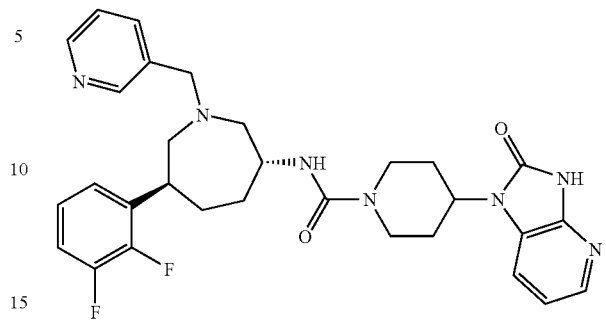
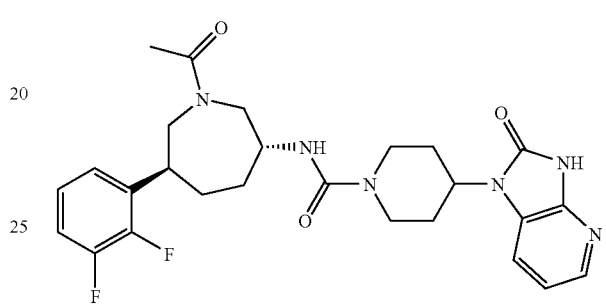
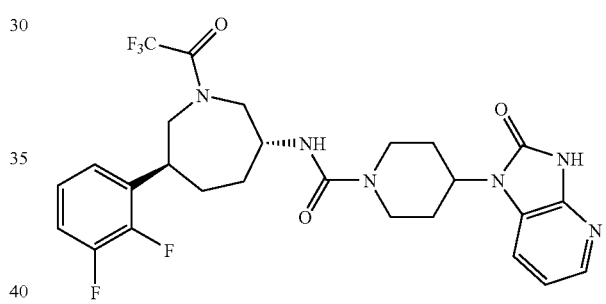
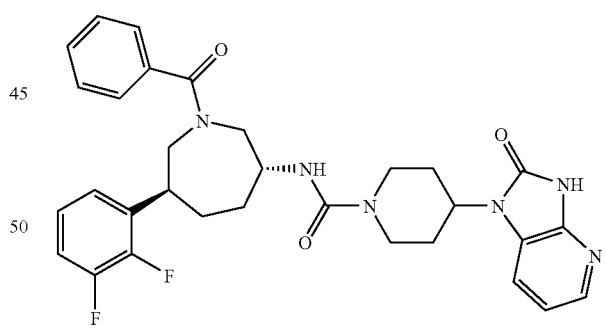
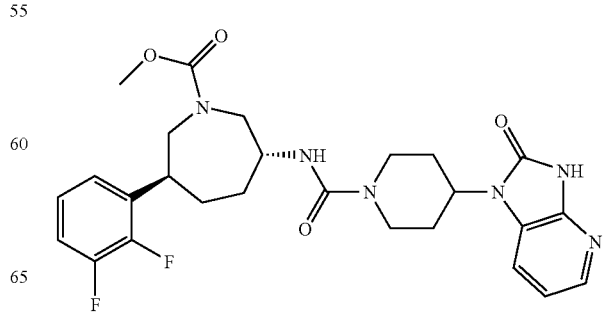

141
-continued
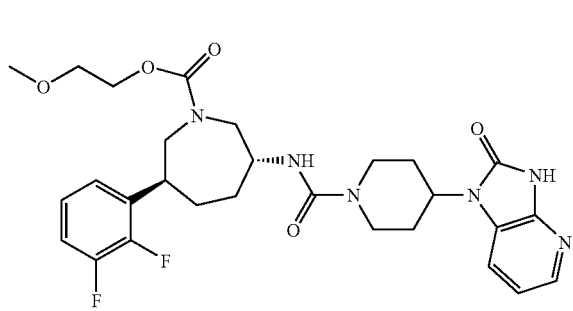
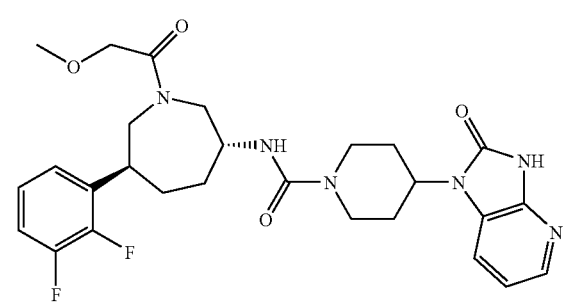
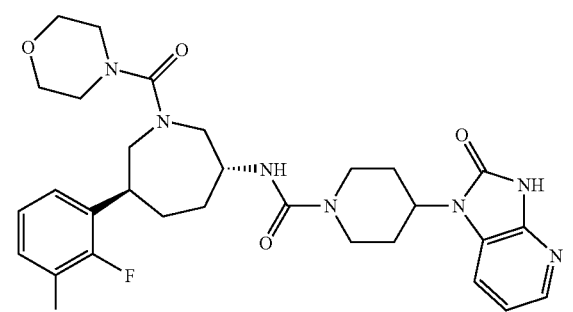
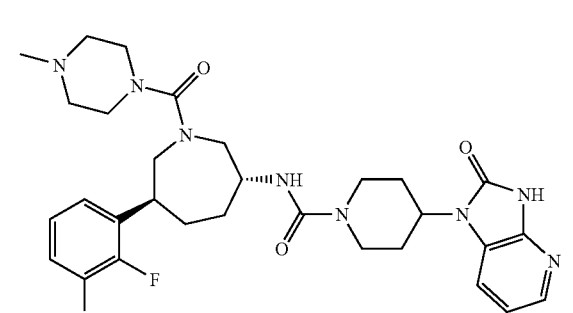
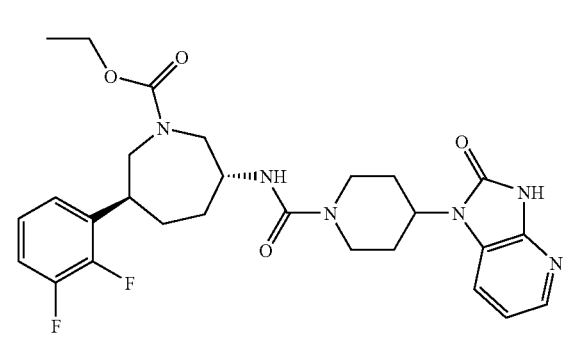
142
-continued
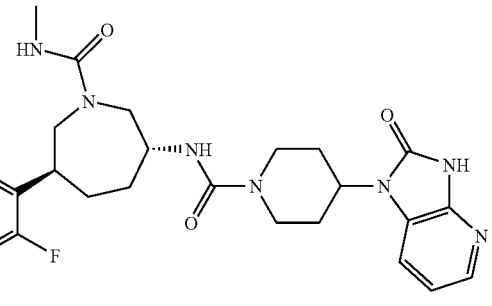
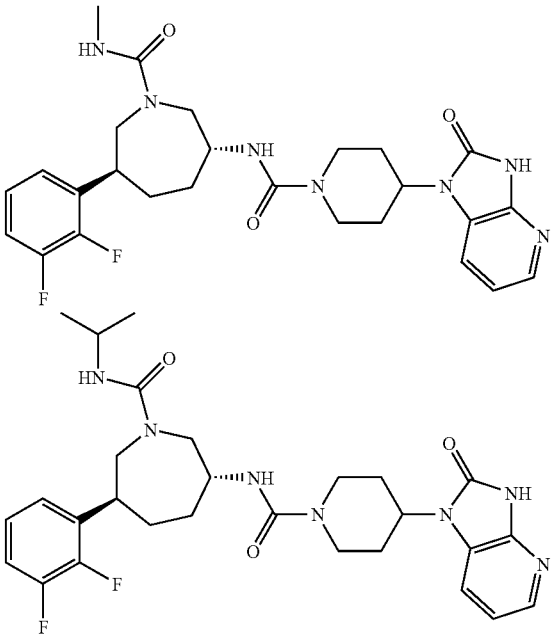
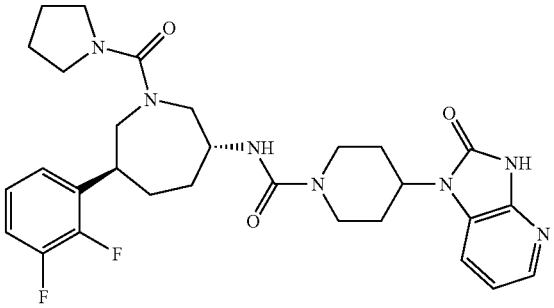
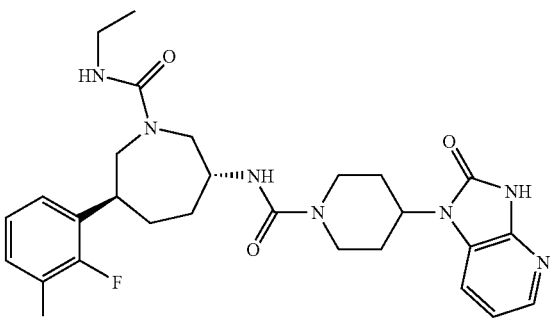
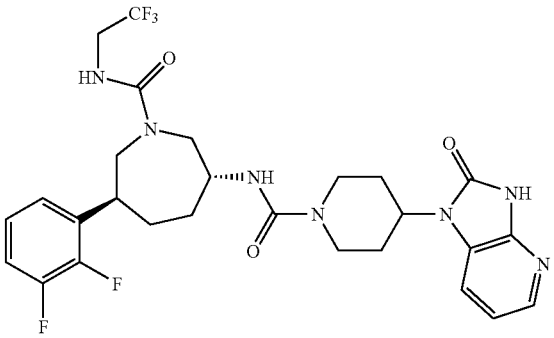

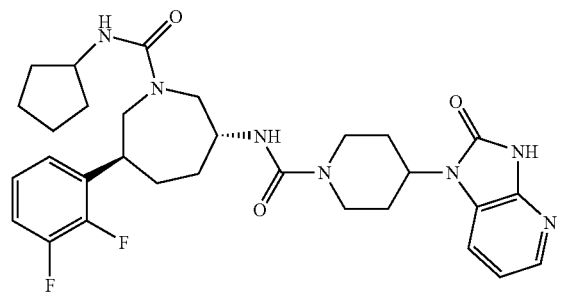
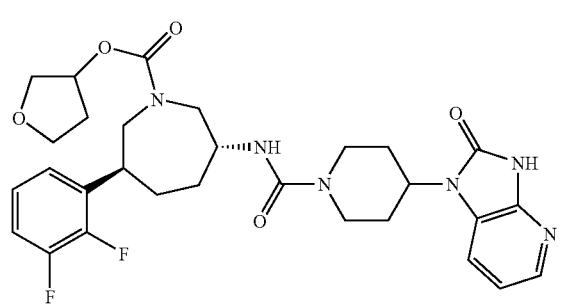
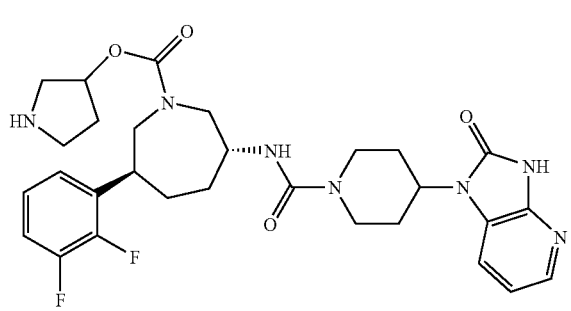
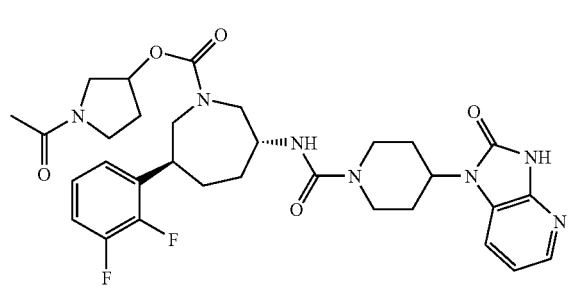
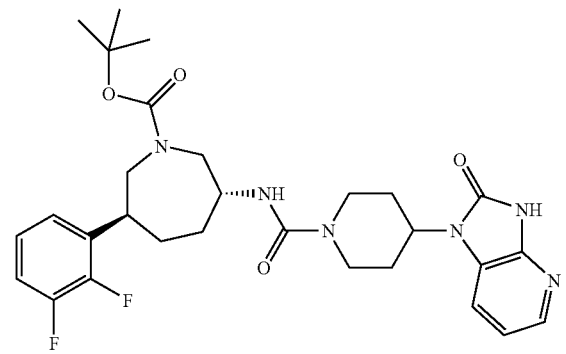
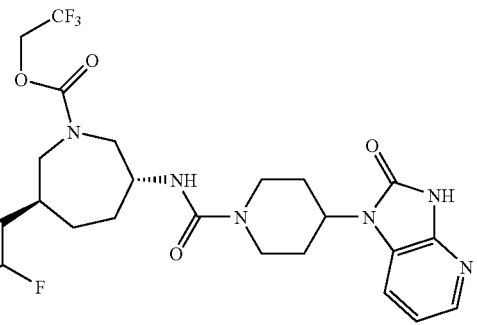
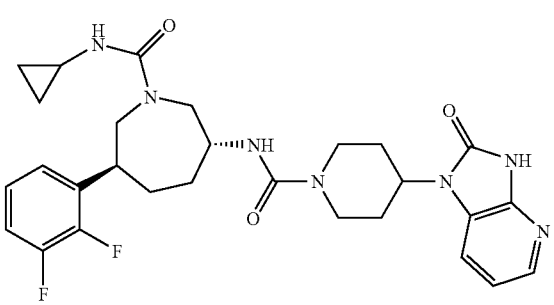
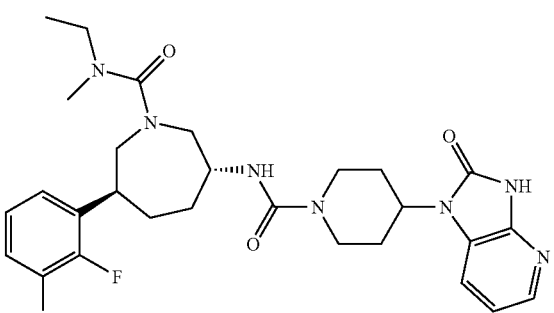
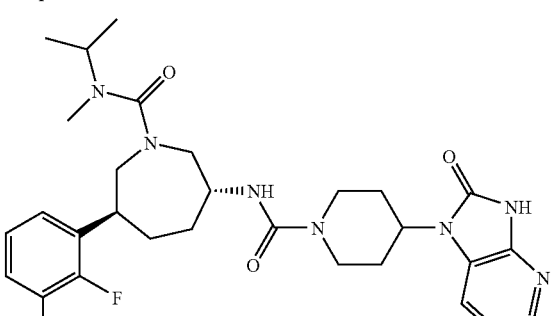
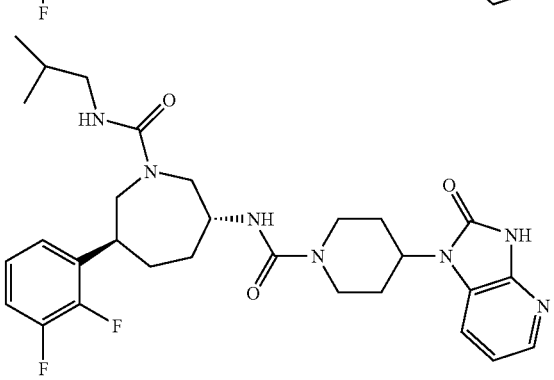

145
-continued
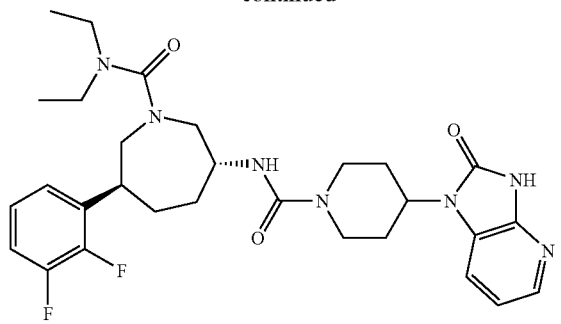
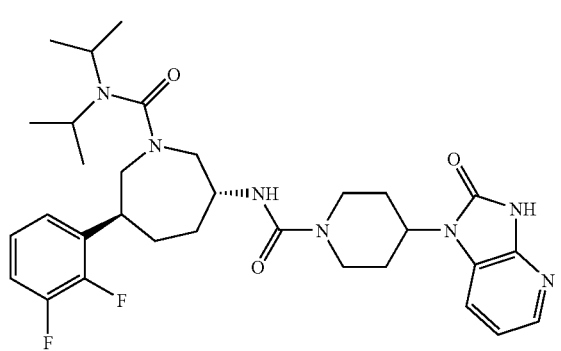
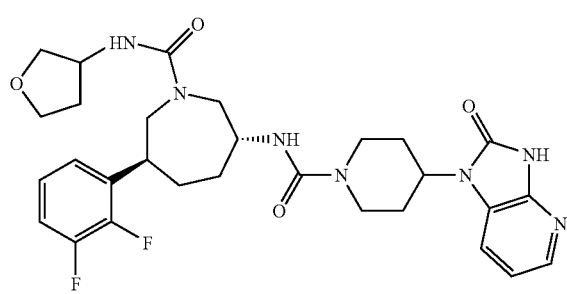
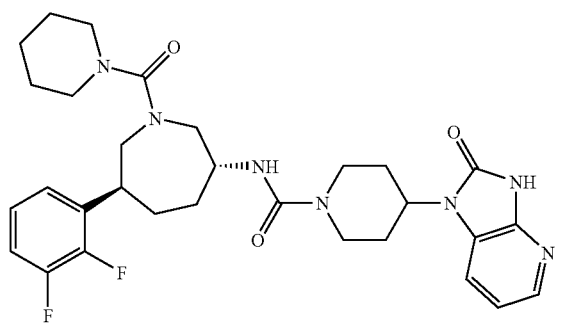
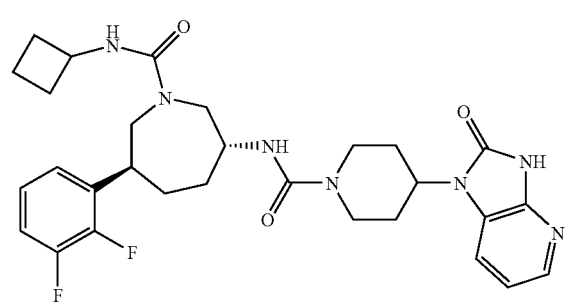
146
-continued
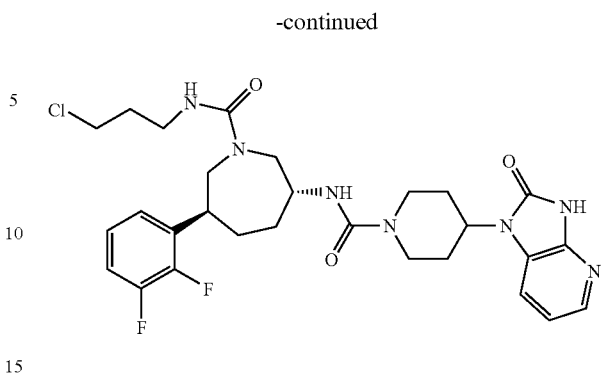
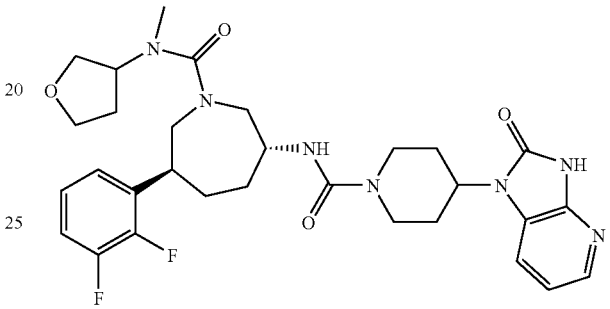
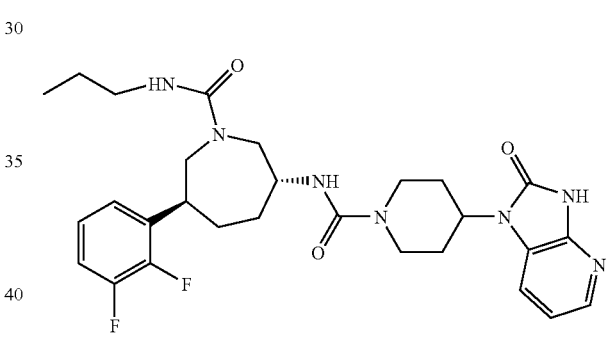
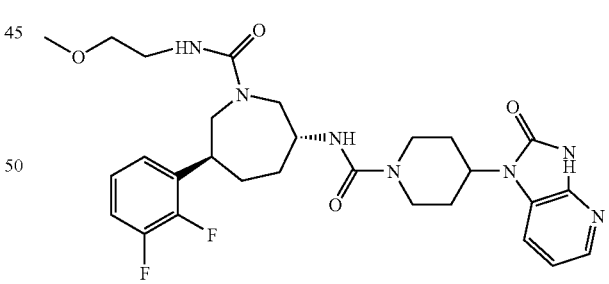
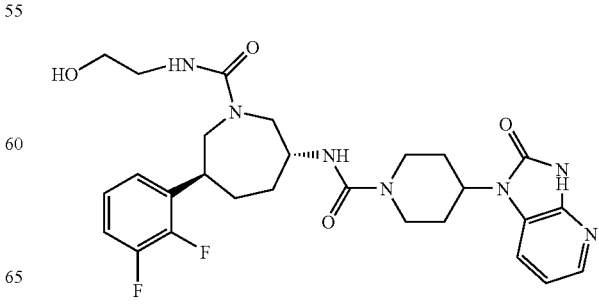

-continued
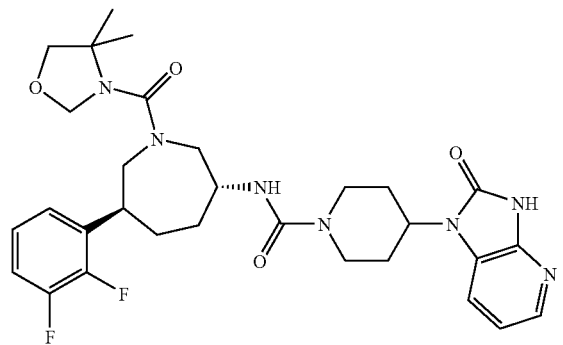
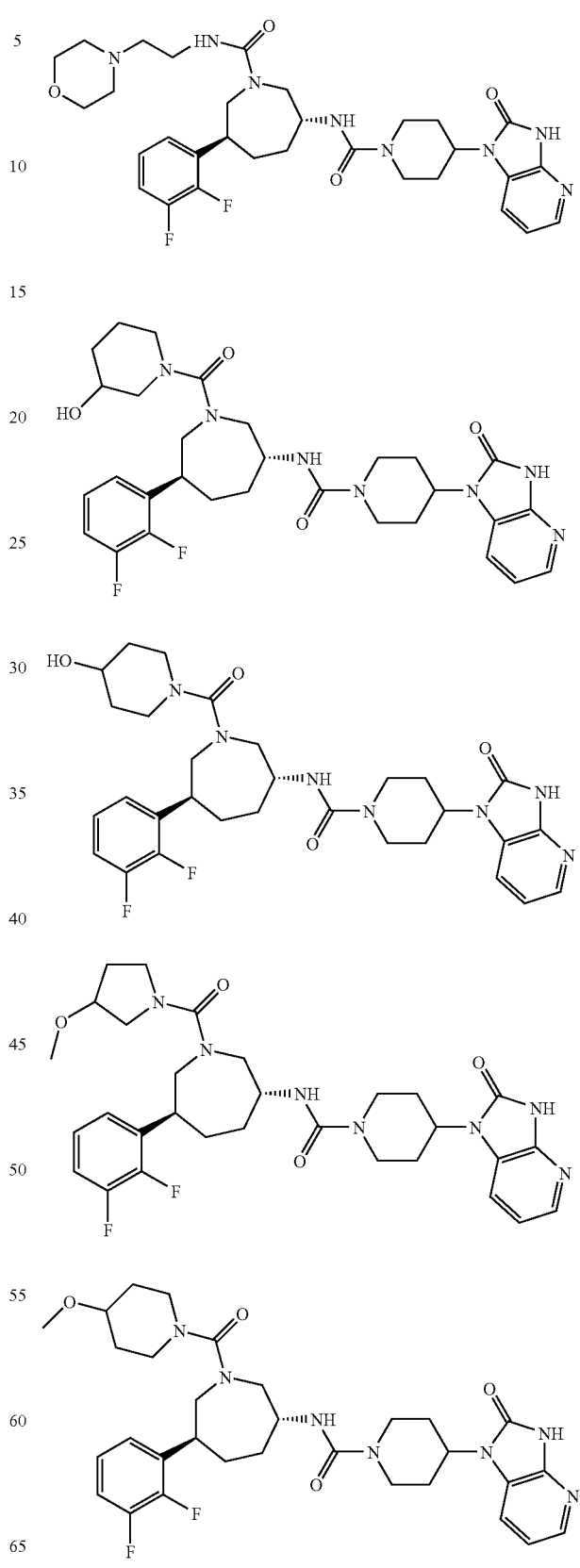

-continued
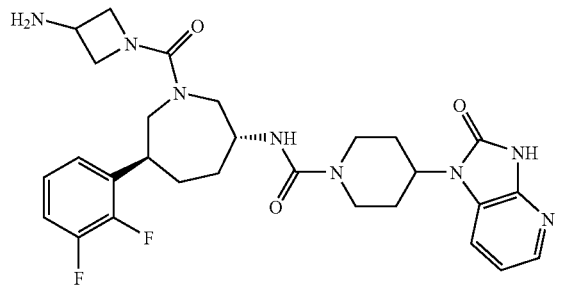
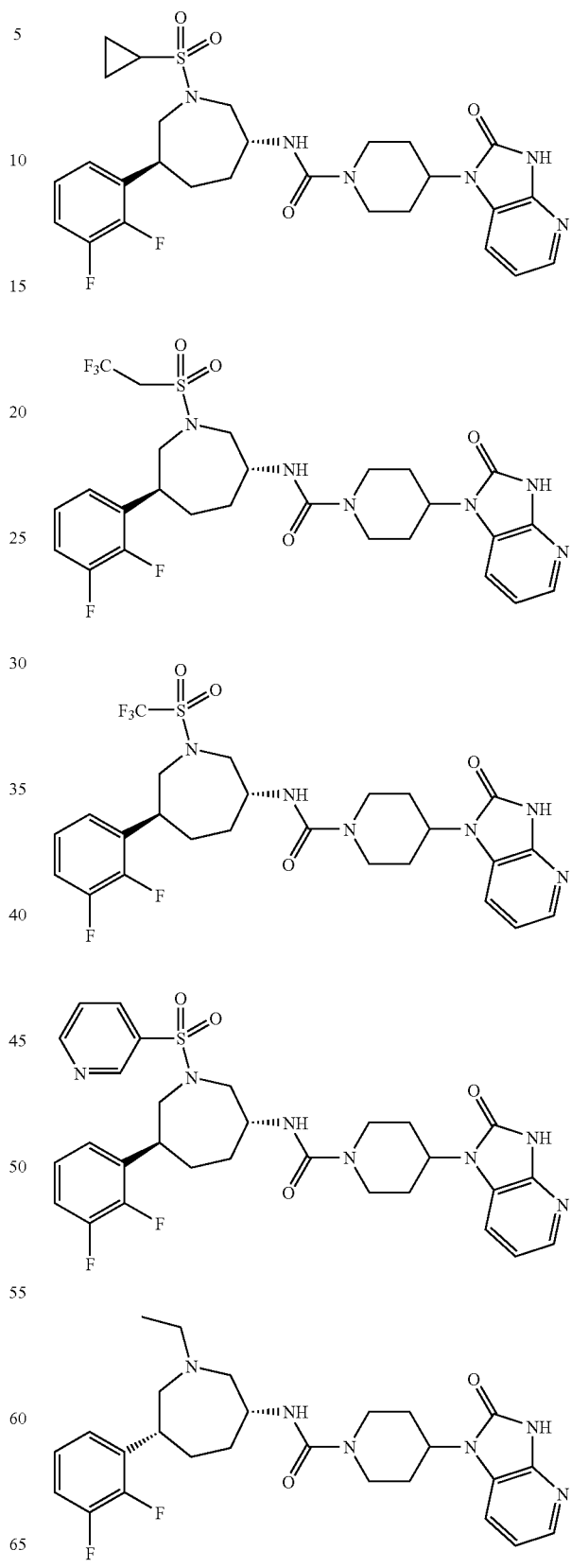

-continued

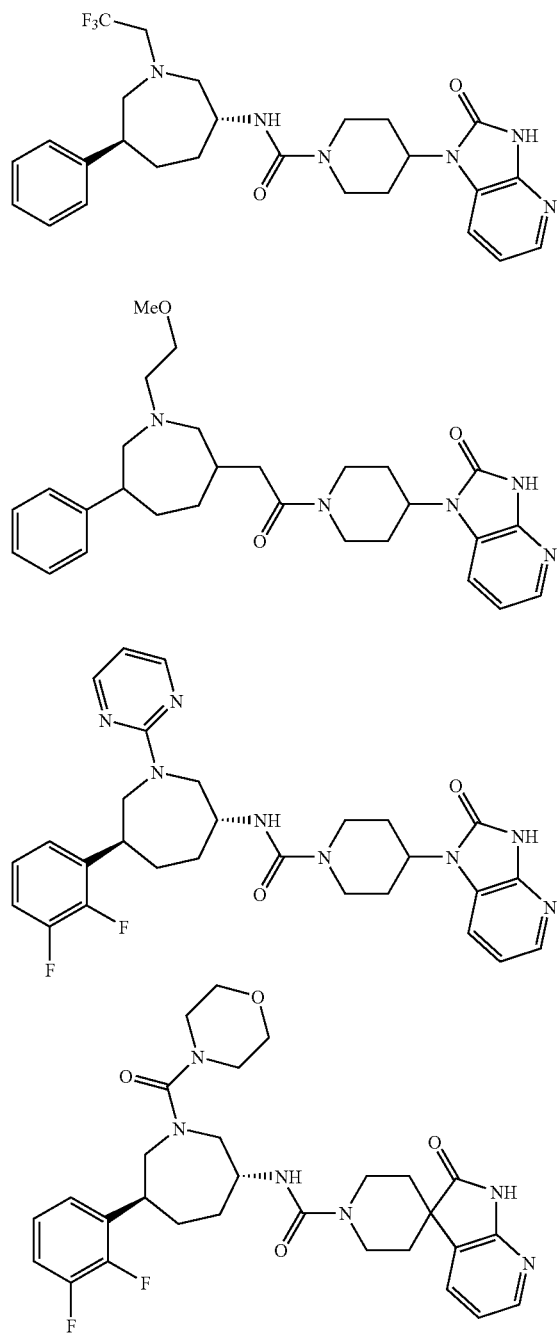

-continued

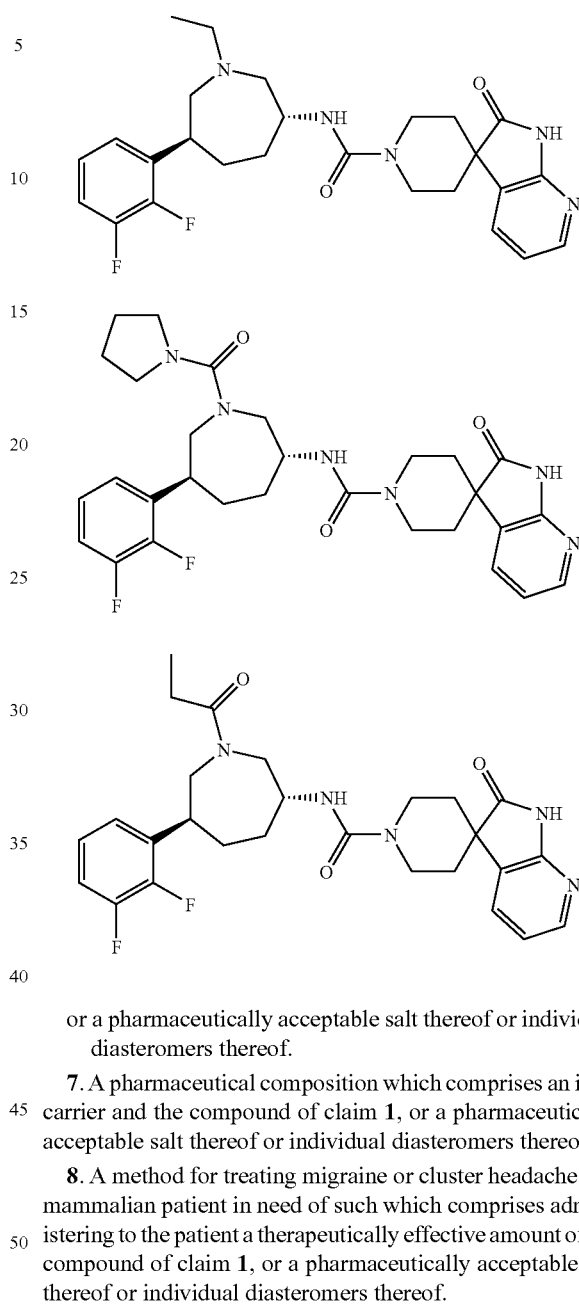

or a pharmaceutically acceptable salt thereof or individual diasteromers thereof.

7. A pharmaceutical composition which comprises an inert carrier and the compound of claim 1, or a pharmaceutically acceptable salt thereof or individual diasteromers thereof.

8. A method for treating migraine or cluster headache in a mammalian patient in need of such which comprises administering to the patient a therapeutically effective amount of the compound of claim 1, or a pharmaceutically acceptable salt thereof or individual diasteromers thereof.

* * * * *

UNITED STATES PATENT AND TRADEMARK OFFICE
CERTIFICATE OF CORRECTION

| | | |
|---|---|---|
| PATENT NO. | : 7,745,427 B2 | Page 1 of 1 |
| APPLICATION NO. | : 11/665943 | |
| DATED | : June 29, 2010 | |
| INVENTOR(S) | : Paone et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 539 days.

Signed and Sealed this
Fifteenth Day of February, 2011

David J. Kappos
*Director of the United States Patent and Trademark Office*